US008426201B2

(12) United States Patent
Maher et al.

(10) Patent No.: US 8,426,201 B2
(45) Date of Patent: Apr. 23, 2013

(54) ION CHANNEL ASSAY METHODS

(75) Inventors: Michael P. Maher, San Diego, CA (US); Jesus E. Gonzalez, III, San Diego, CA (US)

(73) Assignee: Vertex Pharmaceuticals (San Diego) LLC, San Diego, CA (US)

( * ) Notice: Subject to any disclaimer, the term of this patent is extended or adjusted under 35 U.S.C. 154(b) by 0 days.

(21) Appl. No.: 12/568,604

(22) Filed: Sep. 28, 2009

(65) Prior Publication Data

US 2010/0081163 A1    Apr. 1, 2010

Related U.S. Application Data

(60) Division of application No. 10/620,312, filed on Jul. 14, 2003, now Pat. No. 7,615,356, which is a continuation-in-part of application No. 09/804,480, filed on Mar. 12, 2001, now Pat. No. 7,312, 043.

(60) Provisional application No. 60/217,671, filed on Jul. 10, 2000.

(51) Int. Cl.
*G01N 33/53* (2006.01)
*C12N 5/00* (2006.01)

(52) U.S. Cl.
USPC .......................................................... 435/375

(58) Field of Classification Search ................ None
See application file for complete search history.

(56) References Cited

U.S. PATENT DOCUMENTS

| | | | |
|---|---|---|---|
| 4,072,578 A | 2/1978 | Cady et al. |
| 4,461,304 A | 7/1984 | Kuperstein |
| 4,514,500 A | 4/1985 | Giaever et al. |
| 4,628,933 A | 12/1986 | Michelson |
| 4,677,989 A | 7/1987 | Robblee |
| 4,695,547 A | 9/1987 | Hilliard et al. |
| 4,699,881 A | 10/1987 | Matschke |
| 4,801,543 A | 1/1989 | Arnold et al. |
| 4,969,468 A | 11/1990 | Byers et al. |
| 4,970,154 A | 11/1990 | Chang |
| 5,024,223 A | 6/1991 | Chow |
| 5,128,257 A | 7/1992 | Baer |
| 5,178,161 A | 1/1993 | Kovacs |
| 5,187,096 A | 2/1993 | Giaever et al. |
| 5,194,133 A | 3/1993 | Clark et al. |
| 5,405,367 A | 4/1995 | Schulman et al. |
| 5,422,272 A | 6/1995 | Papp et al. |
| 5,432,086 A | 7/1995 | Fränzl et al. |
| 5,437,982 A | 8/1995 | Catterall et al. |
| 5,439,440 A | 8/1995 | Hofmann |
| 5,545,130 A | 8/1996 | Hofmann et al. |
| 5,563,067 A | 10/1996 | Sugihara et al. |
| 5,571,158 A | 11/1996 | Bolz et al. |
| 5,643,742 A | 7/1997 | Malin et al. |
| 5,810,725 A | 9/1998 | Sugihara et al. |
| 5,855,801 A | 1/1999 | Lin et al. |
| 5,935,155 A | 8/1999 | Humayun et al. |
| 5,957,958 A | 9/1999 | Schulman et al. |
| 5,965,452 A | 10/1999 | Kovacs |
| 5,972,694 A | 10/1999 | Mathus |
| 5,981,268 A | 11/1999 | Kovacs et al. |
| 6,008,038 A | 12/1999 | Kröger et al. |
| 6,009,347 A | 12/1999 | Hofmann |
| 6,024,702 A | 2/2000 | Iversen |
| 6,031,711 A | 2/2000 | Tennent et al. |
| 6,038,478 A | 3/2000 | Yuen et al. |
| 6,046,002 A | 4/2000 | Davis et al. |
| 6,051,422 A | 4/2000 | Kovacs et al. |
| 6,063,260 A | 5/2000 | Olesen et al. |
| 6,099,960 A | 8/2000 | Tennent et al. |
| 6,205,016 B1 | 3/2001 | Niu |
| 6,352,853 B1 | 3/2002 | King et al. |
| 6,376,233 B1 | 4/2002 | Wolf et al. |
| 6,686,193 B2 | 2/2004 | Maher et al. |
| 6,969,449 B2 | 11/2005 | Maher et al. |
| 7,176,016 B2 | 2/2007 | Maher et al. |
| 7,276,206 B2 | 10/2007 | Augustine et al. |
| 7,312,043 B2 | 12/2007 | Maher et al. |
| 7,399,599 B2 | 7/2008 | Maher et al. |
| 7,611,850 B2 | 11/2009 | Maher et al. |
| 7,615,356 B2 | 11/2009 | Maher et al. |
| 7,615,357 B2 | 11/2009 | Maher et al. |
| 7,695,922 B2 | 4/2010 | Maher et al. |

FOREIGN PATENT DOCUMENTS

| | | |
|---|---|---|
| DE | 195 29 371 | 2/1997 |
| EP | 0 594 282 | 4/1994 |
| EP | 1 067 378 A1 | 1/2001 |
| WO | 96/41166 | 12/1996 |
| WO | WO 96/41166 | 12/1996 |
| WO | WO 97/05922 | 2/1997 |
| WO | WO 98/54294 A | 12/1998 |
| WO | WO 00/25121 | 5/2000 |
| WO | WO 00/34434 | 6/2000 |
| WO | WO 00/68686 | 11/2000 |
| WO | WO 02/08748 | 1/2002 |

OTHER PUBLICATIONS

Sinha et al. (1995) Journal of Neuroscience Methods 60: 49-60.*
Arndts, Oral Presentation Abstract, Second International Cell Analysis Products Users Meeting in Hilton Head Island, South Carolina, USA (Jun. 3-5, 1998).
Barr and Plonsey, Biophys. J. 61, 1164-1175 (1992).
Barr and Plonsey, IEEE 42, 1185-11911 (1995).
Brust-Mascher, I et al., "Calcium Waves Induced by Large Voltage Pulses in Fish Keratocytes", Biophysical Journal, (1998) 75(4): 1669-1678.

(Continued)

*Primary Examiner* — Michael Pak
(74) *Attorney, Agent, or Firm* — Knobbe Martens Olson & Bear LLP

(57) ABSTRACT

A method of characterizing the biological activity of a candidate compound may include exposing cells to the candidate compound, and then exposing the cells to a repetitive application of electric fields so as to set the transmembrane potential to a level corresponding to a pre-selected voltage dependent state of a target ion channel.

12 Claims, 48 Drawing Sheets

OTHER PUBLICATIONS

Cartee and Plonsey, IEEE 39, 76-85 (1992).
Cartee and Plonsey, Med & Biol. Eng. & Comp. 30 389-398 (1992).
Connolly, P. et al. An Extracellular Microelectrode Array for Monitoring Electrogenic Cells in Culture. Biosensors and Bioelectronics. 1990. 5:223-234.
Denyer, J et al., "HTS Approaches to Voltage-Gated Ion Channel Drug Discovery Today", (1998) 3(7): 323-332.
Eppich et al., Nature Biotech. 18, 882-887 (2000).
Fishler, et al., Mechanisms of Cardiac Cell Excitation with Premature Monophasic and Biphasic Field Stimuli: A Model Study, Blophys J. 70(3):1347-62 Mar. 1996.
Giuliano, K.A., et al., "Fluorescent-protein biosensors: new tools for drug discovery", Trends in Biotechnology, vol. 16, No. 3, pp. 135-140, (Mar. 1998).
González, J.E., et al., "Voltage sensing by fluorescence resonance energy transfer in single cells", Biophysical Journal, vol. 69, No. 4, pp. 1272-1280, (Oct. 1995).
González, J.E., et al., "Cell-based assays and instrumentation for screening ion-channel targets", Drug Discover Today, vol. 4, No. 9, pp. 431-439, (Sep. 1999).
Greenberg, et al. IEEE 46, 505-514 (1999).
Gross, et al. Biophys. J. 50, 339-348 (1986).
Huang, et al. Characterization of voltage-gated sodium-channel blockers by electrical stimulation and fluorescence detection of membrane potential; vol. 24 No. 4 Apr. 2006 Nature Biotechnology.
Jacobs et al. "Control of Action Potential-Induced $Ca^{2+}$ Signaling in the Soma of Hippocampal Neurons by $Ca^{2+}$ Release from Intracellular Stores", (1997) Journal of Neuroscience 17(11):4129-4135.
Jentsch and Günther, BioEssays 19, 117-126 (1997).
Klee and Plonsey, Biophys. J. 12 1661-1675 (1972).
Klee and Plonsey, IEEE 23, 347-354 (1976).
Mitchell et al., J. Biomed. Eng. 14, 52-56 (1992).
Plonsey and Barr, IEEE 42 329-336 (1995).
Plonsey and Barr, IEEE 9/10 130-137 (1998.).
Plonsey, Med & Biol. Eng. & Comput. 19 311-315 (1981).
Plonsey, Med. & Biol. Eng. & Comput. 33 337-340 (1995).
Rattay, Neuroscience 89 335-346 (1999).
Reiner et al., "Use of a Membrane Potential—Sensitive Probe to Assess Biological Expression of the Cystic Fibrosis Transmembrane Conductance Regulator" (1995) Human Gene Therapy 6:1275-1283.
Roth, Critical Reviews in Biomed. Eng. 22 263-305 (1994).
Roweli, Biophotonics Int. 12 25-26 (2000).
Schmidt et al., Proc. Natl. Acad. Sci. USA 94 8948-8953 (1997).
Sinha et al., "Simultaneous Optical Recording of Evoked and Spontaneous Transients of Membrane Potential and Intracellular Calium Concentration with High Spatio-Temporal Resolution" (1995) Journal of Neuroscience Methods 60:49-60.
Stone et al., J. Cardiovascular Electrophysiology 10 92-107 (1999).
Svirskis et al., American Phys. Soc. 0022-3077 579-586 (1997).
Tung and Borderies, Biophys. J. 63 371-386 (1992).
Tung et al., Circulation Research 69 722-730 (1991).
Zhou, et al., Circulation Research 83 1003-1014 (1998).
Teissié et al., An Experimental Evaluation of the Critical Potential Difference Inducing Cell Membrane Electropermeabilization, Biophysical Journal, Jul. 1993, pp. 409-413, vol. 65, Biophysical Society.

* cited by examiner

ION CHANNEL ASSAY METHODS

CROSS REFERENCE TO RELATED APPLICATIONS

This application is a divisional of U.S. application Ser. No. 10/620,312, filed on Jul. 14, 2003, entitled ION CHANNEL ASSAY METHODS, now U.S. Pat. No. 7,615,356, which application is a continuation-in-part of U.S. patent application Ser. No. 09/804,480, entitled "ION CHANNEL ASSAY METHODS", filed Mar. 12, 2001, now U.S. Pat. No. 7,312,043.

This application also claims priority under 35 U.S.C. Section 119(e) to U.S. Provisional Patent Application No. 60/217,671, entitled "INSTRUMENTATION AND METHODS FOR ELECTRICAL STIMULATION", filed on Jul. 10, 2000. Each of these applications are hereby incorporated by reference in their entireties.

BACKGROUND OF THE INVENTION

1. Field of the Invention

The present invention relates generally to instrumentation and methods for manipulating membrane potentials of living cells via electrical stimulation.

2. Description of the Related Art

It has long been known that the interior of animal and plant cells is electrically negative with respect to the exterior. The magnitude of this potential difference is generally between 5 and 90 mV, with most of the potential being developed across the cell membrane. The transmembrane potential of a given cell is set by the balance of the activities of ion transporters and channels which create and maintain the electrochemical gradient, and the activities of ion channels, passive diffusion and other factors, that allow ions to flow across the plasma membrane.

Ion channels participate in, and regulate, cellular processes as diverse as the generation and timing of action potentials, energy production, synaptic transmission, secretion of hormones and the contraction of muscles, etc. Many drugs exert their specific effects via modulation of ion channels. Examples include antiepileptic compounds like phenytoin and lamotrigine, which block voltage-dependent sodium channels in the brain, antihypertensive drugs like nifedipine and diltiazem, which block voltage-dependent calcium channels in smooth muscle cells, and stimulators of insulin release like glibenclamide and tolbutamide, which block ATP-regulated potassium channels in the pancreas.

Finding new drugs which have specific modulatory effects on ion channels requires methods for measuring and manipulating the membrane potential of cells with the ion channels present in the membrane. A number of methods exist today that can be used to measure cell transmembrane potentials and to measure the activities of specific ion channels. Probably the best known approach is the patch clamp, originally developed by Neher, Sakmann, and Steinback. (The Extracellular Patch Clamp, A Method For Resolving Currents Through Individual Open Channels In Biological Membranes", Pfluegers Arch. 375; 219-278, 1978). Other methods include optical recording of voltage-sensitive dyes (Cohen et al., Annual Reviews of Neuroscience 1: 171-82, 1978) and extracellular recording of fast events using metal (Thomas et al., Exp. Cell Res. 74: 61-66, 1972) or field effect transistors (FET) (Fromherz et al., Science 252: 1290-1293, 1991) electrodes.

The patch clamp technique allows measurement of ion flow through ion channel proteins and the analysis of the effect of drugs on ion channels function. In brief, in the standard patch clamp technique, a thin glass pipette is heated and pulled until it breaks, forming a very thin (<1 µm in diameter) opening at the tip. The pipette is filled with salt solution approximating the intracellular ionic composition of the cell. A metal electrode is inserted into the large end of the pipette, and connected to associated electronics. The tip of the patch pipette is pressed against the surface of the cell membrane. The pipette tip seals tightly to the cell and isolates a few ion channel proteins in a tiny patch of membrane. The activity of these channels can be measured electrically (single channel recording) or, alternatively, the patch can be ruptured allowing measurements of the combined channel activity of the entire cell membrane (whole cell recording).

During both single channel recording and whole-cell recording, the activity of individual channel subtypes can be further resolved by imposing a "voltage clamp" across the membrane. Through the use of a feedback loop, the "voltage clamp" imposes a user-specified potential difference across the membrane, allowing measurement of the voltage, ion, and time dependencies of various ion channel currents. These methods allow resolution of discrete ion channel subtypes.

A major limitation of the patch clamp technique as a general method in pharmacological screening is its low throughput. Typically, a single, highly trained operator can test fewer than ten compounds per day using the patch clamp technique. Furthermore the technique is not easily amenable to automation, and produces complex results that require extensive analysis by skilled electrophysiologists. By comparison, the use of optical detection systems provides for significantly greater throughput for screening applications (currently, up to 100,000 compounds per day), while at the same time providing for highly sensitive analysis of transmembrane potential. Methods for the optical sensing of membrane potential are typically based on translocation, redistribution, orientation changes, or shifts in spectra of fluorescent, luminescent, or absorption dyes in response to the cellular membrane potential (see generally González, et al., Drug Discovery Today 4:431-439, 1999).

A preferred optical method of analysis has been previously described (González and Tsien, Chemistry and Biology 4: 269-277, 1997; González and Tsien, Biophysical Journal 69: 1272-1280, 1995; and U.S. Pat. No. 5,661,035 issued Aug. 26, 1997, hereby incorporated by reference). This approach typically comprises two reagents that undergo energy transfer to provide a ratiometric fluorescent readout that is dependent upon the membrane potential. The ratiometric readout provides important advantages for drug screening including improved sensitivity, reliability and reduction of many types of experimental artifacts.

Compared to the use of a patch clamp, optical methods of analysis do not inherently provide the ability to regulate, or clamp, the transmembrane potential of a cell. Clamping methods are highly desirable because they provide for significantly enhanced, and more flexible methods of ion channel measurement. A need thus exists for reliable and specific methods of regulating the membrane potentials of living cells that are compatible with optical methods of analysis and are readily amendable to high throughput analysis.

SUMMARY OF THE INVENTION

In other embodiments, a method of characterizing the biological activity of a candidate compound includes: placing a population of cells into an area of observation in a sample well; exposing the population of cells to the compound; exposing the population of cells to electric fields, wherein the electric fields include a series of pulses; monitoring changes in the transmembrane potential of the population of cells; and comparing concentration dependence of transmembrane potential response to the electric fields at a first portion of the series of pulses with concentration dependence of transmembrane potential response to the electric fields at a second portion of the series of pulses. In some advantageous embodiments, the monitoring includes optically monitoring, such as by detecting fluorescence emission of a FRET based voltage sensor from an area of observation containing the population of cells. In some advantageous embodiments, the changes in the transmembrane potential are indicative of use dependent block of an ion channel in the population of cells.

BRIEF DESCRIPTION OF THE DRAWINGS

FIG. 32A shows the results of four compounds while FIG. 32B superimposes tetracaine and TTX to illustrate the distinction between a use-dependent and non-use-dependent compound.

FIG. 36A Shows the results for lamotrigine block at 50 µM for different time intervals while

DETAILED DESCRIPTION OF THE PREFERRED EMBODIMENTS

Figure 1A:
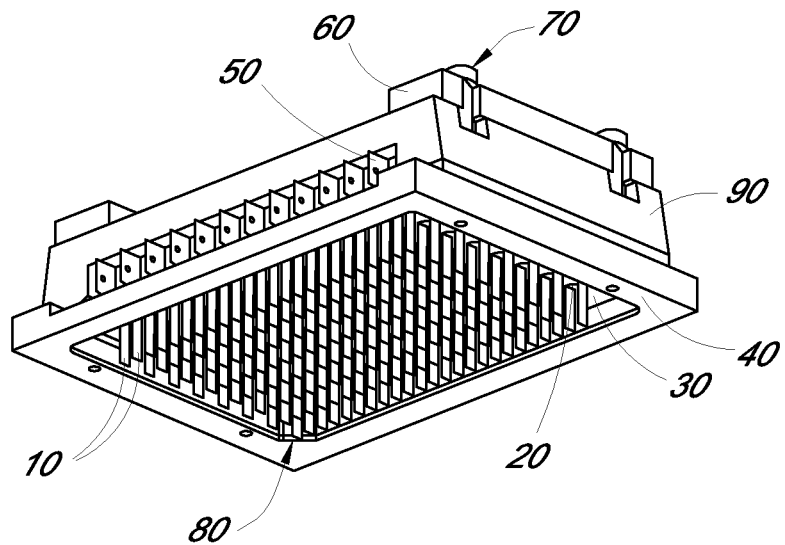
FIG. 1 Shows one embodiment of a dipper electrode array.

Generally, the nomenclature used herein and many of the fluorescence, computer, detection, chemistry and laboratory procedures described below are those well known and commonly employed in the art. Standard techniques are usually used for chemical synthesis, fluorescence, optics, molecular biology, computer software and integration. Generally, chemical reactions, cell assays and enzymatic reactions are performed according to the manufacturer's specifications where appropriate. The techniques and procedures are generally performed according to conventional methods in the art and various general references, including those listed below, which are herein incorporated by reference.

Lakowicz, J. R. *Topics in Fluorescence Spectroscopy*, (3 volumes) New York: Plenum Press (1991), and Lakowicz, J. R. *Emerging applications of fluorescence spectroscopy to cellular imaging: lifetime imaging, metal-ligand probes, multi-photon excitation and light quenching*. Scanning Microsc Suppl Vol. 10 (1996) pages 213-24, for fluorescence techniques;

Sambrook et al. *Molecular Cloning: A Laboratory Manual*, $2^{nd}$ ed. (1989) Cold Spring Harbor Laboratory Press, Cold Spring Harbor, N.Y., for molecular biology methods;

*Cells: A Laboratory Manual*, $1^{st}$ edition (1998) Cold Spring Harbor Laboratory Press, Cold Spring Harbor, N.Y., for cell biology methods;

*Optics Guide* 5 Melles Griot® Irvine Calif., *Optical Waveguide Theory*, Snyder & Love published by Chapman & Hall for general optical methods;

Hille, B. *Ionic Channels of Excitable membranes*, Second Edition (1992) Sinauer Associates, Inc., Sunderland, Mass. for general electrophysiological methods and properties of ion channels.

Horowitz and Hill, *The Art of Electronics*, Second Edition (1989) Cambridge University Press, Cambridge, U.K. for electronic circuits.

The following definitions are set forth to illustrate and define the meaning and scope of the various terms used to describe the invention herein.

The term "activation" refers to the transition from a resting (non-conducting) state of an ion channel to the activated (conducting) state.

The term "activation threshold" refers to the lowest potential above which measurable opening of a channel occurs.

The term "anode" refers to an electrode when driven to a positive potential relative to earth by an external source.

The term "area of cellular stimulation" means the area defined by two electrodes that experiences significant electrical stimulation (typically 5 V/cm or higher) in which the cells of interest are located. Typically the area of cellular stimulation is larger than, of equal to, the area of observation. For standard 96-well based measurements the area of cellular stimulation is typically about 16 mm$^2$.

The term "area of observation" means the portion of the system over which a measurement is taken. The area of observation is typically an area of at least 0.5 mm$^2$ for multiwell plate based measurements.

The term "bioluminescent protein" refers to a protein capable of causing the emission of light through the catalysis of a chemical reaction. The term includes proteins that catalyze bioluminescent or chemiluminescent reactions, such as those causing the oxidation of luciferins. The term "bioluminescent protein" includes not only bioluminescent proteins that occur naturally, but also mutants that exhibit altered spectral or physical properties.

The term "biphasic" refers to a pulse with two parts, each with an opposite polarity.

The term "Boltzman function" refers to the sigmoidal (i.e. step-like) response function $$y(x) = y_0 + \frac{A}{1 + \exp\left(\frac{x - x_{50}}{\Delta x}\right)}.$$

Where:
y is the independent variable
$y_0$ is an adjustable parameter equal to the limit of the function as $x \to \infty$
A is an adjustable parameter equal to step size
$x_{50}$ is an adjustable parameter related to the midpoint of the step
$\Delta x$ is an adjustable parameter describing the width of the step The term "cathode" refers to an electrode when driven to a negative potential relative to earth by an external source.

The term "depolarize" means to cause the transmembrane potential of a cell to become closer to zero. In the case of cells that are normally at negative resting potentials, this term means that the transmembrane potential changes in a positive direction.

The term "effective concentration (50%)" or "$EC_{50}$" refers to the concentration at which a pharmacological compound has half the effectiveness compared to the maximal effectiveness at high concentrations of the compound.

The term "electrically excitable" refers to a cell or tissue that responds to a suprathreshold electrical stimulus by generating an action potential. Electrically excitable cells contain at least one voltage-dependent ion channel type generating an inward current and at least one ion channel type generating an outward current.

The term "electrical stimulation" means initiating a voltage change in cells using an extracellular current pulse.

The term "electrode" means a controllable conductive interface between an instrument and a test system.

The term "electropermeablization" refers to mild electroporation, in which the hydrated pores created through the membrane are only large enough to pass water molecules and small single-atom ions.

The term "electroporation" refers to a phenomenon in which the application of a large electric potential across the membrane of a cell results in dielectric breakdown of the membrane, and the creation of hydrated pathways through the membrane.

The term "fluorescent component" refers to a component capable of absorbing light and then re-emitting at least some fraction of that energy as light over time. The term includes discrete compounds, molecules, naturally fluorescent proteins and marco-molecular complexes or mixtures of fluorescent and non-fluorescent compounds or molecules. The term "fluorescent component" also includes components that exhibit long lived fluorescence decay such as lanthanide ions and lanthanide complexes with organic ligand sensitizers, that absorb light and then re-emit the energy over milliseconds.

The term "FRET" refers to fluorescence resonance energy transfer. For the purposes of this invention, FRET includes energy transfer processes that occur between two fluorescent components, a fluorescent component and a non-fluorescent component, a luminescent component and a fluorescent component and a luminescent component with a non-fluorescent component.

The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination.

The term "Hill function" refers to the sigmoidal (i.e. step-like) response function $$y(x) = y_c + \frac{A}{x_0^n + x^n}.$$

Where:
y is the independent variable
$y_0$ is an adjustable parameter equal to the limit of the function as $x \to \infty$
A is an adjustable parameter equal to step size
$x_0$ is an adjustable parameter related to the midpoint of the step
n is an adjustable parameter describing the steepness of the step The term "Hill coefficient" refers to the parameter n in the Hill function.

The term "hit" refers to a test compound that shows desired properties in an assay.

The term "homolog" refers to two sequences or parts thereof, that are greater than, or equal to 75% identical when optimally aligned using the ALIGN program. Homology or sequence identity refers to the following. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, 1972, volume 5, National Biomedical Research Foundation, pp. 101-110, and Supplement 2 to this volume, pp. 1-10.

The term "hyperpolarize" means to cause the transmembrane potential of a cell to move farther away from zero. In the case of cells that are normally at negative resting potentials, this term means that the transmembrane potential changes in a negative direction.

The term "inactivation" means that an ion channel moves into the inactivated state.

The term "inactivated" refers to a voltage-dependent ion channel in a particular non-conducting conformational state. Transitions into and out of the inactivated state are generally slow relative to transitions between other conformational states. The inactivated state is usually the preferred state at elevated transmembrane potentials. At low transmembrane potentials, the inactivated state is unstable and relaxes to the resting state.

The term "kernel" means a mathematical function intended to be convoluted with one or more other time-varying functions. In theory, the kernel can be any function that tends to zero as the independent variable tends to ±∞. In practice, the kernel can be any waveform that can programmed into an arbitrary wavefunction generator, or that can be generated by a computer-controlled digital to analog (D/A) converter.

The term "luminescent component" refers to a component capable of absorbing energy, such as electrical (e.g. Electro-luminescence), chemical (e.g. chemi-luminescence) or acoustic energy and then emitting at least some fraction of that energy as light over time. The term "component" includes discrete compounds, molecules, bioluminescent proteins and macro-molecular complexes or mixtures of luminescent and non-luminescent compounds or molecules that act to cause the emission of light.

The term "transmembrane potential modulator" refers to components capable of altering the resting or stimulated transmembrane potential of a cellular or sub-cellular compartment. The term includes discrete compounds, ion channels, receptors, pore forming proteins, or any combination of these components.

The term "membrane time constant" or "$\tau_M$" means the product of the membrane resistance ($R_M$) and capacitance ($C_M$).

The term "monophasic" refers to a pulse whose polarity does not change to the opposite polarity.

The term "naturally fluorescent protein" refers to a protein capable of forming a highly fluorescent, intrinsic chromophore either through the cyclization and oxidation of internal amino acids within the protein or via the enzymatic addition of a fluorescent co-factor. The term includes wild-type fluorescent proteins and engineered mutants that exhibit altered spectral or physical properties. The term does not include proteins that exhibit weak fluorescence by virtue only of the fluorescence contribution of non-modified tyrosine, tryptophan, histidine and phenylalanine groups within the protein. The term "naturally occurring" refers to a component produced by cells in the absence of artificial genetic or other modifications of those cells.

The term "Multiwell plate" refers to a two dimensional array of addressable wells located on a substantially flat surface. Multiwell plates may comprise any number of discrete addressable wells, and comprise addressable wells of any width or depth. Common examples of multiwell plates include 96 well plates, 384 well plates and 3456 well Nanoplates™.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

The term "polarized cell" means a cell with an electric potential difference across its cell membrane.

The term "rectification" means that the conductance is non-linear, with a preferred direction.

The term "release from inactivation" refers to the conversion of an inactivated closed channel, to a resting closed channel that is now capable of opening.

The term "repetitive" means to repeat at least twice.

The term "repolarize" means to cause the transmembrane potential of a cell to approach its resting potential.

The term "resting" or "resting state" refers to a voltage-dependent ion channel that is closed, but free from inactivation.

The term "resting potential" for a cell means the equilibrium transmembrane potential of a cell when not subjected to external influences.

The term "reversal potential" for a particular ion refers to the transmembrane potential for which the inward and outward fluxes of that ion are equal.

The term "substantially parallel" means that the distance between the surfaces of two objects facing each other varies by less than 10%, preferably less than 5%, when measured at every point on the relevant surface of each object.

The term "targetable" refers to a component that has the ability to be localized to a specific location under certain conditions. For example, a protein that can exist at two or more locations that has the ability to translocate to a defined site under some condition(s) is targetable to that site. Common examples include the translocation of protein kinase C to the plasma membrane upon cellular activation, and the binding of SH2 domain containing proteins to phosphorylated tyrosine residues. The term includes components that are persistently associated with one specific location or site, under most conditions.

The term "threshold electroporation potential" refers to the externally applied field strength above which detectable electroporation of a living cell occurs.

The term "test compound" refers to a chemical to be tested by one or more screening method(s) of the invention as a putative modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.01 micromolar, 1 micromolar and 10 micromolar. Test compound controls can include the measurement of a signal in the absence of the test compound or comparison to a compound known to modulate the target.

The term "transformed" refers to a cell into which (or into an ancestor of which) has been introduced, by means of recombinant nucleic acid techniques, a heterologous nucleic acid molecule.

The term "transgenic" is used to describe an organism that includes exogenous genetic material within all of its cells. The term includes any organism whose genome has been altered by in vitro manipulation of the early embryo or fertilized egg or by any transgenic technology to induce a specific gene knockout.

The term "transgene" refers any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes of the invention include DNA sequences that encode the fluorescent or bioluminescent protein that may be expressed in a transgenic non-human animal.

The term "transistor-transistor logic" or "TTL" refers to an electronic logic system in which a voltage around +5V is TRUE and a voltage around 0V is FALSE.

A "uniform electric field" means that the electric field varies by no more than 15% from the mean intensity within the area of observation at any one time.

The term "voltage sensor" includes FRET based voltage sensors, electrochromic transmembrane potential dyes, transmembrane potential redistribution dyes, extracellular electrodes, field effect transistors, radioactive ions, ion sensitive fluorescent or luminescent dyes, and ion sensitive, fluorescent or luminescent proteins, that are capable of providing an indication of the transmembrane potential.

The following terms are used to describe the sequence relationships between two or more polynucleotides: "reference sequence", "comparison window", "sequence identity", "percentage identical to a sequence", and "substantial identity". A "reference sequence" is a defined sequence used as a basis for a sequence comparison; a reference sequence may be a subset of a larger sequence, for example, as a segment of a full-length cDNA or gene sequence, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage identical to a sequence" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 30 percent sequence identity, preferably at least 50 to 60 percent sequence identity, more usually at least 60 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least 30 percent sequence identity, preferably at least 40 percent sequence identity, more preferably at least 50 percent sequence identity, and most preferably at least 60 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

1. Introduction

The present invention recognizes for the first time that the transmembrane potentials of intact living cells comprising at least one voltage regulated ion channel, can be precisely modulated via the application of repetitive electrical stimulation pulses to the fluid bathing the cells. The present invention includes instrumentation and methods that provide for the accurate and reliable modulation of the transmembrane potentials of intact living cells without significantly disrupting their native cellular integrity.

As a non-limiting introduction to the breadth of the invention, the invention includes several general and useful aspects, including:

1) Instrumentation including electrodes, and electrode arrays for reliably generating uniform electrical fields in cultures of living cells in aqueous solution.

2) Multiwell plates comprising surface electrodes for high throughput and miniaturized stimulation and analysis of ion channel or cellular activities.

3) Systems for high throughput analysis of ion channel and cellular activities and for use in drug discovery, analysis, screening and profiling.

4) Methods for modulating the transmembrane potential of a living cell via the use of repetitive electrical stimulation.

5) Methods for screening the effects of test compounds on the activities of voltage regulated, and non-voltage regulated ion channels, transporters and leak currents. Including determining state-dependent pharmacological activity of compounds against ion channel and transporter proteins.

6) Methods for profiling and selecting cells or clones based on their response to electrical stimulation.

7) Methods for quantitative determination of cellular and ion channel parameters in a high-throughput manner, and for quantification of the pharmacological effects of compounds on those parameters.

8) Methods for the introduction of exogenous compounds into the intracellular spaces of cells.

9) Methods for modulating the transmembrane potential of intracellular organelles, and for screening test compounds against ion channels in these organelles.

10) Methods for characterizing the physiological effect of the transmembrane potential on the function and regulation of physiological and biochemical responses, including gene expression, enzyme function, protein activity and ligand binding.

11) Methods for programming or training adaptive neuronal networks or bio-computers for specific functional or logical responses.

12) Methods for providing efficient neuronal interfaces for prosthetic devices implanted into an animal, including a human.

These aspects of the invention and others described herein, can be achieved by using the methods and instrumentation described herein. To gain a full appreciation of the scope of the invention, it will be further recognized that various aspects of the invention can be combined to make desirable embodiments of the invention. Such combinations result in particularly useful and robust embodiments of the invention.

2. Electrodes and Electrode Arrays

In one embodiment, the present invention includes electrodes, and electrode arrays, for creating electrical fields across the area of observation. Typically this is achieved via the use of a pair of electrically conductive electrodes. An important design feature is that the electrode pairs create well-defined electrical fields. Preferred electrode designs include electrode configurations that maximize the electric field homogeneity experienced by the cells under observation.

Generating uniform electric fields over the area of observation is important for electrical stimulation for several reasons. Firstly, because the cellular response is sensitive to the magnitude of the local electric field, non-uniform fields typically cause non-uniform responses in different areas, leading to an increased scatter in the results. Secondly, the threshold for electropermeablization is typically only a factor of 2-5 larger than the transmembrane potentials required for electrical stimulation membrane (see Teissie and Rols, 1993, Biophys. J. 65:409-413). Thus, if the electric field is too non-uniform, it may not be possible to stimulate all the cells in the area of observation without also electropermeablizing some of them.

Field uniformity over a fixed area can be described in two ways: (1) the standard deviation of the field magnitude divided by the average field magnitude in the area, and (2) the difference between the highest and lowest field magnitudes, normalized to the average field magnitude in the area.

a. Design of Electrodes

The simplest way to generate a uniform electric field in a conductive medium is to use two identical, flat electrodes with surfaces that are aligned substantially parallel to each other. Generally the closer the electrodes are to each other relative to their width in the transverse direction, the greater the field uniformity will be. Typical round multiwell plate wells however limit the width of electrodes that can be inserted into the wells, and also introduce two other effects which reduce field uniformity.

The roundness of the wells provides a challenge to create a uniform field pointing in one direction with two electrodes the width of the conductive saline between the electrodes is constantly changing. Additionally the high surface tension of water generates variations in the height of the saline across the well when dipper electrodes are inserted. The curved surface, or meniscus, can perturb the electric field throughout the volume of the well. The depth of 100 μL of saline in a 96-well plate is normally about 3.0 mm deep at the center and about 2.9 mm deep at the edges of the well. When two stainless steel parallel plate electrodes are inserted, saline is drawn up between the electrodes and the walls of the well causing depth variations over the area of observation suggesting that the current paths throughout the volume of the saline curve around the center, generating electric field non-uniformity.

In one aspect the present invention includes improved electrode designs, and systems for electrical stimulation that address these issues to create substantially uniform electrical fields over the area of observation.

In one embodiment, (FIG. 9A) the electrode pair comprises two substantially parallel electrodes comprising an electrical insulator that is attached to the pair of electrodes to restrict current flow to a defined region thereby creating a highly uniform electrical field.

In another embodiment, (FIG. 9B) the electrode pair additionally comprises satellite electrodes to create a more uniform electrical field.

In another embodiment, (FIG. 9D) the electrode pair is sub-divided into several pieces separated by thin insulating dividers. In this case the potential applied to each electrode, expressed as a fraction of the potential applied to the central most piece can be individually tuned to maximize the field uniformity in the area of observation.

In another aspect, the present invention includes improved electrode designs (FIG. 9C) that exhibit improved field uniformity over the area of observation via the elimination or reduction of the meniscus effect.

In another aspect multiple electric potential sensors can be fabricated into the surface or walls of the wells in a multiwell plate, or attached in arrays to the dipper electrode assembly. These sensors can be monitored to manually or automatically adjust the individual electrodes, so as to maximize field uniformity. This arrangement will be useful to allow a stimulating electrode array to compensate for variations and imperfections in the well shape, volume of saline, variations in the manufacturing process for the electrodes, damage to the electrode assembly, etc.

b. Placement of Electrodes within the Wells

For dipper electrodes, the ideal situation (in terms of creating a uniform electric field) would be to have the bottoms of the electrodes touching the bottom of the well. This way, there will be no fringing fields or field non-uniformity associated with vertical current paths. For a removable structure, however, it is not desirable to require the electrodes to make contact with the surface. Small deviations in the plate geometry can cause some electrodes to press into the surface, causing damage either to the plate, the cells, or the electrodes. Additionally, in some wells, the electrodes may not extend all the way to the surface. For these reasons it may be desirable to design a small gap between the bottom of the electrode and the bottom of the well.

Accordingly in one aspect the present invention includes multiwell plates in which the area of observation in the middle of the well is raised relative to area around the circumference of the well, where the electrodes would be placed.

The fringing fields will cause non-uniformity over an inter-electrode distance roughly equal to the gap between the bottom of the electrode and the bottom of the well. Therefore, this gap should be kept as small as is practical, preferably in the range of 0.1 to 0.5 mm and the area of observation should not typically include any part of the well within this distance from the electrodes.

c. Manufacture of Electrodes

Any electrically conductive material can be used as an electrode. Preferred electrode materials have many of the following properties, (1) they do not corrode in saline, (2) they do not produce or release toxic ions, (3) they are flexible and strong, (4) they are relatively inexpensive to fabricate, (5) they are non porous, and (6) they are easily cleaned. Preferred materials include noble metals (including gold, platinum, and palladium), refractory metals (including titanium, tungsten, molybdenum, and iridium), corrosion-resistant alloys (including stainless steel) and carbon or other organic conductors (including graphite and polypyrrole). For many embodiments stainless steel provides a preferred electrode material. This material is inexpensive, easy to machine, and very inert in saline. Stainless steel oxidizes slowly to produce iron oxide when passing current in saline, but this does not appear to affect the performance of the system. Iron oxide has very low solubility in water and toxic levels of iron do not appear to be released. Additionally any iron oxide deposits can easily be removed by soaking the electrodes in 10% nitric acid in water for two hours, then rinsing thoroughly with distilled water.

Solid copper and silver electrodes may be used for some applications but are less preferred for routine use because they corrode rapidly in saline. Gold plated copper electrodes are relatively inert, but appear to lose their gold plating during prolonged electrical stimulation.

Electrolysis products can be contained or eliminated by coating the surfaces of the electrodes with protective coatings, such as gelatin, polyacrilimide, or agarose gels. Another potentially useful electrode material is an electrochemical half-cell, such as a silver/silver chloride electrode.

d. Electrode Arrays

Dipper electrodes typically consist of one or more pairs of electrodes that are arranged in an array that can be retractably moved into, and out of, one or more wells of a multiwell plate. Dipper electrodes may be orientated into arrays that match the plate format and density, but can be in arrays of any configuration or orientation. For example for a standard 96 well plate, a number of electrode configurations are possible including electrode array arrangements to selectively excite one or more columns, or rows, simultaneously.

Figure 1B:
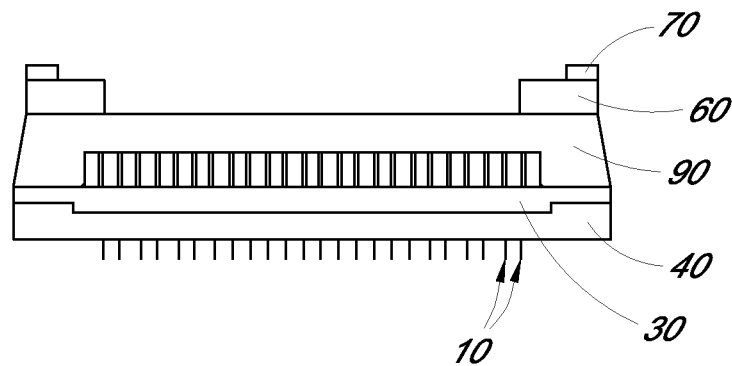
Figure 1C:
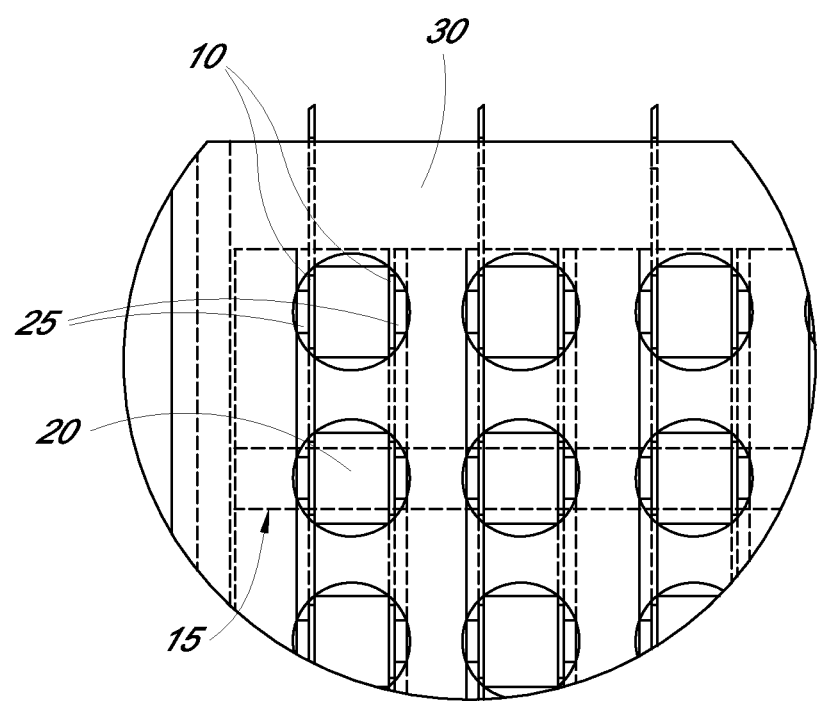

An example of one embodiment of an electrode array of this type is shown in FIG. 1. In this example, a 12 by 8 array of electrode pairs is formatted so as to fit into a standard 96-well multiwell plate. In this case the electrodes (10) are approximately 4 mm wide, 1 cm long and 0.2 mm thick, and extend from a conductive comb (50) that is connected through a switch to one side of the output stage of a high-power function generator. The electrodes are mounted parallel to each other, 4 mm apart, with a non-conductive nylon spacer (20) in between. In this case, the switch (330) enables one column of the 96 well plate to be selectively stimulated at a time, however any temporal, or spatial, combination of stimulation protocols is potentially possible given the appropriate configuration of switching, wiring and power function generator.

The entire array of electrodes is held in correct registration by a rigid non conductive member (30) that keeps each electrode pair correctly spaced to accurately match a standard 96 well plate layout. The non-conductive member (30) provides for the electrodes to move up or down while precisely maintaining their registration with the multiwell plate.

To provide for correct registration of the electrode array with a multiwell plate, the electrode assembly can optionally comprise an outer border or flange (40) that can accommodate a standard 96-well plate, and enables accurate plate registration. In some embodiments the border (40) can further include a registration notch or indentation (80) to provide unambiguous plate registration.

In a preferred embodiment (Also shown in FIG. 1A) the electrode array further comprises means for retractably inserting the electrode array into the wells of the multiwell plate. In one embodiment of this configuration, the electrode array further comprises an upper, movable support member (90) to which the electrodes (10) are attached. The movable support member (90) is able to move up or down relative to the non-conductive member (30) by sliding on four alignment pins (70). Not shown in these figures is a spring that enables the movable support layer (90) to automatically return to the upper position when downward force is no longer applied. A spacer (60) provides the ability to lock the movable support layer (90) and electrodes (10) in the fully lower orientation. This device allows the electrical stimulator to be used in manual and/or robotic screening modes.

3. Multiwell Plates for Electrical Stimulation

The multiwell plates of the present invention are designed primarily to provide for efficient electrical stimulation of cells while at the same time enabling the optical analysis of transmembrane potential changes. To accomplish this conductive surface electrodes may be orientated in, or on, the walls, bottoms or lids of the multiwell plate. In general such multiwell plates can have a footprint of any shape or size, such as square, rectangular, circular, oblong, triangular, kidney, or other geometric or non-geometric shape. The footprint can have a shape that is substantially similar to the footprint of existing multiwell plates, such as the standard 96-well microtiter plate, whose footprint is approximately 85.5 mm in width by 127.75 mm in length, or other sizes that represent a current or future industry standard (see T. Astle, Standards in Robotics and Instrumentation, J. of Biomolecular Screening, Vol. 1 pages 163-168, 1996). Multiwell plates of the present invention having this footprint can be compatible with robotics and instrumentation, such as multiwell plate translocators and readers as they are known in the art.

Typically, wells will be arranged in two-dimensional linear arrays on the multiwell plate. However, the wells can be provided in any type of array, such as geometric or non-geometric arrays. The multiwell plate can comprise any number of wells. Larger numbers of wells or increased well density can also be easily accommodated using the methods of the claimed invention. Commonly used numbers of wells include 6, 12, 96, 384, 1536, 3456, and 9600.

Well volumes typically can vary depending on well depth and cross sectional area. Preferably, the well volume is between about 0.1 microliters and 500 microliters.

Wells can be made in any cross sectional shape (in plan view) including, square, round, hexagonal, other geometric or non-geometric shapes, and combinations (intra-well and inter-well) thereof. Preferred are square or round wells, with flat bottoms.

The walls can be chamfered (e.g. having a draft angle). Preferably, the angle is between about 1 and 10 degrees, more preferably between about 2 and 8 degrees, and most preferable between about 3 and 5 degrees.

The wells can be placed in a configuration so that the well center-to well-center distance can be between about 0.5 millimeters and about 100 millimeters. The wells can be placed in any configuration, such as a linear-linear array, or geometric patterns, such as hexagonal patterns. The well-to-well distance can be about 9 mm for a 96 well plate. Smaller well-center to well-center distances are preferred for smaller volumes.

The wells can have a depth between about 0.5 and 100 millimeters. Preferably, the well depth is between about 1 millimeter and 100 millimeters, more preferably between about 2 millimeters and 50 millimeters, and most preferably between about 3 millimeters and 20 millimeters.

The wells can have a diameter (when the wells are circular) or maximal diagonal distance (when the wells are not circular) between about 0.2 and 100 millimeters. Preferably, the well diameter is between about 0.5 and 100 millimeters, more preferably between about 1 and 50 millimeters, and most preferably, between about 2 and 20 millimeters.

The multiwell plate, will generally be composed of electrically non-conductive material and can comprise an optically opaque material that can interfere with the transmission of radiation, such as light, through the wall of a well or bottom of a well. Such optically opaque materials can reduce the background associated with optical detection methods. Optically opaque materials can be any known in the art or later developed, such as dyes, pigments or carbon black. The optically opaque material can prevent radiation from passing from one well to another, to prevent cross-talk between wells, so that the sensitivity and accuracy of the assay is increased. The optically opaque material can also be reflective, such as those known in the art, such as thin metal layers, mirror coatings, or mirror polish. Optically opaque materials can be coated onto any surface of the multiwell plate, or be an integral part of the plate or bottom as they are manufactured. Optically opaque material can prevent the transmittance of between about 100% to about 50% of incident light, preferably between about 80% and greater than 95%, more preferably greater than 99%.

Since most measurements will not typically require light to pass through the wall of the well, materials such as polymers can include pigments to darken well walls or absorb light. Such application of pigments will help reduce background fluorescence. Pigments can be introduced by any means known in the art, such as coating or mixing during the manufacture of the material or multiwell plate. Pigment selection can be based on a mixture of pigments to dampen all background inherent to the polymer, or a single pigment or ensemble of pigments selected to filter or absorb light at desired wavelengths. Pigments can include carbon black.

Surface electrodes can be embedded or otherwise attached to the wall in a variety of formats and arrangements, for example as several narrow vertical electrode stripes. By appropriately tuning the relative potentials of each stripe, uniform electric fields can be generated in the area of observation. Further, using a circular insert, or by embedding vertical stripe electrodes all around the well, uniform electrical fields can be generated in any direction across the well. It would also be possible to create a uniform field in one direction, followed by a uniform field in another direction. This could be useful for cell types whose electrical characteristics are anisotropic, such as neural or muscle cells, or for cell types with large aspect ratios.

Each well also comprises a bottom having a high transmittance portion and having less fluorescence than a polystyrene-bottom of at least about 90 percent of said bottom's thickness. This property can be determined by comparing the fluorescence of an appropriate control bottom material with the fluorescence of a test material. These procedures can be performed using well known methods. Preferably, the bottom is a plate or film as these terms are known in the art. The thickness of the bottom can vary depending on the overall properties required of the plate bottom that may be dictated by a particular application. Such properties include the amount of intrinsic fluorescence, rigidity, breaking strength, and manufacturing requirements relating to the material used in the plate. Well bottom layers typically have a thickness between about 10 micrometers and about 1000 micrometers. Preferably, the well bottom has a thickness between about 10 micrometers and 450 micrometers, more preferably between about 15 micrometers and 300 micrometers, and most preferably between about 20 micrometers and 100 micrometers.

The bottom of a well can have a high transmittance portion, typically meaning that either all or a portion of the bottom of a well can transmit light. The bottom can have an optically opaque portion and a high transmittance portion of any shape, such as circular, square, rectangular, kidney shaped, polygonal, or other geometric or non-geometric shape or combinations thereof.

Preferably, the bottom of the multiwell plate can be substantially flat, e.g. having a surface texture between about 0.001 mm and 2 mm, preferably between about 0.01 mm and 0.1 mm (see, Surface Roughness, Waviness, and Lay, Am. Soc. of Mech. Eng. #ANSI ASME B46.1-2985 (1986)). If the bottom is not substantially flat, then the optical quality of the bottom and wells can decrease because of altered optical and physical properties of one or both.

For surface electrode embodiments, the bottom will preferably comprise strips of electrically conductive material or coatings that overlap the edge of the wells of the multiwell plate and are in electrical contact with the contents of the wells. The electrically conductive strips will typically terminate at electrical connectors to enable facile attachment to the output stage of a high-power function generator as described previously. The electrically conductive strips should have low enough resistance so that they can carry the stimulating currents without excessive loss in voltage over their length. The resistance from the connector end to the farthest well end should be less than 10Ω, and more preferably less than 1Ω, and more preferably still less than 0.1Ω. The cross-sectional area of the electrically conductive strips should be large enough to accomplish the resistance requirement. For commonly employed electrical conductors, this cross sectional area should be at least $10^{-4}$ mm$^2$, and more preferable at least $10^{-3}$ mm$^2$.

In practice, any conductive materials could be used as long as they are capped with a conductive material that is inert in saline. Such materials include the noble metals (including gold, platinum, and palladium) and the refractory metals (including chromium, molybdenum, iridium, tungsten, tantalum, and titanium) as well as alloys thereof. Preferred materials for the conductive material for surface electrodes include combinations of chromium, copper, gold, and indium-tin-oxide that can be readily embedded or electroplated into or on the transparent bottom layer. Electrolysis products can be contained or eliminated by coating the surfaces of the electrodes with protective coatings, such as gelatin, polyacrilimide, or agarose gels.

Another potentially useful electrode material is an electrochemical half-cell, such as a silver/silver chloride electrode.

The electrically conductive material coatings or surface modifications can be introduced into the bottom using any suitable method known in the art, including vacuum deposition, electroplating, printing, spraying, radiant energy, ionization techniques or dipping. Surface modifications can also be introduced by appropriately derivatizing a polymer or other material, such as glass or quartz, before, during, or after the multiwell plate is manufactured and by including an appropriate derivatized polymer or other material in the bottom layer. The derivatized polymer or other material can then be reacted with a chemical moiety that is used in an application of the plate. Prior to reaction with a chemical moiety, such polymer or other material can then provide either covalent or non-covalent attachment sites on the polymer or other material. Such sites in or on the polymer or other material surface can be used to attach conductive layers to the plates. Examples of derivatized polymers or other materials include those described by U.S. Pat. No. 5,583,211 (Coassin et al.) and others known in the art or later developed.

a. Materials and Manufacturing

The materials for manufacturing the multiwell plate will typically be polymeric, since these materials lend themselves to mass manufacturing techniques. However, other materials can be used to make the bottom of the multiwell plate, such as glass or quartz. The bottom can be made of the same or different materials and the bottom can comprise polystyrene, or another material. Preferably, polymers are selected that have low fluorescence and or high transmittance. Polymeric materials can particularly facilitate plate manufacture by molding methods known in the art and developed in the future, such as insert or injection molding.

The multiwell plate of the present invention can be made of one or more pieces. For example, the plate and bottom can be made as one discrete piece. Alternatively, the plate can be one discrete piece, and the bottom can be a second discrete piece, which are combined to form a multiwell plate. In this instance, the plate and bottom can be attached to each other by sealing means, such as adhesives, sonic welding, heat welding, melting, insert injection molding or other means known in the art or later developed. The plate and bottom can be made of the same or different material. For example, the plate can be made of a polymer, and the bottom made of polystyrene, cycloolefin, Aclar, glass, or quartz.

Miniaturized surface electrode designs are feasible in standard plate formats (96, 384, 1536) as well as 3456 and higher plate densities. The throughput of such systems is potentially extremely high. For example, assuming 3456 wells per plate screened at 30 plates per hour corresponds to an overall throughput of approximately 800,000 wells per eight-hour day, which is approximately 8 times faster than is presently available, assuming equal plate read times.

Figure 2A:
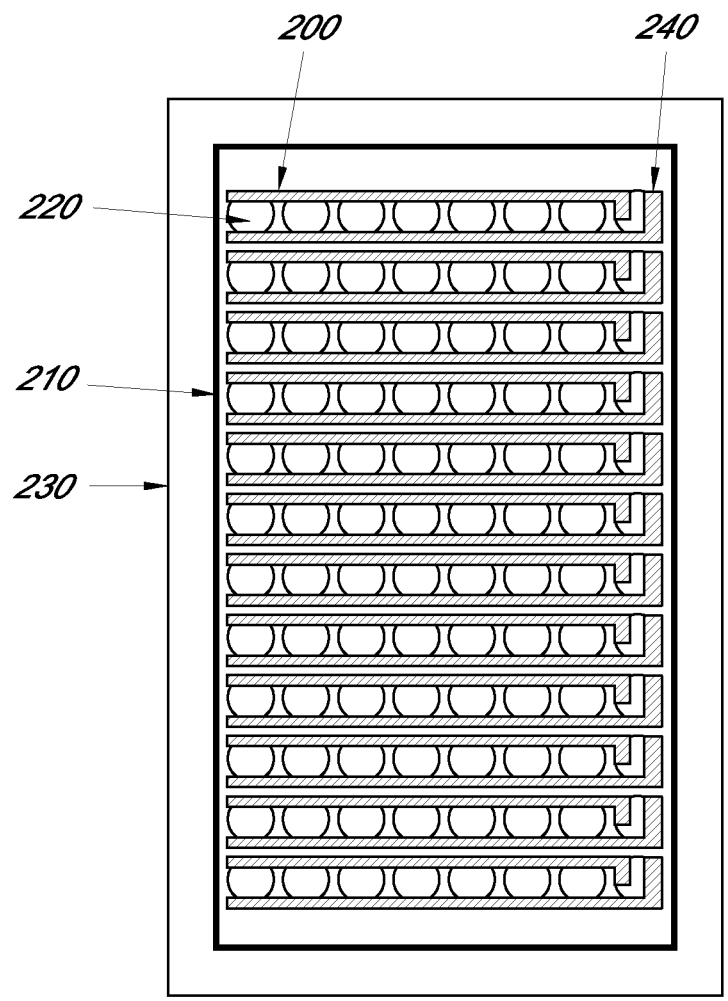
FIG. 2 Shows a number of embodiments of multiwell plates comprising surface electrodes.

An example of one embodiment of multiwell plate with surface electrodes is shown in FIG. 2A. In this example, pairs of conductive strips (200) are attached in parallel to an optically transparent bottom layer (210) such as glass, or plastic such as COC (see U.S. Pat. No. 5,910,287, issued Jun. 8, 1999) in a 96-well plate format. In this example, the strips of conductive material (200) are approximately 2 mm wide, 10 µm thick, and separated by distance of approximately 4 mm to enable optical analysis of the cells located in the wells (220), between the electrodes through the optically transparent bottom layer (210). In other embodiments the strips of conductive material can comprise stainless steel wires (from about 0.001" to about 0.010" diameter). The optically transparent bottom layer (210) is attached to a 96-well multiwell plate array (230) and replaces the normal plate bottom. The strips of electrically conductive material (200) overlap the edge of the wells (220) of the 96-well multiwell plate and are in electrical contact with the contents of the wells. The electrically conductive strips (200) terminate at electrical contacts (240) to enable facile attachment to the output stage of a high-power function generator as described previously. In this example, there are two electrode contacts per eight-well column in the first well of the column. This permits the use of standard 96-well plate layouts, for simpler handling during cell culturing. No cells or saline are inserted into these wells. This design permits the simultaneous stimulation of seven wells in a single column. During the assay, the operator or a robot will temporarily attach wires to the contacts, for example with push-pin test electrodes.

Figure 2B:
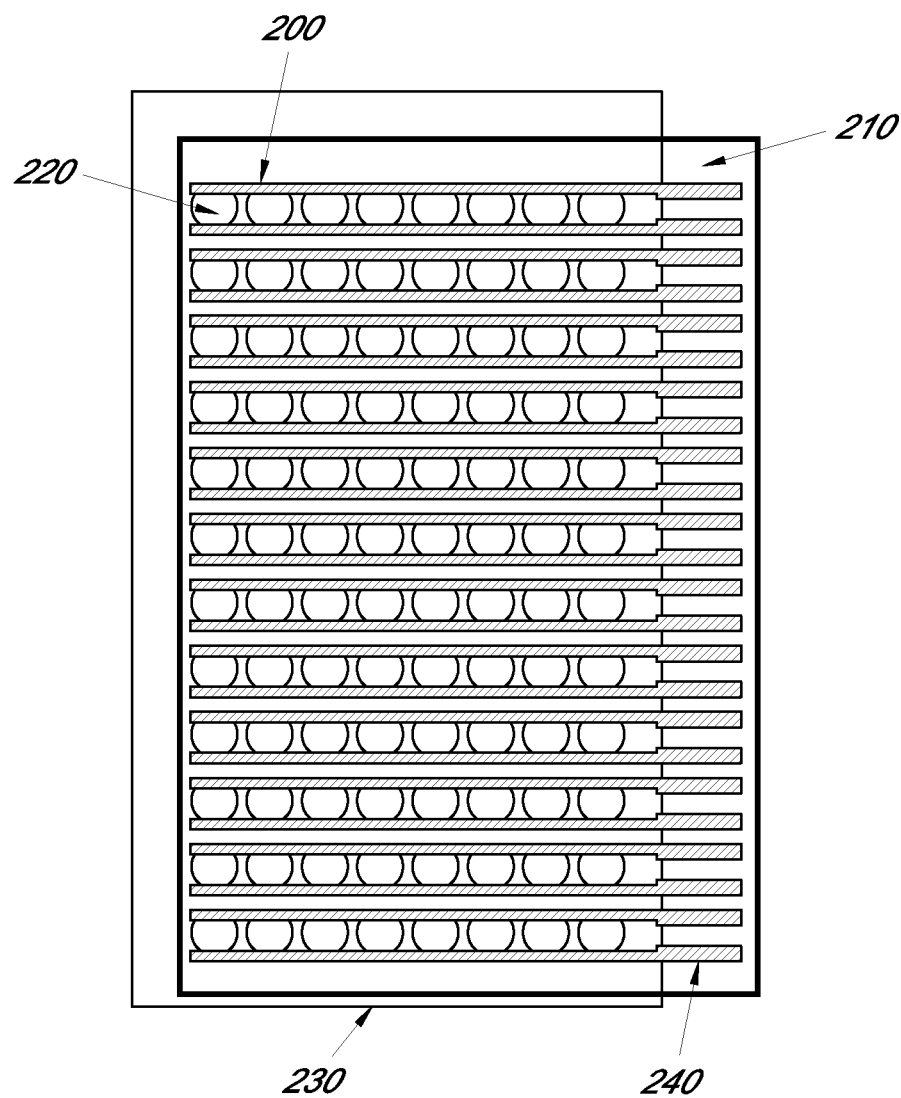

Another embodiment of a multwell plate with surface electrodes is shown in FIG. 2b. In this embodiment, the transparent bottom layer (210) extends beyond the edge of the multiwell plate (230). In this configuration, all wells remain available for use with cells and compounds. Further, attachment of external wiring to the contacts (240) is simplified. Push-pin contacts, circuit-board edge connectors, or zero-insertion force sockets can be used to make contact with the electrodes. The extended bottom layer (210) may make the plates less convenient to manipulate during routine use. This can be remedied by bringing the electrode traces (200) to the reverse side of the bottom layer (210) during the manufacturing process. This can be accomplished by several methods. For example, using two-sided processing of the plates to create contact areas, through-holes can be made and electroplated, or conducting traces can be wrapped around the edge of the bottom layer. As another example, the bottom layer can be made of a flexible insulating material. Then, after making the structure as shown in FIG. 2B, the part of the bottom layer which protrudes from the edge of the plate can be folded and attached to the underside of the plate.

Figure 2C:
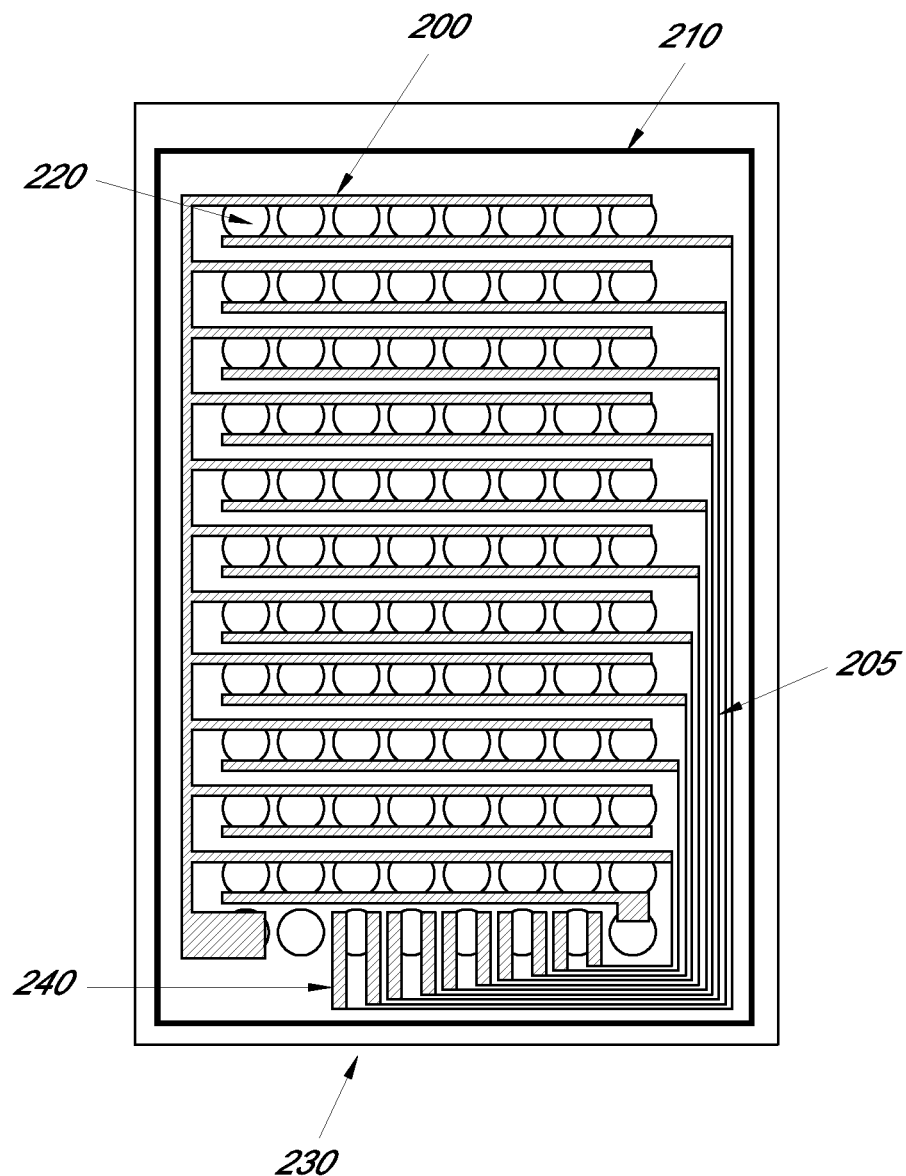

Another embodiment of a multwell plate with surface electrodes is shown in FIG. 2C. In this embodiment, the electrodes (200) are attached to the contact pads (240) with narrow via wires (205). This permits the use of standard 96-well plate layouts, for simpler handling during cell culturing. In this embodiment, all of the electrodes of one polarity are shorted together. Selection of a single column is accomplished by supplying the current pulse to only one electrode of the other polarity. In this embodiment, no cells, saline, or compounds are placed into the final column where the contact pads are. During the assay, the operator or a robot will temporarily attach wires to the contacts, for example with push-pin test electrodes.

Figure 2D:
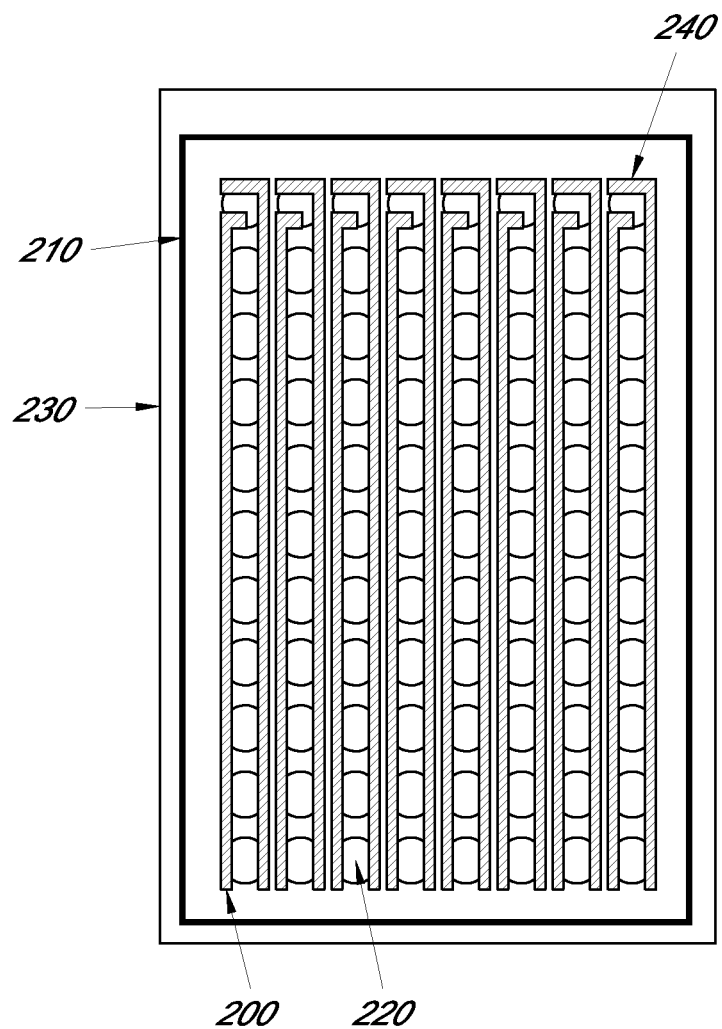

Another embodiment of a multwell plate with surface electrodes is shown in FIG. 2D. In this embodiment, the electrodes (200) are aligned parallel to the longer dimension of the 96-well plate. This design is essentially similar to the design shown in FIG. 2A, with the exception that eleven wells in a row will be simultaneously stimulated.

Preferred materials for the conductive material for surface electrodes include combinations of chromium, copper, gold, and indium-tin-oxide that can be readily embedded, attached, or electroplated into or on the transparent bottom layer. In practice, any conductive materials could be used as long as they are capped with a conductive material that is inert in saline. Such inert materials include the noble metals (including gold, platinum, and palladium), the refractory metals (including chromium, molybdenum, iridium, tungsten, tantalum, and titanium), corrosion-resistant alloys (including stainless steel), and carbon or other organic conductors (including graphite and polypyrrole) as well as combinations or alloys of these materials.

4. Systems for Electrical Stimulation and Spectroscopic Measurement

The present invention includes systems for automated electrical stimulation and spectroscopic measurement, comprising: at least one electrode assembly, a means for electrical stimulation, an optical detector, and computer control means to coordinate the generation of electrical stimuli, collection of data and movement of multiwell plates. The system can further comprise means for fluid addition. In one aspect these systems are designed for modulating, characterizing and assaying the activity of ion channels, transporters, leak currents present in or on the surfaces of living cells, and for rapidly screening for the effects of test compounds on the effects of channel or cellular activities. The present invention is also directed to chemical entities and information (e.g., modulators or chemical or biological activities of chemicals) generated or discovered by operation of workstations of the present invention.

Figure 3:
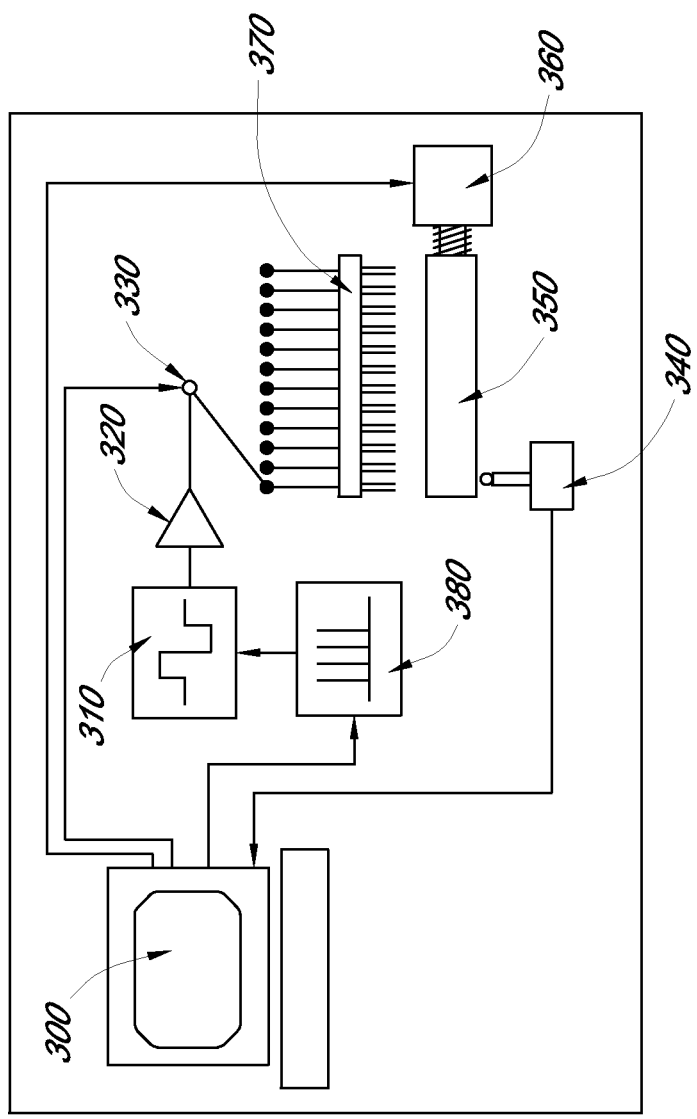
FIG. 3 Shows a block diagram of one embodiment of the electrical stimulation system.

FIG. 3 shows a block diagram of the major electrical and optical components for one embodiment of a system for automated electrical stimulation and spectroscopic measurement. In this example a 96-well multiwell plate dipper electrode array (FIG. 1) was used for electrical stimulation. In addition to the stimulator electrode array, the system has several additional electrical, optical and mechanical components, as described in detail in commonly owned U.S. patent application Ser. No. 09/118,728, filed Jul. 24, 1998.

In this embodiment, a National Instruments (Austin, Tex.) PC-DIO 24 digital input/output card on board the computer (300) is used to set the proper channel on a 1-to-12 switch (330) (National Instruments ER-16). The computer controlling the fluorescent plate reader (300) also sends out a TTL signal to trigger the function generators (310) when the stimulus is programmed to begin. Stimulus signals are generated by two arbitrary waveform generators (310). The function generators are Tektronix (Beaverton, Oreg.) model number AFG310. The first triggers a series of TTL pulses to the second which is programmed with the individual stimulus waveform. More complex waveform trains can be generated by connecting multiple waveform generators in series and/or in parallel. These waveform generators would be triggered by the computer-generated TTL pulse or by each other. Alternatively, an A/D converter or a sound card on board the computer could be used to generate a train of stimuli. In this case, commercially-available or custom software could be used to program the waveform train, or to change the waveform during the train.

The train of stimuli is sent through a high-power amplifier (320), through the switch (330), and into the stimulator head (370). In this case the amplifier was built using the APEX PA93 chip (Apex Microtechnology Corp, Tucson, Ariz.) following a circuit provided by the manufacturer. Preferred amplifiers for the present application would typically meet, or exceed the following specifications: ±100V DC in, 100 GΩ input impedance, 20× voltage gain, ±90V out, ±3 A out, 10Ω output impedance.

The majority of current passes through the saline between the electrodes, typically in a single eight-well column of the microtiter plate (350) at a time. Excitation light at 400±7.5 nm illuminates the stained cells from below, and emitted fluorescent light is measured at two wavelengths via the detector module (340) blue at 460±20 nm and orange at 580±30 nm; (see González et al., Drug Discovery Today 4: 431-439, 1999). Once a column of cells has been stimulated the computer (300) triggers the motor (360) to move the multiwell plate (350) to a new position ready for the next stimulation.

For a typical 96-well multiwell plate the electrodes are 4 mm wide with a gap (g) of 4 mm. Stimulation is usually performed in a volume of 100 µL of physiological saline in the well. With this volume of saline, the depth averages approximately 3.0 mm (this depth varies by as much as 20% across the well due to the meniscus effect). The electrodes rest approximately 0.5 mm off the bottom of the wells. The electric field (E) applied across the cells is estimated as the voltage across the electrodes ($V_0$) divided by the electrode gap (g), $E=V_0/g$. This is an overestimate of the actual field because of the influence of electrochemical reactions at each electrode which consume approximately 1.5 V. In the typical voltage ranges used for stimulation (10 to 60 V/cm), this overestimate is on the order of approximately 10%. Accurate measurement and calibration of the field can be performed by mapping the electric potential in the well when current is passed.

The present invention also includes automated workstations that are programmably controlled to minimize processing times at each workstation and that can be integrated to minimize the processing time of the liquid samples for electrical stimulation and analysis.

Typically, a system of the present invention would include one or more of the following: A) a storage and retrieval module comprising storage locations for storing a plurality of chemicals in solution in addressable chemical wells, a chemical well retriever and having programmable selection and retrieval of the addressable chemical wells and having a storage capacity for at least 100,000 addressable wells, B) a sample distribution module comprising a liquid handler to aspirate or dispense solutions from selected addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared), C) a sample transporter to transport the selected addressable chemical wells to the sample distribution module and optionally having programmable control of transport of the selected addressable chemical wells (including adaptive routing and parallel processing), D) a system for automated washing, staining, and timed incubation of cells in multiwell plates, E) a system for automatically transporting cell plates and test compound plates between the various workstations, F) a system for automated electrical stimulation and spectroscopic measurement, and a data processing and integration module, G) a master control system which co-ordinates the activities of any of the above subsystems.

The storage and retrieval module, the sample distribution module, and the system for automated electrical stimulation and spectroscopic measurement are integrated and programmably controlled by the data processing and integration module. The storage and retrieval module, the sample distribution module, the sample transporter, the system for automated electrical stimulation and spectroscopic measurement and the data processing and integration module are operably linked to facilitate rapid processing of the addressable sample wells. Typically, devices of the invention can process at least 100,000 addressable wells in 24 hours. This type of system is described in U.S. Pat. No. 5,985,214, issued Nov. 16, 1999, which is incorporated herein by reference.

a. Microfluidic Systems

The present invention also includes the use of electrodes that have been incorporated into microfluidic chips and which provide for highly miniaturized electrical stimulation and analysis. Such systems include those, for example, described in U.S. Pat. No. 5,800,690 issued Sep. 1, 1998 to Chow et al., European patent application EP 0 810 438 A2 filed May 5, 1997, by Pelc et al. and PCT application WO 98/00231 filed 24 Jun. 1997 by Parce et al. These systems typically use electrogenic fluid movement to manipulate small fluid volumes within microcapillaries present on glass or silicon chips. These microfluidic chip based analysis systems can provide massively parallel miniaturized analysis. Such systems are preferred systems of spectroscopic measurements in some instances that require miniaturized analysis.

For example, the microfabricated fluorescence-activated cell sorter described by Fu et al. (Nature Biotechnology 17: 1109-11, 1999) could be easily modified to have a pair of electrodes placed in, or near the optical interrogation region. Using the methods described herein, individual cells could be electrically stimulated and individually sorted based on their response to the stimulation. This method would greatly simplify the process of obtaining stable clones containing the desired expression of channels. In another aspect, screening of test compounds on single cells could be performed with a microfluidic device equipped with one or more additional fluid injection ports and one or more embedded electrical stimulator devices built and operated based on the methods described herein.

5. Electrical Stimulation Methods a. Introduction

Without being bound to any mechanism of action, the present inventors provide the following description for the effect of electrical stimulation on cellular transmembrane potentials.

Typical voltage-dependent ion channels have a variety of conducting and non-conducting states that are regulated by the local relative transmembrane potential of the cell. By appropriately applying external electrical fields to the cells, portions of the cell membrane can be driven to any desired transmembrane potential, thereby enabling the regulation of the conduction states of voltage dependent ion channels present within the cell. If the applied electrical field is appropriately varied, it is possible to sample a number of conductance states of most ion channels, thereby cycling them through resting, activated, and inactivated states.

Depending on the ion channel in question, activation of the ion channel can lead to the release, or uptake, of ions into the cell that can result in global transmembrane potential changes in the cell. By applying a repetitive train of electrical stimuli, separated by a time interval smaller than the membrane time constant, large sustained membrane voltage changes can be created via a stepwise accumulation or loss of ions. This process allows the direct measurement of many ion channels and provides a facile method whereby the transmembrane potential of the cell can be externally controlled. This approach therefore provides for improved methods of drug discovery that are compatible with high throughput screening.

b. Overview of a Typical Stimulation Protocol

Figure 4:
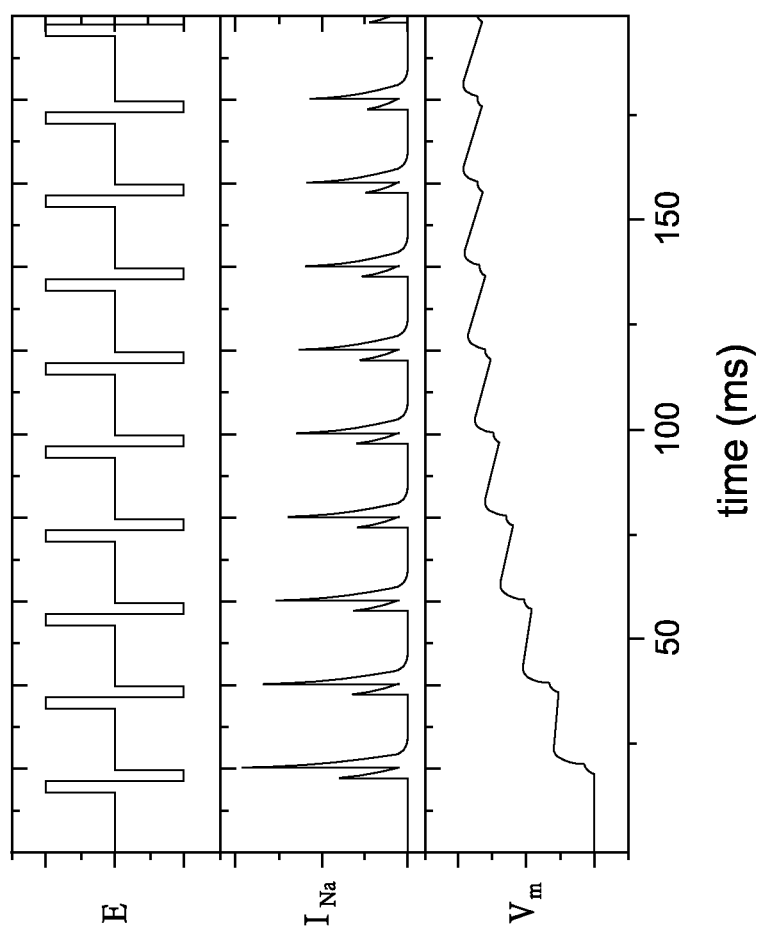
FIG. 4. Shows the simulated effects of repetitive external electrical fields on a cell expressing a voltage dependent sodium channel. The upper panel indicates the applied electrical field, the middle panel indicates the simulated sodium current into the cell, and the lower panel indicates the simulated average transmembrane potential.

The simulated influence of a typical biphasic electrical stimulation protocol on a cell line expressing a voltage activated sodium channel is illustrated, in simplified form, below. The following description assumes that the cell line has no significant expression of other ion channels, and that the resting transmembrane potential of the cell is above the threshold for inactivation of the sodium channel in question. In FIG. 4, the upper panel shows the time course of the applied electrical field (E), the middle panel shows the simulated inward sodium currents ($I_{Na}$) in response to the applied electrical field, and the lower panel shows the idealized average transmembrane potential of the cell ($V_m$). In this example, the recordings relate to the changes in these parameters that a single cell placed in the center of the applied electrical field would be typically expected to experience during an electrical stimulation wave train.

Referring to the first pulse, establishing the first electrical field causes a potential drop across the cell that is maximal, with respect to the resting transmembrane potential of the cell, at the edges of the cell closest to the electrodes (see Hibino et al., Biophysical Journal 64:1789-1800, 1993; Gross et al. 1986, Biophys. J. 50:339-348). The magnitude of the electric field-induced transmembrane potential change $\Delta V_M$ at a given point of the membrane in an idealized spherical cell can be described by the formula (Ehrenberg et al., Biophys. J. 51:833-837, 1987):

$$\Delta V_m = -fgrE \cos \theta. \quad (1)$$

In Equation 1, f is a factor dependent upon the conductivity of the membrane, g is a geometric factor of order 1, r is half the diameter of the cell parallel to the electric field, E is the local magnitude of the electric field, and θ is the angle between the local direction of the field and a line drawn from the center of the cell to the point of the surface being considered. For most intact mammalian cells, in which the membrane conductivity is very low compared to the conductivity of the solution bathing the cells, the factor f≈1. In practice, cells are rarely spherical when attached to a substrate and an accurate estimate of the actual magnitude of the electrical field induced transmembrane potential changes may be empirically determined.

As a result of the applied electrical field, the membrane on the side nearest to the anode is driven negative, while the membrane on the side nearest the cathode is driven positive. In cells in which one edge is driven sufficiently negative to locally lower the transmembrane potential below the threshold potential for release of inactivation for the ion channel in question, the applied electrical field causes the sodium channels located on this edge to enter the resting state. On the other side of the cell, the transmembrane potential is driven positive of the resting potential. Because the resting transmembrane potential of the cell is assumed to be above the threshold for inactivation, sodium channels on this side of the cell remain inactivated and do not pass current. If the resting transmembrane potential were instead below the inactivation threshold, channels on this side of the cell would activate and pass current.

When the applied field is reversed, the profile of transmembrane potential changes also reverses. The transmembrane potential changes induced by the electric field on the patches of membrane at the extreme edges of the cells switches polarity. The channels on the side that was driven negative during the first phase of stimulation are now driven positive. If the stimulation parameters are properly chosen, these channels are now driven above the activation potential and begin to allow sodium ion influx. This is shown in FIG. 4, as the first smaller peak of sodium influx into the cell. The sodium channels rapidly inactivate after a characteristic time. Meanwhile, on the other side of the cell, the transmembrane potential is driven negative so that the sodium channels release from inactivation and move into the resting state.

When the second stimulus phase ends, all parts of the membrane rapidly return to a new average transmembrane potential. If the average transmembrane potential is now above the activation potential of the sodium channels, the channels on the side of the cell that was driven negative during the second phase of stimulation activate and begin to allow sodium ion influx. This is shown in FIG. 4, as the second larger peak of sodium influx into the cell. The sodium channels rapidly inactivate after a characteristic time. In this case sodium influx is typically larger from the second side than the first side, since the driving force for sodium entry is larger when this part of the membrane is driven more positive by an electric field.

Each pulse of sodium channel influx raises the average transmembrane potential of the cell (FIG. 4, lower panel). This rise in transmembrane potential can be detected by any of the methods described herein, but is conveniently measured via fluorescence emission ratio changes of a FRET based voltage-sensitive dye. Due to leakage currents present in all cells, this average transmembrane potential shift decays exponentially to the original resting transmembrane potential. The time dependency of this response, the membrane time constant ($\tau_m$), depends upon the membrane capacitance and membrane resistance, and is highly variable from one cell type to another. For example, time constants can vary from 100 μs to over one second, depending on the cell type. Typically the membrane time constant is around 100 ms for most engineered cell lines. To provide a net accumulation of sodium influx the stimulus pulse is repeated before the transmembrane potential has time to decay to the resting transmembrane potential. During subsequent rounds of electrical stimulation, positive charge is steadily accumulated into the cell raising the average transmembrane potential in an approximately stepwise fashion with each repetition of electrical stimulation. After each pulse of electrical stimulation, the magnitude of the sodium ion influxes become steadily smaller as the average transmembrane potential approaches the sodium ion reversal potential. Eventually an equilibrium transmembrane potential is established in which leakage of current out of the cell equals the current influx due to electrical stimulation.

c. Adjustable Parameters for the Stimulus Waveforms

The present invention includes the use of any waveform kernel with any repetition procedure capable of selectively activating ion channels in living cells. The kernel is the repeatable structure that forms the basis of the stimulus train. In FIG. 4, the kernel is a biphasic square pulse, but in principle it could be any limited-time wave function. The time duration of the kernel sets the maximum rate at which it can be repeated. The repetition procedure dictates how and when the kernel is presented to the sample. In FIG. 4, the repetition rate is fixed and continues for a total of ten cycles. However the repetition rate need not be fixed.

Additionally, the kernel can be changed during the stimulus train, so that each time the repetition procedure calls for a stimulus pulse, a different wave function could be used. Furthermore, a feedback mechanism could be used to alter the kernel and/or the repetition procedure based upon the measured response of the system.

The use of arbitrary waveform generators to create the stimulus kernels and trains allows for a virtually unlimited variation in the waveform in order to tune the electrical stimulus to a particular cell type or specific ion channel. The pulse train can be readily modulated via the variation of a number of separately controllable components.

i. The Shape of the Individual Pulses.

Figure 5:
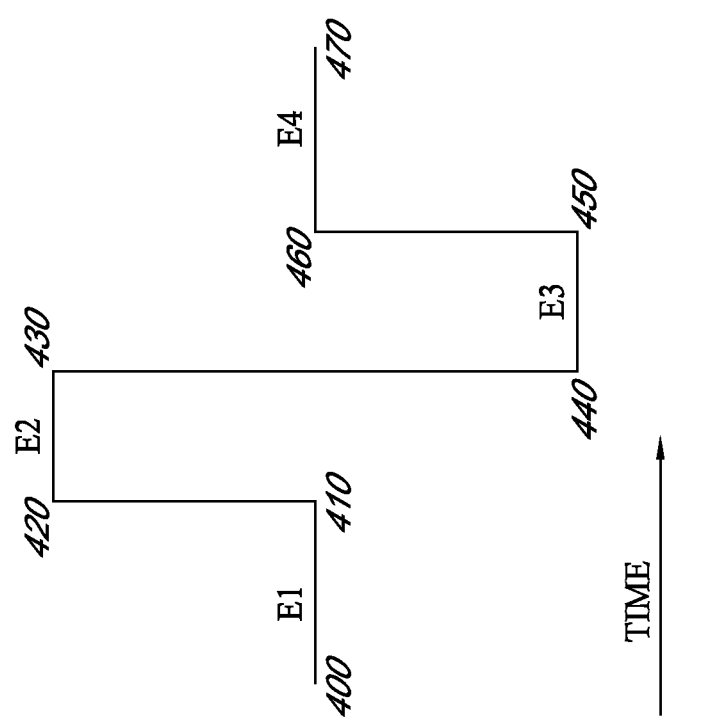
FIG. 5 Shows a schematic representation of a square wave.

The waveform kernel that is repeated during the stimulus train can be changed with nearly endless permutations using a arbitrary digital waveform generator, such as Tektronix AFG 310. FIG. 5 shows a schematic representation of a biphasic square waveform to illustrate some of the variables that can be modulated. In FIG. 5, the pulse train consists of a starting field $E_1$ (400), that lasts for a time $t_1$, a rapid increase in potential (410), that takes a time $t_2$, until reaching a first stimulating field $E_2$ (420) that lasts for time $t_3$, a rapid decrease in potential (430) that takes time $t_4$, until reaching a second stimulating field (440), $E_3$ that lasts a time $t_5$, a rapid increase in potential (460) that takes time $t_6$, until reaching the finishing field (470), $E_4$ that lasts a time $t_7$ until the cycle is repeated. The magnitude and polarity of the electrical fields $E_1$ to $E_4$ are separately controllable and may be both statically and dynamically varied as described below. The times for which the electrical potentials are applied to the cells, times $t_1$, $t_3$, $t_5$, and $t_7$ are also separately controllable and may be both statically and dynamically varied between 0 and 10 s during a wave train, as described below. Finally the changes in potential that occur over times $t_2$, $t_4$ and $t_6$, may occur over variable time periods between 0 and 100 ms and be either linear or non linear to create waveforms of variable shapes.

Figure 6:
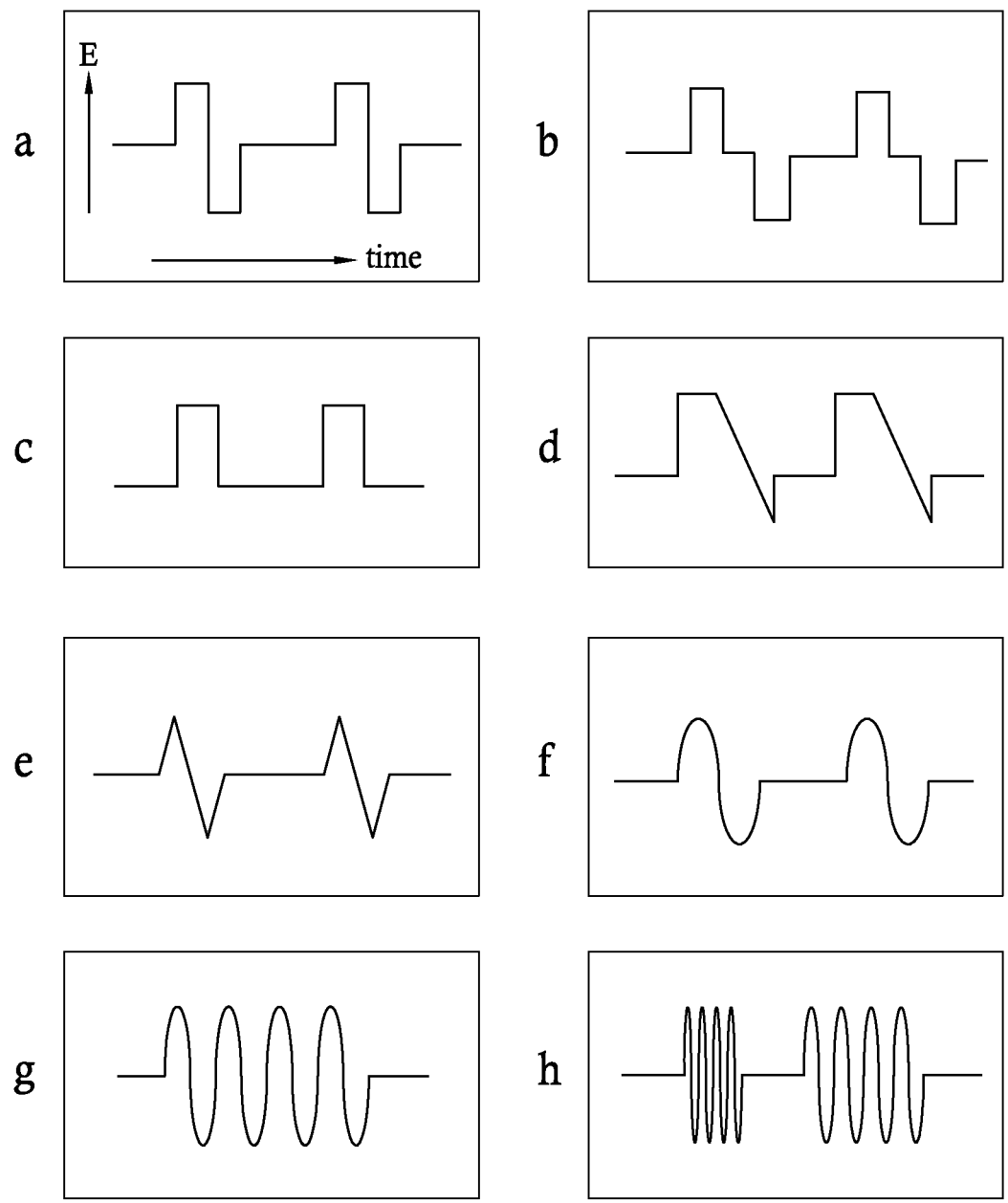
FIG. 6 Shows examples of various wave kernels.

Some examples of these types of variation in the waveform are shown in FIG. 6 (a) Biphasic waveform, as shown in FIG. 5, repeated at a rate f. (b) A modified biphasic waveform. A short interval has been added between the stimulation phases of the wave train. This allows current to flow through the channels released from inactivation during the first pulse. (c) Monophasic waveform. Only channels on the side of the cell facing the anode will be released from inactivation. (d) A ramped waveform. The anode-facing channels will be released from inactivation by the square wave. The channels will activate and pass current during the ramp. The ramp allows the channels to open and pass current at more negative local potentials, so that even when the cell is near the reversal potential for sodium ions, large currents can still flow. The point along the ramp at which the channels will open varies. (e) A biphasic triangular or sawtooth waveform. Ramping may allow the voltage-dependent transitions between states to occur more uniformly as the global membrane potential changes. Monophasic triangular waveforms are also possible. (f) A sinusoidal waveform. This type of waveform may reduce electrical noise during high frequency stimulation. (g) A short burst of sinusoidal waveforms. (h) Bursts of sinusoidal waveforms, each with different fundamental frequency. This type of stimulation may prove useful for studying plasticity effects. The first burst(s) are used to train the system or begin a process, while the subsequent bursts(s) are used to assay the system.

Variations in waveform shape may be useful in maintaining fixed stimulus conditions during the pulse train. For example, the transmembrane potential excursions experienced by a highly polarized cell will vary as its average transmembrane potential changes from around −90 mV at the beginning of the stimulation cycle to around +60 mV after several repetitive stimulation cycles. As a consequence, the applied electrical field required to efficiently release an ion channel from inactivation varies as the average potential of the cell varies during the course of several stimulation cycles. To take this effect into consideration it may be useful, under certain circumstances, to change the relative balance between the positive ($E_2$) and negative ($E_3$) phases of stimulation as the wave-train progresses.

Some cell lines, for example HEK-293, have a resting average transmembrane potential below the activation threshold of some voltage-activated sodium channels. In these cells as the transmembrane potential rises during stimulation as a result of sodium ion influx, the sodium channels can open independently of the applied electrical stimulation. This can be improved by using a sloped current pulse (i.e by increasing $t_2$ and $t_4$). Then, the channels can pass current for a defined time just above the activation voltage, independent of the average transmembrane potential of the cell.

ii. The Overall Amplitude of the Individual Pulse $E_2$ and $E_3$.

The magnitude and polarity of the pulse amplitude controls the relative transmembrane potential excursions experienced by the cell during a stimulus pulse. Pulse amplitudes can be altered for the entire train, or for the individual pulses to accommodate different channels and cell types, as discussed in more detail below. In general, the magnitudes of $E_2$ and $E_3$ are selected to ensure that the ion channel of interest is efficiently activated, and released from inactivation during each stimulation cycle, while at the same time not of sufficient magnitude so as to cause irreversible electroporation of the cells. Preferred pulse amplitudes for $E_2$ and $E_3$ are typically in the range of 5 to 60 V/cm for most ion channels when expressed in non-excitable mammalian cells with average sizes from 10 to 25 µm, and may vary either positive or negative relative to earth. As above, the amplitude of the stimulus can be changed during the pulse train to maintain stable stimulus conditions as the average transmembrane potential changes. Preferred pulse amplitudes are inversely dependent upon average cell size. So, the technique can also be used on cells which are smaller or larger than 10 to 25 µm, by altering the pulse amplitude.

iii. The Duration of the Individual Pulses ($t_3$ and $t_5$).

Many channels require alterations in the transmembrane potential for extended periods of time to release them from inactivation, prior to opening. For example, many voltage-dependent sodium channels generally need to experience a transmembrane potential below −90 mV for several milliseconds before they are released from inactivation. Efficient use of the electrical stimulation protocol therefore typically requires that the duration of the pulses $t_3$ and $t_5$ are sufficient to enable complete, or almost complete, release from inactivation for the ion channel of interest. In some cases it may be desirable to tune the magnitude of $t_3$ and $t_5$ to enable the selective release from inactivation of one class, but not another class of ion channel in a cell that expresses several ion channel types. In other cases it may be desirable to make $t_3$ and $t_5$ very small to achieve low levels of release from inactivation for the channels. Typically the preferred pulse duration is matched to the characteristic time for transitions between the desired voltage-dependent states for the ion channel of interest, and these are typically in the range of about 0.1 to 100 msec for most ion channels.

To avoid excessive electrolysis of water and consequent gas bubble generation, the duration of the pulses $t_3$ and $t_5$ should be kept as short as possible, while still achieving the desired electrical stimulation. Water electrolysis at a metal/water interface typically occurs when the magnitude of the voltage difference between the metal and the water exceeds about 0.8 V. In some cases, the stimulus parameters required to produce cellular stimulation also cause water electrolysis. Some generation of gas at the electrodes is typically acceptable as long as the charge per unit area of the electrode/water interface delivered during any single polarity phase of a single pulse is less than about 100 µC/mm². Exceeding this limit typically causes gas evolution and bubble formation that significantly affects field uniformity. The presence of bubbles on the electrode surface occludes that part of the electrode, and can cause alterations in the electric field uniformity. Generation of large amounts of gas can also cause oxidative damage to the cells and the dyes in the well.

In a 96-well plate with 100 µL of physiological saline with resistivity 70 Ω-cm, the resistance of the saline between two parallel plate electrodes with a 4 mm gap between them inserted into the well to within 0.5 mm of the bottom of the well, is approximately 230Ω. Each electrode has a contact area with the saline of about 24 mm². Thus, any single-polarity phase of the stimulus protocol should not deliver more than about 2.4 mC of charge. A voltage difference of about 10 V applied between the plates generates an electric field of about 25 V/cm in the saline. This voltage will draw about 43 mA of current. Thus for this electrode configuration, a square wave, single-polarity pulse should not exceed about 55 milliseconds in duration in order to limit the charge to less than 2.4 mC.

iv. The Gap between Successive Stimuli ($t_1$ and $t_7$).

Changing the value of $t_1$ and $t_7$ globally for the train, or adjusting it for each individual pulse during the train, is useful for optimizing the stimulation protocol for specific ion channels. Additionally the approach is also useful for determining certain cellular and channel properties including the open channel time and the time course of the channel activation and inactivation.

For example, for assays involving voltage regulated sodium channels, the insertion of a time delay ($t_1+t_7$) between pulses equal to, or less than, the average sodium channel open time allows for a quantitative measurement of the inactivation kinetics of the channel. The inactivation kinetics are directly related to the average open channel time. Thus, assays using short interpulse intervals allows for the detection of compounds whose primary effect is on inactivation kinetics, a mechanism which is otherwise inaccessible using high-throughput techniques.

In most cases the time delay between successive stimuli would be less that the membrane time constant in order to obtained sustained increases in transmembrane potential. Typically optimal frequencies of stimulation (f) are within the range $\tau_M^{-1} \leq f \leq \tau_b^{-1}$ where $\tau_M$ is the time constant for decay of transmembrane potential changes, and $\tau_b$ is the average channel open time. Some channels do not inactivate, and for these cells the stimulation frequency may be determined empirically. Additionally, the stimulation frequency f cannot exceed the inverse of the time duration of the stimulus kernel.

Additionally, for certain cell types, it may prove desirable to stimulate at a slower rate. For example, slower stimulation rates may be preferred for cells with high channel densities, or for assays in which higher pharmacological sensitivity is required. Alternatively for these cases, a monopolar stimulus could be used. This would only release from inactivation the sodium channels on one side of the cell, but the maximum frequency of stimulation could be doubled.

v. The Duration of the Train of Pulses, or Number of Pulses in the Train.

Cellular and channel properties can be assayed both in dynamic (i.e. rise and fall times, alterations in response shape, etc.) and static modes. Both modes require stimulus train durations long enough to explore all the events of interest, yet not longer than necessary to complete the assay. Typical stimulation times comprise 10 msec pulses, at 25 V/cm pulses repeated at a frequency of 20 Hz for 3 seconds. Adjusting these parameters allows assay times to be reduced, or to explore processes with both fast and slow time scales.

vi. Multiple Pulse Trains.

In some cases it is useful to repeat pulse trains, or to perform a measurement on the same cells with two different pulse trains. One example would be to completely characterize the properties of a channel by measuring the response as a function of stimulus frequency and duration, using a single plate of cells subjected to multiple stimulus trains. Another example would be to examine plasticity of the response (i.e. activity-dependent changes in response). One or more stimulus trains would condition the response, while sets of measurement trains before and after the conditioning would determine the changes due to activity.

vii. Feedback of Stimulus Parameters Based upon Dynamic Measurements of the Response.

The present invention can also be used to create a voltage clamp device, by using a dynamic feedback loop to maintain the average transmembrane potential at a preset value. By measuring the transmembrane potential using a fast fluorescent output as described below, then changing stimulus parameters to compensate for any changes in transmembrane potential, it is possible to dynamically control the transmembrane potential of the cells. The current necessary to maintain that potential would then be determined by computer control of the stimulus parameters.

viii. The use of High Frequency Stimulation to Avoid Electrolysis

During typical stimulation parameters, a peak current of approximately 50 mA passes through the solution between the electrodes. During this time various electrochemical reactions occur which typically generate toxic species to the cells. Preliminary experiments have shown that most mammalian cells typically respond normally for approximately two minutes of electrical stimulation using stainless steel electrodes. However prolonged stimulation for longer time periods appears to lead to a loss in cell health and viability. At sufficiently high pulse frequencies, such that the metal-saline interface does not reach the potential for electrolysis of water (approximately ±1V for stainless steel in saline), current can be passed capacitively and no toxic products will be generated. In the electrical stimulator shown in FIG. 1, in which each electrode has an area of about 24 mm$^2$ in contact with the saline, the capacitance per electrode is around 1-10 µF (Robinson, 1968, Proc. IEEE 56:1065-1071). At 50 mA, this capacitance charges to 1 V in around 20-200 µs. This is at the lower limit of the useful pulse duration times.

Alternatively it is possible to perform electrical stimulation without generating electrolytic products. Several treatments are available which can increase the capacitance of the metal-saline interface by factors of 2-100. These include surface roughening, electroplating with platinum black or gold black, and deposition and activation of iridium/iridium oxide, titanium/titanium nitride, or polypyrrole films. Using stimulation parameters, which avoid irreversible electrochemistry, these surface treatments do not degrade when passing current.

6. Expression of Ion Channels a. Selection of the Cell Type

The present invention can be used with any type of cell, including animal cells, plant cells, insect cells, bacterial cells, yeast and mammalian cells. For screening for human therapeutics mammalian cell lines are preferred, such cell lines include tissue culture cell lines that can be relatively easily grown, and can be readily transfected with high efficiency. Many tissue cell lines are commercially available through the American type culture collection (ATCC) see (http://www.atcc.org), as well as the European collection of cell cultures (ECACC) (http://www.camr.org.uk).

Additionally in some cases primary cell lines, or tissue slices may also be preferred for screening when it is required to express, or measure, the response of the ion channel of interest in its native physiological context. This approach may be useful either as a primary or a secondary screen to screen for specificity, selectivity or toxicity of candidate therapeutics, and is discussed in detail in section X.

For assays performed on cultured cell lines, the main selection criteria are the resting transmembrane potential of the cell line, and the presence of endogenously expressed ion channels. The selection of appropriate cell lines for specific ion channels of interest are dependent on the voltage dependent properties and ion selectivity of the ion channel of interest. These considerations are reviewed in detail for a number of ion channels in section VIII, Stimulation Protocols.

In some cases it is desirable to use a cell line which has no (or very low) detectable endogenous expression of other ion channels. Cells of this type include CHO-K1, CHL, and LTK (−) cells. These cells inherently have a resting potential in the range of +10 to −30 mV, which is above the activation and inactivation thresholds of most voltage-dependent channels. Use of these cell lines has the advantage that the ion channel of interest is the major modulator of transmembrane potential within the cells so that screening assay data are generally easily and unambiguously interpreted.

In some cases the use of a cell line with no other ion channels may not be practical to create a workable assay. For example, it may be necessary to maintain a voltage-regulated ion at a highly polarized transmembrane potential. In this case it is necessary control the transmembrane potential via the expression of a second ion channel. For example to assay a rat brain type IIa sodium channel in the resting state requires the transmembrane potential to be maintained below the threshold activation potential of the sodium channel, in this case around −60 mV. To achieve this it is necessary to either co-express an ion channel, such as a potassium inward rectifier, that can maintain the resting transmembrane potential of the cell to around −90 mV, or identify a cell line that endogenously expresses similar ion channels. Cell types of this type include RBL cells and HEK-293 cells.

In other cases it may be necessary to use the expression of a second ion channel, in conjunction with electrical stimulation to drive the cell membrane to a specific transmembrane potential, to enable the first ion channel of interest to be assayed. Examples of this situation occur when assaying non-voltage regulated ion channels such as ligand-gated channels. Co-expression of a voltage regulated sodium channel, for example in conjunction with electrical stimulation can be used to set the transmembrane potential to transmembrane potentials of between about +10 to +60 mV. By comparison, co-expression of voltage regulated potassium channels in conjunction with electrical stimulation can set the transmembrane potential to transmembrane potentials of between about −90 to −30 mV. These approaches thus enable the effective manipulation of the transmembrane potential over a relatively wide range thereby enabling the analysis of virtually any ion channel.

Typically when using this co-expression approach it is necessary to re-screen any hits obtained with the cell line co-expressing both ion channels, with the cell line expressing only the ion channel used to set the transmembrane potential. This enables drugs that affect this second ion channel to be differentiated from those that actually influence the ion channel of interest. Alternatively selective toxins such as TTX can be used to selectively inhibit one class of ion channel.

b. Transfection of Ion Channels

Nucleic acids used to transfect cells with sequences coding for expression of the ion channel of interest are typically in the form of an expression vector including expression control sequences operatively linked to a nucleotide sequence coding for expression of the channel. As used, the term "nucleotide sequence coding for expression of a channel" refers to a sequence that, upon transcription and translation of mRNA, produces the channel. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Methods which are well known to those skilled in the art can be used to construct expression vectors containing the ion channel coding sequence, operatively coupled to appropriate localization or targeting domains and appropriate transcriptional/translational control signals. For example by reference to the sequence accession numbers, or references in Tables 1 to 3, one or ordinary skill in the art can identify the sequence of the ion channel of interest. These methods include in vitro recombinant DNA techniques, synthetic techniques and in vivo recombination/genetic recombination. (See, for example, the techniques described in Maniatis, et al., *Molecular Cloning A Laboratory Manual*, Cold Spring Harbor Laboratory, N.Y., 1989). Many commercially available expression vectors are available from a variety of sources including Clontech (Palo Alto, Calif.), Stratagene (San Diego, Calif.) and Invitrogen (San Diego, Calif.) as well as and many other commercial sources.

A contemplated version of the method is to use inducible controlling nucleotide sequences to produce a sudden increase in the expression of the ion channel of interest e.g., by inducing expression of the channel. Example inducible systems include the tetracycline inducible system first described by Bujard and colleagues (Gossen and Bujard (1992) Proc. Natl. Acad. Sci USA 89 5547-5551, Gossen et al. (1995) Science 268 1766-1769) and described in U.S. Pat. No. 5,464,758.

Transformation of a host cell with recombinant DNA may be carried out by conventional techniques as are well known to those skilled in the art. Where the host is prokaryotic, such as *E. coli*, competent cells that are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the ion channel, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the ion channel. (*Eukaryotic Viral Vectors*, Cold Spring Harbor Laboratory, Gluzman ed., 1982). Preferably, a eukaryotic host is utilized as the host cell as described herein.

Selection of stable clones will typically be made on the basis of successful expression of the ion channel of interest at sufficient level to enable it's facile detection. In many cases this analysis will require functional characterization of individual clones to identify those that exhibit appropriate electrophysiological characteristics consistent with expression of the clone of interest. This analysis can be completed via the use of patch clamping, or via the measurement of transmembrane potentials using transmembrane potential sensitive dyes as described below. An advantage to the use of this latter method is that it is compatible with fluorescence activated cell sorting and provides for the rapid analysis of many thousands of individual clones per second. In some cases where the sodium channel is electrically silent in the resting cell, confirmation of expression can also be readily achieved by immunochemistry using antibodies raised against the native ion channel, or a defined epitope introduced in the ion channel via molecular techniques as described above.

In cases where cells are transfected with a first ion channel of interest, and a second ion channel to set the transmembrane potential, optimization of the relative expression of both ion channels is important. Typically the optimal relative expression of the two ion channels is determined empirically by selecting clones that provide the maximum dynamic range and minimal statistical variation in their response.

7. Measurement of Transmembrane Potentials

Transmembrane potential changes and the measurement of specific ion channels conductance via the use of the present invention can be detected by use of any of the known means of measuring transmembrane potential or ion movement. These methods include, for example, patch clamping (Hamill et al, Pfluegers Arch. 391:85-100, 1981), FRET based voltage sensors, electrochromic transmembrane potential dyes (Cohen et al., Annual Reviews of Neuroscience 1: 171-82, 1978), transmembrane potential redistribution dyes (Freedman and Luis, Spectroscopic membrane probes Ch 16, 1988), extracellular electrodes (Thomas et al., Exp. Cell Res. 74: 61-66, 1972), field effect transistors (Fromherz et al., Science 252: 1290-1293, 1991), radioactive flux assays, ion sensitive fluorescent or luminescent dyes, ion sensitive fluorescent or luminescent proteins, the expression of endogenous proteins or the use of reporter genes or molecules.

Preferred methods of analysis for high throughput screening typically involve the use of optical readouts of transmembrane potential, or ion channel conductance. Such methods include the use of transmembrane potential or ion sensitive dyes, or molecules, that typically exhibit a change in their fluorescent or luminescent characteristics as a result of changes in ion channel conductance or transmembrane potential.

A preferred optical method of analysis for use with the present invention has been described in U.S. Pat. No. 5,661,035 issued Aug. 26, 1997, hereby incorporated by reference). This approach typically comprises two reagents that undergo energy transfer to provide a ratiometric fluorescent readout that is dependent upon the transmembrane potential. Typically the approach uses a voltage sensing lipophilic dye and a voltage insensitive fluorophore associated with a cell membrane. (see Gonzalez et al. Drug Discovery Today 4:431-439, 1999).

In one embodiment, two dye molecules, a coumarin-linked phospholipid (CC2-DMPE) and an oxonol dye such as bis-(1,2-dibutylbarbituric acid) trimethine oxonol [$DiSBAC_4$(3)], are loaded into the plasma membrane of cells. CC2-DMPE partitions into the outer leaflet of the plasma membrane where it acts as a fixed FRET donor to the mobile, voltage sensitive oxonol acceptor. Cells with relatively negative potentials inside will push the negatively charged oxonol to the outer leaflet of the plasma membrane, resulting in efficient FRET (i.e. quenching of the coumarin donor and excitation of the oxonol acceptor). Depolarization results in rapid translocation of the oxonol to the inner surface of the plasma membrane, decreasing FRET. Because FRET can only occur over distances of less than 100 Å, excitation of the coumarin results in specific monitoring of oxonol movements within the plasma membrane.

The response times for these assays is readily altered by increasing or decreasing the hydrophobicity of the oxonol. For example, the more hydrophobic dibutyl oxonol $DiSBAC_4$(3) has a time constant of approximately 10 ms, significantly faster than the less hydrophobic diethyl oxonol $DiSBAC_2$(3).

Loading of the dyes is typically achieved at room temperature prior to the start of transmembrane potential measurements. Typically cells are loaded sequentially with the coumarin lipid followed by the oxonol. Typical loading concentrations for coumarin lipids range from about 4 to 15 µM (final concentration) and staining solutions are typically prepared in Hanks Balanced salt solution with 10 mM HEPES, 2 g/L glucose and about 0.02% Pluronic-127 at a pH of around 7.2 to 7.4. Loading is usually acceptable after about 30 minutes incubation, after which excess dye may be removed if desired. Oxonol dyes are typically loaded at a concentration between 2 and 10 μM for 25 minutes at room temperature, the more hydrophobic DiSBAC$_4$(3) is usually loaded in the presence of 2-3 μM Pluronic-127. Optimal loading concentrations vary between cell types and can be empirically determined by routine experimentation. Typically such optimization experiments are conducted by systematically titrating the concentrations of the first reagent, and then for each concentration tested, titrating the concentration of the second reagent. In this way it is possible to obtain both the optimal loading concentrations for each reagent, and the optimal relative ratio to achieve a maximal signal to noise ratio.

In some cases it may be preferred to add, or load one, or more of the FRET reagents with one or more light absorbing substances in order to reduce undesired light emission, as for example described in commonly owned U.S. patent application Ser. No. 09/118,497, filed Jul. 17, 1998; U.S. patent application Ser. No. 09/120,516, filed Jul. 21, 1998, and U.S. patent application Ser. No. 09/122,477 filed Jul. 23, 1998.

FRET based voltage sensors may also be derived from the use of other membrane targeted fluorophores in conjunction with a mobile hydrophobic donor or acceptor. Other such compositions are disclosed, for example, in U.S. patent application Ser. No. 09/459,956, filed Dec. 13, 1999.

Suitable instrumentation for measuring transmembrane potential changes via optical methods includes microscopes, multiwell plate readers and other instrumentation that is capable of rapid, sensitive ratiometric fluorescence detection. A preferred instrument of this type is described in U.S. patent application Ser. No. 09/118,728 filed Jul. 17, 1998. This instrument (the Voltage/Ion Probe Reader or VIPR™) is an integrated liquid handler and kinetic fluorescence reader for 96-well and greater multiwell plates. The VIPR™ reader integrates an eight channel liquid handler, a multiwell positioning stage and a fiber-optic illumination and detection system. The system is designed to measure fluorescence from a column of eight wells simultaneously before, during and after the introduction of liquid sample obtained from another microtiter plate or trough. The VIPR™ reader excites and detects emission signals from the bottom of a multiwell plate by employing eight trifurcated optical bundles (one bundle for each well). One leg of the trifurcated fiber is used as an excitation source, the other two legs of the trifurcated fiber being used to detect fluorescence emission. A ball lens on the end of the fiber increases the efficiency of light excitation and collection. The bifurcated emission fibers allow the reader to detect two emission signals simultaneously and are compatible with rapid signals generated by the FRET-based voltage dyes. Photomultiplier tubes then detect emission fluorescence, enabling sub-second emission ratio detection.

8. Stimulation Protocols

In one aspect, the present invention includes methods for modulating the transmembrane potentials of living cells via electrical stimulation, and the use of these methods for assaying the activity of virtually any ion channel or transporter system.

a. Measurement of Specific Channel Conductances
       i. Assay of Sodium Channels A variety of different isoforms of mammalian voltage dependent sodium channels have been identified, and are summarized below in Table 1. These channels can be classified into three main groups (for review see Goldin, Annals N.Y. Academy of Sciences 868:38-50, 1999).

TABLE 1

Sodium Channel Sub-type Summary

| Channel Name & Gene Symbol | Sub-type/ Alternate names | Tissue Distribution | Accession Number |
|---|---|---|---|
| SCN1A (Nav1.1) | Rat I (rat) | CNS/PNS | X03638 |
|  | HBSCI (human) | CNS | X65362 |
|  | GPB1 (Guinea pig) | CNS | AF003372 |
| SCN2A (Nav1.2) | Rat II (rat) | CNS | X03639 |
|  | HBSCII (human) | CNS | X65361 |
|  | HBA (human) | CNS | M94055 |
| Nav 1.2A | Rat IIA | CNS | X61149 |
| SCN3A (Nav 1.3) | Rat III (rat) | CNS | Y00766 |
| SCN4A (Nav1.4) | SkM1, μl (rat) | skeletal muscle | M26643 |
|  | SkM1 (human) | Skeletal muscle | M81758 |
| SCN5A (Nav1.5) | SkM2 (rat) | skeletal muscle/ heart | M27902 |
|  | RH1(rat) |  |  |
|  | H1(human) | heart | M77235 |
| SCN8A (Nav1.6) | NaCh6 (rat) | CNS/PNS | L39018 |
|  | PN4a (rat) | CNS/PNS | AF049239A |
|  | Scn8a (mouse) | CNS | U26707 |
|  | Scn8a (human) | CNS | AF050736 |
|  | CerIII (Guinea pig) | CNS | AF003373 |
| SCN9A (Nav1.7) | PN1 (rat) | PNS | U79568 |
|  | HNE-Na (human) | thyroid | X82835 |
|  | Nas (rabbit) | Schwann cells | U35238 |
| SCN10A Nav1.8 | SNS (rat) | PNS | X92184 |
|  | PN3 (rat) | PNS | U53833 |
|  | SNS (mouse) | PNS | Y09108 |
| SCN6A Nav2.1 | Na2.1 (human) | Heart, uterus muscle | M91556 |
| SCN7A Nav2.2 | Na-G (rat) | astrocytes | M96578 |
|  | SCL11(rat) | PNS | Y09164 |
| Nav2.3 | Na2.3 (mouse) | Heart, uterus muscle | L36179 |
| Nav3.1 | NaN (rat) | PNS | AF059030 |
| SCN1B Naβ1.1 | β-1 (rat) | CNS | M91808 |
|  | β-l (human) | CNS | L10338 |
| SCN2B Naβ2.1 | β-2 (rat) | CNS | U37026 |
|  | β-2 (human) | CNS | AF007783 |

The voltage-dependent sodium channels in Table 1 vary widely in their voltage dependency and inactivation and activation kinetics. Voltage-gated sodium channels have many different conformations, which can be classified into three states. (1) The resting state, in which the channel is closed and no current can flow. This is the typical state when a sodium channel is expressed in a cell with a resting transmembrane potential of below about −60 mV. The channel can be rapidly driven into the open state by depolarization, usually to a transmembrane potential of above about −50 mV. (2) The activated state, in which the channel is open and ions can pass through. Because the intracellular concentration of sodium is low in a normal resting cell, while the extracellular concentration is high, sodium ions flow into the cell and drive the transmembrane potential more positive. The open state has a short lifetime, generally on the order of one millisecond, after which it passes into the inactivated state. (3) The inactivated state, in which a channel has closed and ions can not pass through the channel. The channel cannot be directly opened once in the inactivated state. It will first go to the resting state, which occurs if the transmembrane potential is held very negative (generally below −80 mV) for several milliseconds. The time constants and threshold potentials for transitions between these three states vary greatly between channel subtypes.

During these experiments, the response will be compared for cells with active channels, and for cells in which the channels are pharmacologically blocked. If a suitable pharmacological agent is not available, the blocked state can be emulated with an un-transfected cell line. The optimal stimulus parameters will yield the smallest coefficient of variation of the difference in signals of the two cell populations.

(a) Assays for Voltage-Dependent Sodium Channels in an Inactivated State

Preferred cells include those with resting transmembrane potentials above the activation threshold for the ion channel of interest, and in which there are no other ion channels expressed. Cells meeting these criteria include CHL and LTK (−) cells. After choosing a target ion channel, cells are transfected and clones are selected as described in section III. Alternatively, a cell line that endogenously expresses the channel of interest, and low levels of other channels, could be used. For example, the CHO-K1 cell line expresses a voltage-gated sodium channel, and very low levels of other ion channels. Cells are plated into multiwell microtiter plates, cultured, and stained with voltage-sensitive dyes as described in section IV prior to initiating electrical stimulation. Initial experiments are typically carried out in a 96-well multiwell plate, with an equal number of cells in each well. Generally columns of eight wells are simultaneously stimulated under identical conditions to provide statistically significant data on the variation in cellular response.

An optimal electrical stimulation protocol should hyperpolarize part of the plasma membrane of the majority of the cells long enough to release the sodium channels from inactivation, prior to providing an activating depolarization, without electroporating or killing the cells. Typically this requires sustained transmembrane potentials of around −60 to −80 mV for periods ranging from about 0.5 to about 20 ms to be created within the cell.

A preferred stimulation protocol that achieves this effect is biphasic, so that ion channels present on both the extreme edges of the cells are released from inactivation as the biphasic waveform reverses polarity. Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude (up to a maximum of about 60 V/cm), duration (in the range of 0.1 to 50 ms), and then frequency (in the range of 0 to 1 kHz). If necessary changes in the pulse shape could also be explored to determine if these resulted in more efficient electrical stimulation. The optimal stimulus parameters will yield the maximum cellular stimulation (compared to cells with the channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

(h) Assays for Sodium Channels Normally in the Resting State

Preferred cells include those with resting transmembrane potentials below the activation threshold for the ion channel of interest, and in which the expression of other ion channels is largely confined to a few characterized ion channel types. Cells of this type include HEK-293 and RBL cells as well as F11 and HL5 cells. After choosing a target ion channel, cells are transfected with the ion channel of interest and clones are selected as described above. Alternatively, as in the case of F11 and HL5 cells, endogenous sodium channels can be used. After selection and characterization, cell clones are plated into multiwell microtiter plates and stained with voltage-sensitive dyes as described above. As previously, initial experiments are typically carried out in a 96-well multiwell plate, with an equal number of cells in each well. Generally columns of eight wells are simultaneously stimulated under identical conditions to provide statistically significant data on the variation in cellular response.

A number of assay approaches are possible depending on the expression level of the sodium channel of interest in the cell. For high levels of voltage-dependent sodium channel expression, the sodium current can be large enough to create a large transmembrane potential change after a single channel activation/inactivation sequence. In these cases small positive perturbations in the transmembrane potential created via electrical stimulation can be sufficient to activate enough sodium channels that the subsequent sodium ion entry depolarizes the entire cell thereby activating all the sodium channels. The stimulus field should typically be applied for a time long enough to activate the channels, but not so long as to interfere with the subsequent ion flux. After the cell transmembrane potential has re-polarized, the stimulation procedure can be repeated. Subsequent stimulation events can be identical to the first, or varied to examine time-dependent properties of the channels.

Typically one would start out with initial conditions using a biphasic square wave kernel of 500 µs per phase and an amplitude of 10 V/cm. One would then optimize the pulse amplitude (between 5 and 60 V/cm) and duration (between 0.1 and 1 ms). If necessary changes in the pulse shape could also be explored to determine if these resulted in more efficient electrical stimulation. The optimal stimulus parameters will yield the maximum cellular stimulation with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

Often it will be necessary to use cells whose expression of sodium channels is too low to give acceptable signal sizes from single stimuli. It may also be desirable to maintain a large signal over an extended period of time. In these cases, the cells can be given pulse trains as described for channels held above the activation potential. With biphasic stimulus pulses, the sodium channels can be activated independent of the starting transmembrane potential. By keeping the interpulse interval shorter than the membrane time constant, each stimulus will drive current into the cell until an equilibrium between inward and outward currents is established. This voltage deviation will be maintained as long as the stimulus train continues.

The stimulation protocols in this case are essentially the same as described for cells whose resting potential is above the inactivation threshold. In general, a series of initial experiments are conducted using a biphasic square wave kernel repeated at a regular rate for a fixed train duration. The pulse duration varies from about 1 µs to about 1 s, and more preferably from about 100 µs to about 20 ms. The pulse amplitude varies from 0 V/cm to about 60 V/cm, and more preferably from 10 V/cm to 50 V/cm. The frequency of stimulation varies between 0 Hz (i.e. a single pulse) and 100 kHz, and more preferably from 0 Hz to about 1 kHz. The pulse train varies between 0 s (i.e. a single pulse) and about 100 s, and more preferably between 0 s and 10 s. The optimal stimulus parameters will yield the maximum transmembrane potential changes (compared to cells with the channel blocked, or not present) and smallest coefficient of variation of the signal among the test wells, at the lowest electric field strength. After a particular set of parameters is chosen, a titration of staining concentrations for the voltage sensor dye(s) is typically performed as described above to further optimize the signal size and coefficient of variation of the responses. These procedures (dye concentrations, electric field strength, and stimulus duration and frequency) can be iterated to further optimize the signal.

ii. Potassium Channels

Voltage-dependent potassium channels repolarize nerve and muscle cells after action potential depolarization. They also play important regulatory roles in neural, muscular, secretory, and excretory systems. Most cells actively maintain a high intracellular potassium concentration, so that the reversal transmembrane potential for potassium is around −90 mV. Potassium typically flows out of the cell, so that opening more potassium-selective channels tends to drive the transmembrane potential more negative, in contrast to sodium channel opening that typically drives the transmembrane potential more positive.

A summary of the numerous potassium sub-types is presented in Table 2 below.

TABLE 2

Potassium Channel Sub-type Summary

| Channel Type | Sub-type/ Alternate names | Accession Number | Reference |
|---|---|---|---|
| ATP regulated | rKir1.1 (ROMK1) (rat) | U12541 | U.S. Pat. No. 5,356,775 |
| | hKir1.1 (ROMK1)(human) | | U.S. Pat. No. 5,882,873 |
| | Kir1.2 | U73191 | |
| | Kir1.3 | U73193 | |
| II. | β-cell | | U.S. Pat. No. 5,744,594 |
| III. | hβIR | | U.S. Pat. No. 5,917,027 |
| IV. | HuK$_{ATP}$-1 | | EP 0 768 379 A1 |
| Constitutively Active | Kir2.1(IRK1) | U12507 | U.S. Pat. No. 5,492,825 |
| | | | U.S. Pat. No. 5,670,335 |
| | Kir2.2 | X78461 | |
| | Kir2.3 | U07364 | |
| G-protein Regulated | Kir3.1 (GIK1, KGA) | U01071 | U.S. Pat. No. 5,728,535 |
| | Kir3.2 | U11859 | U.S. Pat. No. 5,734,021 |
| | Kir3.3 | U11869 | U.S. Pat. No. 5,744,324 |
| | Kir3.4 (CIR) | X83584 | U.S. Pat. No. 5,747,278 |
| | Kir4.1(BIR10) | X83585 | |
| | Kir5.1(BIR9) | X83581 | |
| | Kir6.1 | D42145 | |
| | Kir6.2 | D5081 | |
| | Kir7.1 | | EP 0 922 763 A1 |
| Voltage Regulated | | | |
| KCNA1 | hKv1.1 (RCK1, RBK1, MBK1, MK1, HuK1) | LO2750 | |
| KCNA2 | Kv1.2 (RBK2, RBK5, NGK1, HuKIV) | | |
| KCNA3 | Kv1.3 (KV3, RGK5, HuKIII, HPCN3, | | |
| KCNA4 | Kv1.4 (RCK4, RHK1, HuKII) | | |
| KCNA5 | Kv1.5 (KV1, HPCN1, HK2) | | |
| KCNA6 | Kv1.6 (KV2, RCK2, HBK2) | | |
| KCNA7 | Kv 1.7 (MK6, RK6, HaK6) | | U.S. Pat. No. 5,559,009 |
| Kv2 (Shab) | | | |
| KCNB1 | Kv2.1(DRK1, mShab) | M64228 | |
| KCNB2 | Kv2.2 (CDRK1) | | |
| | K channel 2 | | U.S. Pat. No. 5,710,019 |
| Kv3 (Shaw) | | | |
| KCNC1 | Kv3.1 (NGK2) | | |
| KCNC2 | Kv3.2 (RKShIIIA) | | |
| KCNC3 | Kv3.3 (KShIIID) | X60796 | |
| KCNC4 | Kv3.4 (Raw3) | | |
| Kv4 (Shal) | | | |
| KCND1 | Kv4.1 (mShal, KShIVA) | M64226 | |
| KCND2 | Kv4.2 (RK5, Rat Shal 1) | | |
| KCND3 | Kv4.3 (KShIVB) | | |
| | hKv5.1(IK8) | | WO 99/41372 |
| | Kv6.1 (K13) | | |
| | Kv7 | | |
| | Kv8.1 | | |
| | Kv9 | | |

TABLE 2-continued

Potassium Channel Sub-type Summary

| Channel Type | Sub-type/ Alternate names | Accession Number | Reference |
|---|---|---|---|
| Delayed Rectifier | KvLQT1 | AF000571 | U.S. Pat. No. 5,599,673 |
| | HERG (erg) | U04270 | PCT WO99/20760 |
| Calcium regulated | | | |
| $Ca^{2+}$ Regulated Big | | | |
| | BKCa (hSLO) | U11717 | |
| | HBKb3 (β-subunit) | | PCT WO99/42575 |
| | Maxi-K | | U.S. Pat. No. 5,776,734 |
| | | | U.S. Pat. No. 5,637,470 |
| $Ca^{2+}$ Regulated-small | | | |
| KCNN1 | SKCa1 | U69883 | |
| KCNN2 | SKCa2 | U69882 | |
| KCNN3 | SKCa3 | U69884 | |
| KCNN4 | SKCa4 (IKCa1) | | Muscle Nerve 1999 22(6) 742-50 |
| | TWIK1 | U33632 | |

Potassium channels show enormous diversity in terms of activation and inactivation time constants and voltage dependencies. In general, voltage-dependent potassium channels show voltage dependence similar to sodium channels, being closed at very negative potentials and opening above a certain threshold. Potassium channels may have multiple resting states, multiple inactivated states, and typically a single activated state. Unlike voltage-dependent sodium channels, transitions are allowed between most states. These transitions are activation (moving from a resting to the open state), deactivation (moving from the open state to a resting state), inactivation (moving from a resting or open state to an inactivated state), release from inactivation (moving from an inactivated state to a resting state), and flickering (moving from an inactivated state to the open state). There is a great diversity in the thresholds of the transitions, and in the voltage dependencies of the transition rates. Activation time constants range from 0.1 to 1000 ms with threshold activation potentials from −80 to +20 mV. Inactivation time constants range from 0.1 to infinity (i.e. no inactivation) with threshold potentials from −60 to 0 mV. Time constants for release from inactivation range from 0.5 ms to 100 ms with threshold potentials from −70 to 0 mV.

Stimulus protocols necessary to obtain measurable channel-dependent signals are somewhat dependent upon the specific properties of the channel in question. Because of the diversity in parameters in voltage-dependent potassium channels, the optimization of an electrical stimulation protocol may take several iterations.

During these experiments, the response will be compared for cells with active channels, and for cells in which the channels are pharmacologically blocked. If a suitable pharmacological agent is not available, the blocked state can be emulated with an un-transfected cell line. The optimal stimulus parameters will yield the smallest coefficient of variation of the difference in signals of the two cell populations.

(a) Assays using Direct Stimulation of the Potassium Channel (i) Voltage Regulated Potassium Channels Because potassium channels generate outward currents, activating the channels causes negative transmembrane potential changes. Under physiological conditions, the reversal potential for potassium is around −90 mV. Because cells expressing only a voltage-dependent potassium channel generally have resting potentials near the activation threshold, direct stimulation should work for those voltage-dependent potassium channels which have activation thresholds above about −50 mV. While small negative deflections in the transmembrane potential (less than 40 mV change) can be reliably detected using the FRET voltage-sensitive dyes, it is often preferable to perform high-throughput screens with larger signals.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest could be used. The labeling and measurement of cells with transmembrane potential dyes will generally be performed as described for sodium ion channels normally in the resting state.

The stimulation protocol will advantageously depolarize part of the plasma membrane long enough to activate the voltage-dependent potassium channels. Unlike the case for voltage-dependent sodium channels, voltage-dependent potassium channels will typically pass current during the depolarizing phase of the stimulus pulse. On the side of the cell where the transmembrane potential is driven in a negative direction, the potassium channels release from inactivation (if the channel in question experiences voltage-dependent inactivation). On the side of the cell where the transmembrane potential is driven in a positive direction, potassium channels activate and pass outward current. Thus, the stimulus pulse duration should not greatly exceed the inactivation time. The potassium current tends to drive the average transmembrane potential negative of the resting potential. After the stimulus pulse, the transmembrane potential will exponentially relax to the resting potential. By repeating the stimulus after a time shorter than the membrane time constant, the average cell membrane can be driven further negative. Using a train of stimuli, a large and sustained signal can be obtained.

A preferred stimulation protocol that achieves this effect is biphasic, so that ion channels present on both the extreme edges of the cells can participate in enabling potassium ion movement. Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum average transmembrane potential change (compared to cells with the channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

(h) Inward-Rectifier Potassium Channels

Contrary to its name, the function of the inward rectifier channel is not to allow potassium into the cell. Inward flow of potassium can only occur (1) when the transmembrane potential falls below the potassium equilibrium potentials, or (2) if the extracellular potassium concentration rises. Neither situation normally occurs, because (1) under normal physiological conditions, since potassium is the ion with the most negative reversal potential, no ionic current can drive the potential more negative than the potassium reversal potential, and (2) except under pathological conditions, the extracellular potassium concentration is tightly controlled. However, using electrical stimulation, parts of the cell membrane can be driven below $V_K$, promoting potassium ion entry into the cell. This will cause a net positive transmembrane potential change and can be detected as a positive signal. To develop and optimize an assay for blockers of the inward rectifier, one could therefore follow the following procedure.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest could be used. The labeling and measurement of cells with transmembrane potential dyes will generally be performed as described for sodium ion channels normally in the resting state.

A preferred stimulation protocol uses a biphasic kernel, so that ion channels present on both the extreme edges of the cells participate. Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum cellular stimulation (compared to cells with the channel blocked, or not present) with the smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

(c) Assays using a Voltage-Dependent Sodium Counter-Channel

This method involves the use of a cell line expressing the voltage-dependent potassium channel of interest and which also expresses a voltage-dependent sodium channel. In this method the approach is to use electrical stimulation protocols designed to specifically activate the voltage dependent sodium channel. In this case electrical stimulation causes sodium ions to enter the cell, causing a positive voltage change. The presence of the potassium channel of interest will tend to suppress the positive response of the sodium channel by allowing potassium ions to leave the cell. The assay takes advantage of the absence of outward current when a test chemical blocks the potassium channel, thereby restoring the large positive voltage response normally induced by activation of the sodium channels. The optimization of the balance of currents is important in this method to ensure that the assay is sensitive to potassium channel blockade. If the sodium current is too small relative to the potassium current, the dose-response curve for the potassium channel blocker will be shifted towards higher concentrations. For example, in the extreme case where the potassium current is 100 times larger than the sodium current, 99% of the potassium channels would have to be blocked in order to get a 50% response from the sodium channels.

Because this method involves driving a voltage-dependent sodium channel with repetitive pulses, the protocol development is essentially the same as described above for voltage-activated sodium channels in an inactivated state. Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation.

The optimal stimulus parameters will yield the maximum cellular stimulation (compared to cells with the channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

In this assay format, there will ideally be no (or a very small) response to stimulation in the absence of channel block, because the potassium current will counteract the sodium current. Therefore, to optimize the stimulus conditions, it will be necessary to compare responses with and without the activity of the potassium channel. Ideally, this will be accomplished using a selective blocker of the potassium channel. In those cases where such a blocker is yet unknown, it will be possible to use the cell line containing only the sodium counter-channel.

Because this assay format involves two ion channels, modulators of either channel will affect the voltage response. In this case, a hit (a blocker of the potassium channel) will restore the voltage response. The screening format automatically ignores compounds which block only the sodium channel. However, stimulation of the cells in the presence of compounds which block both channels will also result in no voltage deflection, suggesting that the compound is inactive.

Because compounds of this type may be of interest, a method to unmask them is also available. By performing the identical compound screen using the parent cell line, which contains the sodium channel but not the potassium channel, blockers of the sodium channel can be found. Compounds which are found to block the sodium channel can then be tested separately to find if they have activity against the potassium channel.

ii. Assay of Calcium Channels

Calcium channels are generally found in many cells where, among other functions, they play important roles in signal transduction. In excitable cells, intracellular calcium supplies a maintained inward current for long depolarizing responses and serves as the link between depolarization and other intracellular signal transduction mechanisms. Like voltage-gated sodium channels, voltage-gated calcium channels have multiple resting, activated, and inactivated states.

Multiple types of calcium channels have been identified in mammalian cells from various tissues, including skeletal muscle, cardiac muscle, lung, smooth muscle and brain, [see, e.g., Bean, B. P. (1989) Ann. Rev. Physiol. 51:367-384 and Hess, P. (1990) Ann. Rev. Neurosci. 56:337]. The different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed (Swandulla, D. et al., Trends in Neuroscience 14:46, 1991).

The cDNA and corresponding amino acid sequences of the $\alpha 1$, $\alpha 2$, $\beta$ and $\gamma$ subunits of the rabbit skeletal muscle calcium channel have been determined [see, Tanabe et al. (1987) Nature 328:313-318; Ruth et al. (1989) Science 245:1115-1118; and U.S. Pat. No. 5,386,025]. In addition, the cDNA and corresponding amino acid sequences of $\alpha 1$ subunits of rabbit cardiac muscle [Mikami, A. et al. (1989) Nature 340:230-233] and lung [Biel, M. (1990) FEBS Letters 269:409-412] calcium channels have been determined. In addition, cDNA clones encoding a rabbit brain calcium channel (designated the BI channel) have been isolated [Mori, Y. et al. (1991) Nature 350:398-402].

Partial cDNA clones encoding portions of several different subtypes, referred to as rat brain class A, B, C and D, of the calcium channel $\alpha 1$ subunit have been isolated from rat brain cDNA libraries [Snutch, T. et al. (1990) Proc. Natl. Acad. Sci. USA 87:3391-3395]. More recently full-length rat brain class A [Starr, T. et al. (1991) Proc. Natl. Acad. Sci. USA 88:5621-5625] and class C [Snutch, T. et al. (1991) Neuron 7:45-57] cDNA clones have been isolated. Although the amino acid sequence encoded by the rat brain class C DNA is approximately 95% identical to that encoded by the rabbit cardiac muscle calcium channel $\alpha 1$ subunit-encoding DNA, the amino acid sequence encoded by the rat brain class A DNA shares only 33% sequence identity with the amino acid sequence encoded by the rabbit skeletal or cardiac muscle $\alpha 1$ subunit-encoding DNA. A cDNA clone encoding another rat brain calcium channel $\alpha 1$ subunit has also been obtained [Hui, A. et al. (1991) Neuron 7:35-44]. The amino acid sequence encoded by this clone is approximately 70% homologous to the proteins encoded by the rabbit skeletal and cardiac muscle calcium channel DNA. A cDNA clone closely related to the rat brain class C $\alpha 1$ subunit-encoding cDNA and sequences of partial cDNA clones closely related to other partial cDNA clones encoding apparently different calcium channel $\alpha 1$ subunits have also been isolated [see Snutch, T. et al. (1991) Neuron 7:45-57; Perez-Reyes, E. et al. (1990) J. Biol. Chem. 265:20430; and Hui, A. et al. (1991) Neuron 7:35-44].

For known calcium channels that have been characterized, activation time constants range from 0.1 to 10 ms with threshold potentials from −80 to −20 mV. Inactivation time constants range from 0.1 to ∞ (i.e. no inactivation) with threshold potentials from −60 to −20 mV. Time constants for release from inactivation range from 0.5 ms to 100 ms with threshold potentials from −70 to −40 mV.

Choice of cell line and induction of voltage-dependent calcium currents are performed using the general guidelines and approaches discussed above for sodium channels.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest could be used. The labeling and measurement of cells with transmembrane potential dyes will generally be performed as described for sodium ion channels normally in the resting state. Alternatively, the cells can be loaded with calcium-sensitive fluorescent dyes such as Calcium Green, fluo3-AM, or indo-1.

In cells with low background currents, strong inward calcium currents can be generated by driving portions of the membrane negative enough to release the channels from inactivation. Then by reversing or releasing the external electric field, the channels are exposed to potentials which activate the channels and permit calcium current to flow into the cell. The reversal potential for calcium in most cells is generally +60 to +100 mV, so large voltage changes due to calcium influx are possible. We can use either membrane-bound voltage-sensitive dyes or intracellular calcium dyes to monitor the activity of the cells. Due to the similarity in properties of calcium and sodium channels, the same general assay optimization procedures outlined above for sodium channels will apply to calcium channels.

Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum cellular stimulation (compared to cells with the channel blocked, or not present) with the smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

During these experiments, the response will be compared for cells with active channels, and for cells in which the channels are pharmacologically blocked. If a suitable pharmacological agent is not available, the blocked state can be emulated with an un-transfected cell line. The optimal stimulus parameters will yield the smallest coefficient of variation of the difference in signals of the two cell populations.

iii. Assay of Voltage-Dependent Chloride Channels

Chloride channels are found in the plasma membranes of virtually every cell in the body. Chloride channels mediate a variety of cellular functions including regulation of transmembrane potentials and absorption and secretion of ions across epithelial membranes. When present in intracellular membranes of the Golgi apparatus and endocytic vesicles, chloride channels also regulate organelle pH. For a review, see Greger, R. (1988) Annu. Rev. Physiol. 50:111-122.

Three distinct classes of chloride channels are apparent based on their type of regulation and structural conformation, Table 3. The first class includes the GABA and Glycine receptor super families, the second class includes the CFTR (Cystic fibrosis Transmembrane Conductance Regulator) and the third class includes the voltage regulated chloride channels.

TABLE 3 iv. Chloride Channel Sub-type Summary

| Channel Type | Sub-type | Tissue Distribution | Reference |
|---|---|---|---|
| Ligand gated | GABA$_A$ Receptor family | CNS & PNS | Synapse 21, 189-274 (1995) |
| | Glycine Receptor family | CNS & PNS | Trends Neurosci. 14, 458-461 (1991) |
| cAMP regulated | CFTR | Epithelial tissues | Science 245, 1066-1073 (1989) |
| Voltage regulated | ClC-1 | Skeletal Muscle | Nature 354, 301-304 (1991) |
| | ClC-2 | Ubiquitous | Nature 356, 57-60 (1992) |
| | ClC-Ka | Kidney | J. Biol. Chem. 268, 3821-3824 (1993) |
| | ClC-Kb | Kidney | P.N.A.S. 91, 6943-6947 (1994) |
| | ClC-3 | Broad, e.g. Kidney & Brain | Neuron 12, 597-604 (1994) |
| | ClC-4 | Broad, e.g. Kidney & Brain | Hum. Mol. Genet. 3 547-552 (1994) |
| | ClC-5 | Mainly Kidney | J. Biol. Chem. 270, 31172-31177 (1995) |
| | ClC-6 | Ubiquitous | FEBS. Lett. 377, 15-20 (1995) |
| | ClC-7 | Ubiquitous | FEBS. Lett. 377, 15-20 (1995) |

In contrast to ions like sodium and especially calcium, the electrochemical gradient of chloride across the plasma membrane is generally not far from equilibrium. Thus, at the resting potential of cells, the opening of chloride channels will not lead to large excursions of the plasma membrane voltage or dramatic changes in intracellular chloride concentrations. Because electrical stimulation typically generates symmetrical voltage changes across the cell membrane, no net chloride flux can be generated unless the conductivity of the channel is non-linear. For a linear leak conductance, a uniform electric field will drive chloride into the cell on one side and out of the cell on the other side.

Direct electrical stimulation of chloride channels which have non-linear conductance curves (rectifiers) or voltage-activated gating can generate net ion fluxes, which in turn will cause detectable transmembrane potential changes. Depending upon the voltage dependence of the conductance and gating, the transmembrane potential change can be either positive or negative. For typical chloride channels (that activate at elevated potentials and close at more negative potentials) and for outward rectifiers, chloride will flow into the cell and drive the transmembrane potential negative. For inward rectifiers, chloride will be driven out of the cell and the transmembrane potential will be driven positive.

Due to the small difference between the chloride reversal potential and the resting transmembrane potential, direct stimulation of a voltage-gated chloride channel may result in insufficient transmembrane potential changes. Assays for these ion channels can then be developed using co-expression and electrical stimulation of a sodium or potassium counter-channel in order to produce an inward or outward current. Presence or absence of the chloride current can then be determined by the absence or presence of a transmembrane potential change when the counter-channel is electrically stimulated.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest (or the counter-channel) could be used. The labeling and measurement of cells with transmembrane potential dyes will generally be performed as described for sodium ion channels normally in the resting state.

Typically one would start out with initial conditions using a biphasic square wave kernel of 5 msec per phase and amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum cellular stimulation (compared to cells with the channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

(a) During these Experiments, the Response will be Compared for Cells with Active Channels, and for Cells in which the Channels are Pharmacologically Blocked. If a Suitable Pharmacological Agent is not Available, the Blocked State can be Emulated with an Un-Transfected Cell Line. The Optimal Stimulus Parameters will Yield the Smallest Coefficient of Variation of the Difference in Signals of the Two Cell Populations.

v. Assay of Ligand Dependent Channels

The ligand-dependent ion channel family is large and diverse. Ligand-dependent ion channels open in response to the binding of specific molecules. They typically mediate fast synaptic transmission between neurons, and from neurons to muscle cells. They also mediate slow synaptic transmission and control a variety of regulatory mechanisms. Ligand-gated ion channels are generally only charge-selective; that is, they permit the flow of a range of either anions or cations but have little specificity. They have enormous variation in their activation, deactivation, and desensitization kinetics, all of which can vary from submillisecond to second time constants.

When the ligand binds to the receptor of the channel, the channel undergoes one or more conformational changes to activate the channel. If the ligand is removed from the bathing saline, the bound ligands dissociate and the channel closes. If the ligand remains in the bathing saline, some channels desensitize by retaining the ligand but moving into a different conformational state in which the channel is closed. Equilibrium distributions between the activated, deactivated, and desensitized states vary greatly among channels.

In current assay formats, the transmembrane potential of the cells is monitored during an addition of ligand. The sudden increase in conductance when the channel opens drives the transmembrane potential towards a new reversal potential. Unfortunately, for many ligand-gated channels, the new reversal potential is usually within 15 mV of the resting potential. This small change is sufficient to use for signaling within cells, but it makes pharmacological assays difficult.

In an electrical stimulation assay for ligand-gated ion channels, one approach is to co-express a voltage-gated sodium counter channel with the ligand gated ion channel of interest. This approach allows us to modulate the transmembrane potential via electrical stimulation. If the test compounds are added to the cells during or prior to electrical stimulation, the method enables an analysis of whether the ligand gated channel is open or closed. If the ligand-gated channels are open, the high resting conductance of the cell will suppress the voltage response to electrical stimulation. If, however, the ligand-gated channels are blocked, the cells will have a large response to electrical stimulation. The large amount of flexibility in electrical stimulation parameters should allow us to assay for a large range in resting conductances. This is important in the case of ligand-gated channels, because the resting conductance in the presence of ligand is very sensitive to the equilibrium desensitization. Accounting for desensitization and variations in channel expression, we may have resting membrane resistances ranging anywhere from 10 M$\Omega$ to 10 G$\Omega$. With rat brain type IIa sodium channels as the counter channel, we can cover this entire range. It should also be possible to screen for both agonists and antagonists. By choosing stimulation parameters such that the response is half-size, agonists will reduce the response while antagonists will increase it. Better screening windows may be obtained by stimulating at higher (agonist assay) or lower (antagonist assay) frequencies. Note that modulators of the channel conductance, open time, desensitization, and deactivation will all be detected.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest (or the counter-channel) could be used. The labeling and measurement of cells with transmembrane potential dyes will generally be performed as described for sodium ion channels normally in the resting state.

Typically one would start out with initial conditions using a biphasic square wave kernel of 5 msec per phase and amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum cellular stimulation (compared to cells with the ligand-gated channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

During these experiments, the response will be compared for cells with active channels, and for cells in which the channels are pharmacologically blocked. If a suitable pharmacological agent is not available, the blocked state can be emulated with an un-transfected cell line. The optimal stimulus parameters will yield the smallest coefficient of variation of the difference in signals of the two cell populations.

vi. Assay of Passive Channels

Many channels have slow or no voltage-activated conductance changes. Prime examples are the some of the channels implicated in cystic fibrosis, particularly the cystic fibrosis transmembrane regulator (CFTR, a chloride channel), the epithelial sodium channel (ENaC) and 4 TM potassium channel family members (Wang et al. Ann. N. Y. Acad. Sci. 868: 286-303, 1999). A small molecule which acts as an agonist for either of these channels would be a candidate for a drug which alleviates cystic fibrosis. Currently, there is no convenient workable high throughput screening method for channels of this type.

The proposed assay format for ion channel targets of this type involves a cell expressing the leak channel of interest in a cell which also expresses a voltage-dependent sodium channel. The channel of interest is cloned into a cell with a voltage-dependent sodium channel. The presence of the passive current will suppress the positive response of the sodium channel when the cells are stimulated. Blocking the passive channel will restore the large positive voltage response. Optimization of the balance of currents will be important in this method. Wild-type CHO cell may be useful for this purpose, although a cell with larger sodium currents (either endogenous or engineered) would be preferable. If the sodium current is too small relative to the potassium current, the dose-response curve for the passive channel blocker will be shifted towards higher concentrations. For example, in the extreme case where the passive current is 100 times larger than the sodium current, 99% of the passive channels would have to be blocked in order to get a 50% response from the sodium channels.

Preferred cell types include those cells that express a minimal level of other ion channels, such as CHO-K1, CHL, and LTK(−). The transfection and selection of clones expressing ion channels of interest will generally be performed as described above for sodium ion channels normally in the resting state. Alternatively, a cell line which endogenously expresses the channel of interest (or the counter-channel) could be used. The labeling and measurement of cells with transmembrane potential dyes will generally be performed as described for sodium ion channels normally in the resting state.

A preferred stimulation protocol uses a biphasic kernel. In general, a series of initial experiments are conducted using a biphasic square wave kernel repeated at a regular rate for a fixed train duration. The pulse duration varies from about 1 µs to about 1 s, and more preferably from about 100 µs to about 20 ms. The pulse amplitude varies from 0 V/cm to about 60

V/cm, and more preferably from 10 V/cm to 50 V/cm. The frequency of stimulation varies between 0 Hz (i.e. a single pulse) and 100 kHz, and more preferably from 0 Hz to about 1 kHz. The pulse train varies between 0 s (i.e. a single pulse) and about 100 s, and more preferably between 0 s and 10 s.

Typically one would start out with initial conditions using a biphasic square wave kernel of 5 msec per phase and an amplitude of 25 V/cm. The kernel would be repeated at a regular rate of about 20 Hz for a total train duration of about three seconds. One would then optimize the pulse amplitude, duration, and then frequency. If necessary changes in the pulse shape could also be explored to determine if these resulted in more efficient electrical stimulation. The optimal stimulus parameters will yield the maximum cellular stimulation (compared to cells with the ligand-dependent channel blocked, or not present) with smallest coefficient of variation of the signal among the different test wells, at the lowest electric field strength, and at the lowest duty cycle for passage of current through the electrodes. After a particular set of parameters is chosen, a titration of staining concentrations for the voltage sensor dye(s) should be performed as described above, to further optimize the signal size and coefficient of variation of the responses. These procedures (dye concentrations, electric field strength, and stimulus duration and frequency) can be iterated to further optimize the signal.

It should be possible to screen for both agonists and antagonists. By choosing stimulation parameters such that the response is half-maximal, agonists will reduce the response while antagonists will increase it. Better screening windows may be obtained by stimulating at higher (agonist assay) or lower (antagonist assay) frequencies.

During these experiments, the response will be compared for cells with active channels, and for cells in which the channels are pharmacologically blocked. If a suitable pharmacological agent is not available, the blocked state can be emulated with an un-transfected cell line. The optimal stimulus parameters will yield the smallest coefficient of variation of the difference in signals of the two cell populations. The present invention also includes methods for the quantitative determination of cellular and ion channel parameters, and for the quantification of the pharmacological effects of test compounds on these parameters using electrical stimulation.

b. Quantitative Measurements of Membrane Resistances

After the electrical stimulus ends, the cell transmembrane potential relaxes to a new resting potential. In the case of voltage-dependent channel assays, the channels will generally close or inactivate, and the final resting equilibrium potential will be the same as before the stimulus. In most cases, the charge built up on the membrane capacitance will dissipate exponentially through the membrane resistance. The membrane time constant is simply the product of the membrane capacitance and the membrane resistance, $\tau_m = R_m C_m$. It can be readily determined by measuring the membrane capacitance and the membrane time constant.

The average membrane capacitance for cells commonly used in these assays is independent of the exogenous channel, and can easily be measured by patch clamp methods. The membrane time constant can be readily measured by measuring the rate of decay of the transmembrane potential and fitting this data to an exponential decay function. Thus by dividing the membrane time constant by the average membrane capacitance for the given cell type, we can quantitatively determine the resting or leak membrane resistance.

A similar analysis can be made to quantitatively measure the membrane resistance while a voltage-dependent channel is open. During the electrical stimulation, the transmembrane potential will also relax approximately exponentially towards a new equilibrium potential. Thus, the membrane time constant of the voltage change at the beginning of the stimulus constitutes a measurement of the time-averaged membrane resistance. Using appropriate scaling factors to account for the fraction of the time that the channel is actually open, we can make a quantitative estimate of the open-channel membrane resistance.

i. Measurement of Release from Inactivation Time Constant

Opening an inactivation ion channel requires holding the transmembrane potential below a threshold for a time on the order of several milliseconds. This release from inactivation has important physiological implications. For example, release from inactivation forces a refractory period which prevents back-propagation of action potentials, and limits the maximum firing rates of neurons. Pharmacological manipulation of this property may be therapeutically relevant c. Using Repetitive Electrical Stimulation, we can Estimate the Average Release from Inactivation Time. This can be Done by using Electric Field Pulses of Variable Width. When the Pulse Width Falls Below the Release from Inactivation Time, Fewer Channels will be Activated and the Transmembrane Potential Rise in Response to the Stimulation will Drop.

d. Measurement of the Open Channel Time

The open channel time $\tau_{open}$ is a function of the inactivation properties of the channel. We can detect pharmacological manipulation of this parameter in a medium- to high-throughput mode by stimulating at very high frequency. For example, consider an assay for a voltage-dependent sodium channel using the multiple stimulus method. With a fixed monophasic square wave stimulus kernel repeated at a steady rate, the voltage response increases as the stimulus repetition rate increases. This is because the sodium channel spends relatively more time open at higher frequency. However, if the inter-pulse interval becomes shorter than the open channel time, the activated sodium channels will be driven negative, and thereby deactivated, by the subsequent stimulus pulse. The stimulation burst frequency at which the response flattens is related to the open channel time.

e. Electrical Stimulation as an Extracellular Current Clamp Device

In whole-cell recording, current clamp is a mode in which command currents can be driven into the cell while recording the transmembrane potential. Although patch-clamp recording is extremely precise, it is a very low-throughput technique. At an absolute maximum under perfect conditions, a highly trained scientist could determine cellular parameters at a rate of about ten cells per hour. Often, the level of detail obtained with the patch-clamp technique is not necessary for drug screening, but there is currently no method for exchanging detail for speed. High speed is absolutely crucial for screening large compound libraries.

The electric field stimulation techniques discussed herein permit a new type of current-clamp electrophysiology which we call extracellular current clamp. Voltage-dependent channels can be used to drive command currents into cell cultures, allowing determination of several cellular and channel properties. Extracellular current clamp has a very high throughput, so that it will be possible to obtain high information content of the pharmacological effects of compound libraries against specific ion channel targets. The pharmacology and physiology of a channel can be studied directly, or the channel can be used as a current generator for the study of the cell membrane itself or a second ion channel.

While the ultimate precision of the microscopic parameters obtainable with the extracellular current clamp cannot yet approach the patch-clamp method, we now have the ability to exchange information content for throughput. That is, the degree of precision at which to make measurements can be arbitrarily set. With a single set of stimulus parameters, large libraries can be screened for potential interesting compounds. A medium throughput secondary screen using a titration of compound concentrations can be performed on the hits to determine potency and specificity. Finally, we can determine such therapeutically relevant properties such as use-dependence and mechanism of action by varying the stimulus parameters in the presence of the compounds. At every stage, the measurements are automatically averaged over many cells, greatly reducing uncertainties associated with cell-to-cell variability.

There are at least two additional advantages of the extracellular current clamp as compared to patch-clamp analysis. First, the integrity of the cell membrane is not altered during electric field stimulation. The intracellular fluid is completely replaced with pipette solution during whole-cell patch clamp recording. Many proteins within the cell, including ion channels, are extremely sensitive to modulators, intracellular messengers, and the ionic environment. The components of the cytoplasm are only crudely known, so the soluble components in the intracellular space are always altered. Therefore, the 'normal' physiological state of the cell is only approximated during whole-cell patch clamp analysis, but remains intact when using extracellular current clamp.

Second, most cells experience dramatic alterations in gene expression and behavior when in contact with other cells. Because most cells also make gap junctional connections with neighboring cells, whole-cell patch clamp analysis is only reliable when cells are completely isolated from each other. Extracellular current clamp can be used on cells independently of their degree of confluence, so the cells may be more physiologically relevant. We can use extracellular current clamp to find out if there are any effects of cell-cell contact on channel electrophysiology. Then, in conjunction with gene expression analysis, we can relate these changes to regulatory components of the cell.

f. Electrical Stimulation as an Extracellular Voltage Clamp Device

In voltage-clamp, the transmembrane potential of the cell is controlled while monitoring the current flow. Voltage clamp is generally achieved by adding a feedback loop to a current clamp circuit. In the case of the whole-cell method, this can easily be achieved with the use of two pipettes simultaneously attached to the same cell. One pipette passes a command current, while the other senses the voltage. A feedback circuit compares the measured voltage with the command voltage, and adjusts the command current accordingly. Generally, because the cell membrane resistance is large compared to the access resistance of the pipette, the same pipette can be used to command the current and measure the voltage. Compared to current clamp, voltage clamp is generally a more powerful method for electrophysiological analysis. Ion channels are extremely sensitive to transmembrane potential, so that analysis of data is far more straightforward when dealing with current measurements at a fixed voltage.

Extracellular current clamp can be converted to a voltage clamp method by adding a feedback loop between the voltage measurement (the fluorescence of the sensor dye) and the current generator (the stimulus parameters). In this case, a transmembrane potential dye with sufficient speed is required. The dye combination CC2-DMPE/DiSBAC$_6$(3) has a submillisecond time constant and should be sufficiently fast to capture all but the fastest cellular events. Based upon the difference of the command voltage and the transmembrane potential measurements, a computer will alter the stimulus parameters. The stimulus parameters are related to the current driven into the cell, so we can determine the time course of the current as a function of the command voltage. This method should prove useful in determining the mechanism of action of pharmacological agents upon ion channels targets.

g. Assays for Intracellular Compartments

The stimulation methods described herein can also be used to modulate the transmembrane potentials of intracellular organelles that have phospholipid membranes, including the mitochondria and the nucleus. This can be accomplished by first increasing the conductance of the plasma membrane either by electropermeablization or through the addition of ionophores such as valinomycin or gramicidin A. Then, the intracellular space is no longer insulated from the applied electric field. This allows an electric field applied to the saline to generate transmembrane potential changes across the membranes of intracellular organelles. Then, by staining the cells with dyes which are sensitive to the ion concentration or transmembrane potential, and which are targeted only to the specific organelle membrane of interest, the methods presented herein can be used to modulate and assay the ion channels of these organelles. Targeting can be achieved, for example via the use of a naturally fluorescent protein containing suitable subcellular location signals as are known in the art.

2. Introduction of Exogenous Molecules

Dielectric breakdown of mammalian cell membranes occurs if the electric potential across the membrane exceeds about 200 mV (Teissie and Rols, 1993, Biophys. J. 65:409-413). When the membrane breaks down, pores are formed through the membrane, bridging the intracellular and extracellular spaces. The number and size of the pores increases with increasing transmembrane potentials (Kinoshita and Tsong, 1977, Nature 268:438-441). Increasing the electric field strength above about 60 V/cm on typical mammalian cell lines can electropermeablize the cells. At relatively low fields, small pores are created in the cell membrane which apparently are large enough to admit small ions, but not large enough to admit molecules as large as DNA (Tsong, 1991, Biophys. J. 60:297-306). These pores totally depolarize the cell, driving the transmembrane potential to near zero. By electropermeablizing cells and monitoring the transmembrane potential change with a voltage-sensitive dye, the present invention can be used to determine the resting transmembrane potential of a cell. This will be useful for determining pharmacological interactions with cells or ion channels, either as a primary or a secondary screen. For example, in a compound screen against a voltage-dependent sodium channel, one could perform a multiple stimulus protocol to determine channel activity. Then, by following with a permeablizing protocol, one could determine whether or not the cell membrane had a normal resting potential in the presence of the compound.

Additionally, using a highly polarized cell line such as RBL cells, voltage sensitive dyes could be easily calibrated by electropermeablization. The starting transmembrane potential under various conditions (for example, various concentrations of extracellular potassium), and the final transmembrane potential after electropermeablization is zero.

Additionally, the size of the pores created by electropermeablization increases as a function of the applied electric field. Below 50 V/cm, no pores are created. Between about 60 V/cm and 100 V/cm, pores large enough to admit monovalent ions are created. Above around 600 V/cm, pores large enough to admit DNA are created (Tsong, 1991, Biophys. J. 60:297-306). Thus, this invention can be used to create pores of defined size in the cell membranes, in a high-throughput manner. This could be useful for many applications, including delivery to the intracellular space of impermeant ions, impermeant test compounds or other modulators, DNA or RNA for the purpose of transient or stable transfection, and fluorescent or other indicator dyes.

3. Drug Discovery and Screening a. Drug Screening

The present invention provides for the reliable detection of test compounds that modulate ion channel function that is significantly more versatile and robust than previous assay systems. Importantly, the present invention provides the ability to modulate the transmembrane potential in intact cells without the requirement of pharmacological agents, or membrane destruction, and loss of intracellular contents, as in patching clamping. By providing the ability to externally modulate the transmembrane potential of living cells, the present invention enables a wide variety of ion channels to be assayed.

Furthermore, this ability to modulate precisely the voltage dependent state of an ion channel, has important advantages for drug discovery where it provides the opportunity to screen for compounds that interact preferentially with one state, (i.e. use-dependent blockers). For example, several known therapeutically useful drugs (including anti-arrhythmics, anti-convulsants, and local anesthetics) are known to function as use-dependent blockers of voltage-dependent sodium and/or calcium channels. In each case, total blockade of the targeted channel would typically result in death. Certain conditions, such as chronic pain, arrhythmia, and convulsions occur when cells become over-active. These conditions can be alleviated or eliminated by blocking the channels if they begin to open too often. Compounds that are capable of blocking the channel, but which bind preferentially to the activated or inactivated states(s) rather than the resting state(s), can reduce the excitability of muscle and neurons. These drugs are effective because they do not affect the channel under normal circumstances, but block it only when necessary to prevent hyper-excitability. However existing methods of analysis that are compatible with high throughput screening do not provide the ability to routinely control the activation state of the ion channel in real time.

In particular, the present invention provides for a method for screening the effect of a test compound on an ion channel in a defined functional state within a cell. The method involves modulating the transmembrane potential of the cell via the use of repetitive electrical stimulation to cycle the ion channel of interest through its activation cycle and to set the transmembrane potential to a desired level suitable for a specific activation state, or transition between states. Then, during or after this process a test compound is added to the cell, and the transmembrane potential is measured.

Typically the results obtained in the presence of the test compound will be compared to a control sample incubated in the absence of the test compound. Control measurements are usually performed with a sample containing all components and under the same stimulation conditions, as for the test sample except for the putative drug. Additional control studies can be carried out with the ion channel in another voltage dependent state to specifically identify state specific test compounds. Detection of a change in transmembrane potential in the presence of the test agent relative to the control indicates that the test agent is active and specific on the ion channel in that state, or during the transition from one state to another.

Transmembrane potentials can be also be determined in the presence or absence of a pharmacologic agent of known activity (i.e., a standard agent) or putative activity (i.e., a test agent). A difference in transmembrane potentials as detected by the methods disclosed herein allows one to compare the activity of the test agent to that of the standard agent. It will be recognized that many combinations and permutations of drug screening protocols are known to one of skill in the art and they may be readily adapted to use with the present inventions disclosed herein to identify compounds, which affect ion channels and or transmembrane potentials. Use of the present inventions in combination with all such methods are contemplated by this invention.

In another aspect the present invention includes the use of a second ion channel in conjunction with electrical stimulation methods described, herein to set the resting, or stimulated transmembrane potential to a predefined value thereby providing for the ability to assay a first ion channel of interest. In one embodiment the second ion channel is a voltage regulated sodium or calcium channel which enables the generation of sustained positive transmembrane potentials. In another embodiment the second ion channel is a voltage regulated potassium channel, enabling the generation of negative transmembrane potentials. The use of these second ion channels enables the electrical stimulation method to be used to set the transmembrane potential to virtually any predefined level.

Because this assay format involves two ion channels, modulators of either channel will affect the voltage response. In this case additional control studies may be carried out with the parental cell line expressing only the second ion channel used to set the transmembrane potential. Compounds that block the first ion channel can then be re-tested separately to find out if they have activity against the second ion channel.

Typically the test compounds screened will be present in libraries of related or diverse compounds. The library can have individual members that are tested individually or in combination, or the library can be a combination of individual members. Such libraries can have at least two members, preferably greater than about 100 members or greater than about 1,000 members, more preferably greater than about 10,000 members, and most preferably greater than about 100,000 or 1,000,000 members.

i. Selectivity and Toxicology of Candidate Modulators

Once identified, candidate modulators can be evaluated for selectivity and toxicological effects using known methods (see, Lu, *Basic Toxicology, Fundamentals, Target Organs, and Risk Assessment*, Hemisphere Publishing Corp., Washington (1985); U.S. Pat. No. 5,196,313 to Culbreth (issued Mar. 23, 1993) and U.S. Pat. No. 5,567,952 to Benet (issued Oct. 22, 1996).

For example primary cell lines, or tissue slices can be used to screen for the effect of the candidate modulator on the response of the ion channel of interest in its native physiological context. For example, to screen for drugs that exhibit specific, and/or selective effects on heart cells it may be preferable to use myocytes or other in vitro cell culture model cell lines. In this case, a primary screen could be completed in a myocyte derived cell line to identify compounds that either shorten, prolong or block electrically-induced action potentials.

The secondary screen would then be designed to identify compounds that exhibit potentially adverse effects on the body. For example, this can be accomplished by screening for the effects of the candidate drug on electrically excitable tissues such as heart or neuronal tissues, or immortalized cell cultures derived from these tissues. These tissues play critical roles within an organism and any undesired effect of the candidate drug on the ability of these tissues to be electrically stimulated would be predicted to create potential serious side effects when administered. As a consequence, active compounds that also impaired the ability of these tissues to function could be eliminated from consideration as a drug candidate at an early stage, or have medicinal chemistry performed to reduce the side effects.

Additional toxicological analysis of candidate modulators can be established by determining in vitro toxicity towards a cell line, such as a mammalian (preferably human) cell line. Candidate modulators can be treated with, for example, tissue extracts, such as preparations of liver, such as microsomal preparations, to determine increased or decreased toxicological properties of the chemical after being metabolized by a whole organism, or via their ability to be degraded via Cytochrome P450 systems as described in commonly owned U.S. patent application Ser. No. 09/301,525, filed Apr. 28, 1999, U.S. patent application Ser. No. 09/301,395 filed Apr. 28, 1999 and U.S. application Ser. No. 09/458,927 filed Dec. 10, 1999. The results of these types of studies are often predictive of toxicological properties of chemicals in animals, such as mammals, including humans.

The toxicological activity can be measured using reporter genes that are activated during toxicological activity or by cell lysis (see WO 98/13353, published Apr. 2, 1998). Preferred reporter genes produce a fluorescent or luminescent translational product (such as, for example, a Green Fluorescent Protein (see, for example, U.S. Pat. No. 5,625,048 to Tsien et al., issued Apr. 29, 1998; U.S. Pat. No. 5,777,079 to Tsien et al., issued Jul. 7, 1998; WO 96/23810 to Tsien, published Aug. 8, 1996; WO 97/28261, published Aug. 7, 1997; PCT/US97/12410, filed Jul. 16, 1997; PCT/US97/14595, filed Aug. 15, 1997)) or a translational product that can produce a fluorescent or luminescent product (such as, for example, beta-lactamase (see, for example, U.S. Pat. No. 5,741,657 to Tsien, issued Apr. 21, 1998, and WO 96/30540, published Oct. 3, 1996)), such as an enzymatic degradation product. Cell lysis can be detected in the present invention as a reduction in a fluorescence signal from at least one photon-producing agent within a cell in the presence of at least one photon reducing agent. Such toxicological determinations can be made using prokaryotic or eukaryotic cells, optionally using toxicological profiling, such as described in PCT/US94/00583, filed Jan. 21, 1994 (WO 94/17208), German Patent No 69406772.5-08, issued Nov. 25, 1997; EPC 0680517, issued Nov. 12, 1994; U.S. Pat. No. 5,589,337, issued Dec. 31, 1996; EPO 651825, issued Jan. 14, 1998; and U.S. Pat. No. 5,585,232, issued Dec. 17, 1996).

Alternatively, or in addition to these in vitro studies, the bioavailability and toxicological properties of a candidate modulator in an animal model, such as mice, rats, rabbits, or monkeys, can be determined using established methods (see, Lu, supra (1985); and Creasey, *Drug Disposition in Humans, The Basis of Clinical Pharmacology*, Oxford University Press, Oxford (1979), Osweiler, *Toxicology*, Williams and Wilkins, Baltimore, Md. (1995), Yang, *Toxicology of Chemical Mixtures; Case Studies, Mechanisms, and Novel Approaches*, Academic Press, Inc., San Diego, Calif. (1994), Burrell et al., *Toxicology of the Immune System; A Human Approach*, Van Nostrand Reinhld, Co. (1997), Niesink et al., *Toxicology; Principles and Applications*, CRC Press, Boca Raton, Fla. (1996)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the therapeutic utility of a candidate modulator in vivo.

ii. Efficacy of Candidate Modulators

Efficacy of a candidate modulator can be established using several art-recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., Antimicro. Agents Chemother. 41:1082-1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, J. Bone Joint Surg. (Br) 55:197-205 (1973)). Hydrocortisone, which is approved for use in humans to treat arthritis, is efficacious in this model which confirms the validity of this model (see, McDonough, Phys. Ther. 62:835-839 (1982)). When choosing an appropriate model to determine efficacy of a candidate modulator, the skilled artisan can be guided by the state of the art to choose an appropriate model, dose, and route of administration, regime, and endpoint and as such would not be unduly burdened.

In addition to animal models, human clinical trials can be used to determine the efficacy of a candidate modulator in humans. The USFDA, or equivalent governmental agencies, have established procedures for such studies (see, www.fda.gov).

iii. Selectivity of Candidate Modulators

The in vitro and in viva methods described above also establish the selectivity of a candidate modulator. The present invention provides a rapid method of determining the specificity of the candidate modulator. For example, cell lines containing related ion channel family members can be used to rapidly profile the selectivity of a test chemical with respect both to its ability to inhibit related ion channels, and their relative ability to modulate different voltage dependent states of the ion channels. Such a system provides for the first time the ability to rapidly profile large numbers of test chemicals in order to systematically evaluate in a simple, miniaturized high throughput format the ion channel selectivity of a candidate modulator.

iv. An Identified Chemical, Modulator, or Therapeutic and Compositions

The invention includes compositions, such as novel chemicals, and therapeutics identified by at least one method of the present invention as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, 26 Dec. 1991), encoded peptides (PCT Publication No. WO 93/20242, 14 Oct. 1993), random bio-oligomers (PCT Publication WO 92/00091, 9 Jan. 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909-6913 (1993)), vinylogous polypeptides (Hagihara et al., J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217-9218 (1992)), analogous organic syntheses of small compound libraries (Chen, C. et al., J. Amer. Chem. Soc. 116:2661 (1994)), oligocarbamates (Cho, C. Y. et al., Science 261: 1303 (1993)), and/or peptidyl phosphonates (Campbell, D. A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the identified compositions in a pharmaceutical composition comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, acsorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode or administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 µg/kg and 100 mg/kg body weight, and preferably between about 100 µg/kg and 10 mg/kg body weight. Administration is preferably oral on a daily basis.

The exact formulation, route of administration and dosage can be chosen by the individual physician in view of the patient's condition. (See e.g., Fingl et al., in *The Pharmacological Basis of Therapeutics,* 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping, or lyophilizing processes. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

V. EXAMPLES

The invention may be better understood with reference to the accompanying examples, which are intended for purposes of illustration only and should not be construed as in any sense limiting the scope of the invention as defined in the claims appended hereto.

1. Example 1

Analysis of the Electrical Field Uniformity of Parallel Plate Electrodes in Standard Round Wells To analyze the effect of various electrode, and well designs, a series of two-dimensional numerical simulations of the electric fields were produced using the software analysis package Quickfield™ 4.1, (Student's Version, Tera Analysis, http://www.tera-analysis.com). This software package creates coarse-grained mesh type electrical field intensity maps by solving Poisson's equation with a finite-element analysis method in two dimensions. For the purposes of this analysis, the fringing effects due to the gap between the bottom of the electrode and the bottom of the well were ignored, and the voltage drops from the electrodes to the saline were also assumed to be negligible. The spatial resolution of the modeling is approximately 0.5 mm.

Figure 7A:
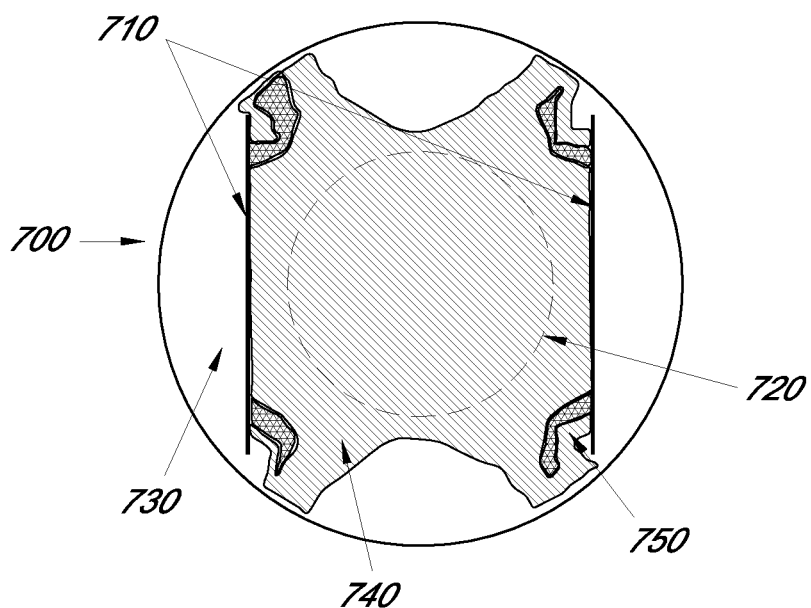
FIG. 7 Shows calculated electric field profiles for various electrode assemblies in round, 6.2 mm diameter wells. Dashed circle is a 3 mm diameter view window. In white areas, the electric field strength is less than 10% of the average electric field strength in the view window. In gray areas, the electric field strength is within 10% of the average electric field strength in the view window. In black areas, the electric field strength is greater than 10% of the average electric field strength in the view window.

FIG. 7A shows the results of the simulation using 4 mm wide parallel plate electrodes (710) with a 4 mm gap with a standard electrical potential difference of 2V located in a standard circular 96-well. In this figure, the outer circle (700) is the edge of the well, the two vertical lines (710) are the electrodes, and the dashed circle in the middle (720) is the area of observation. The gray area (740) is the area in which the electric field remains within ±10% of the mean field in the area of observation. In the white area (730), the field is less than 10% of the mean, and in the black area (750), the field is more than 10% greater than the mean field. Within the area of observation, the standard deviation of the field strength is 2% of the mean, and the difference between the maximum and minimum fields is 10% of the mean. Thus, this geometry satisfies the stated requirements for field uniformity for use in the present invention.

2. Example 2

Analysis of the Electrical Field Uniformity of Pin Electrodes in Standard Round Wells To determine the predicted field uniformity for two 1.0 mm diameter round pin electrodes placed in a standard 6.2 mm diameter well, separated by a distance of 4.0 nun, simulations were completed with the same conditions and assumptions as described in Example 1.

Figure 7B:
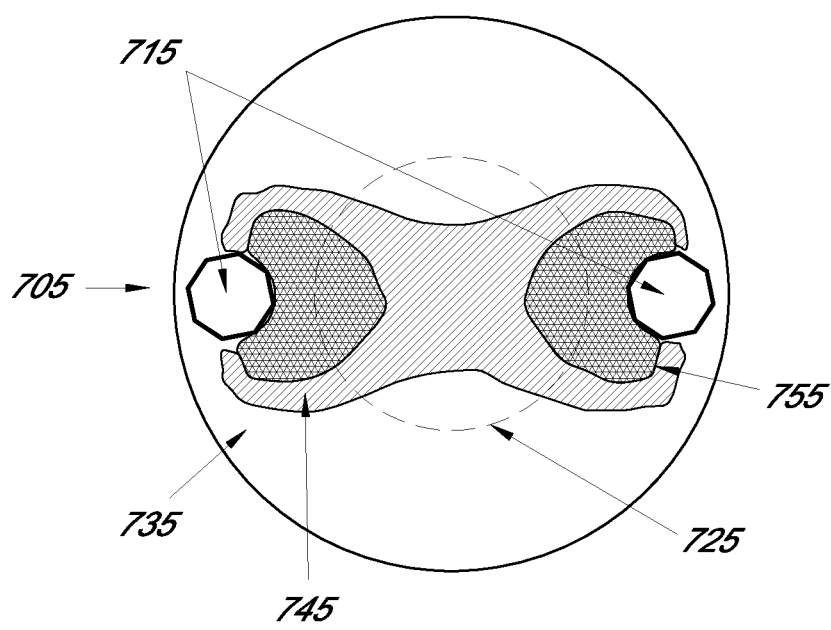

In FIG. 7B, the outer solid circle (705) is the edge of the well, the two smaller circles (715) are the electrodes, and the dashed circle in the middle is the area of observation. The gray area (745) is the area in which the electric field remains within ±10% of the mean field in the area of observation. In the white area (735), the field is less than 10% of the mean, and in the black area (755), the field is more than 10% greater than the mean field. Within the area of observation (725), the standard deviation of the field strength is 15% of the mean, and the difference between the maximum and minimum fields is 87% of the mean. Thus, this geometry does not create uniform electrical fields and as a consequence is not suitable for use with the present invention.

3. Example 3

Figure 8A:
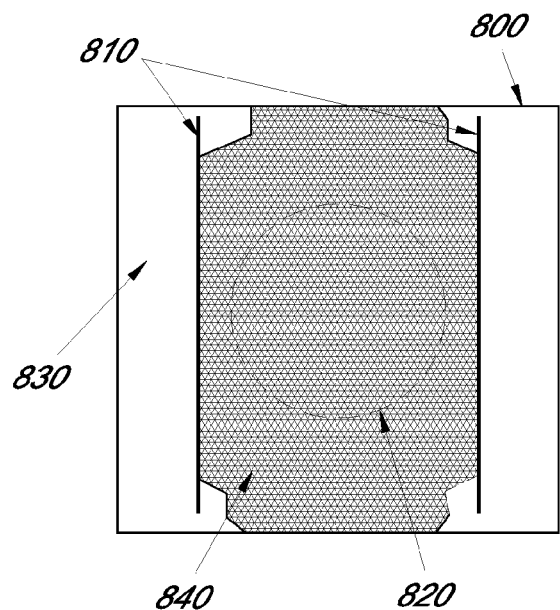
FIG. 8 Shows calculated electric field profiles for various electrode assemblies in round and square wells 6.2 mm across. Dashed circle is a 3 mm diameter view window. In white areas, the electric field strength is less than 1% of the average electric field strength in the view window. In gray areas, the electric field strength is within 1% of the average electric field strength in the view window. In black areas, the electric field strength is greater than 1% of the average electric field strength in the view window.

Analysis of the Electrical Field Uniformity of Parallel Plate Electrodes in Square Wells FIG. 8A shows a simulation of the field profile for two 6 mm wide parallel plate electrodes with a 4 mm gap in a 6.2 mm square well. In this figure, the outer square (800) is the edge of the well. The two vertical lines (810) are the electrodes. The dashed circle in the middle (820) is the area of observation. Of particular note is that the electric field scale for FIG. 8 has been greatly amplified compared to FIG. 7 to provide contrast for the variations in electrical field intensity. The gray area (840) is the area in which the electric field remains within ±1% of the mean field in the area of observation. In the white area (830), the field is less than 1% of the mean. In this simulation, at no point is the field more than 1% greater than the mean field. Within the area of observation, the standard deviation of the field strength is 0.02% of the mean, and the difference between the maximum and minimum fields is 0.12% of the mean. Thus, this geometry greatly improves the field uniformity.

The results of the simulation indicate that the primary source of field non-uniformity in the parallel plate system shown in FIG. 7A derives from the rounded walls of the well. In a standard well with a circular cross section, the current density will spread out and then contract as it passes from one electrode to the other, and this spreading generates non-uniformity. This can be corrected by using multiwell plates with square wells.

4. Example 4

Figure 8B:
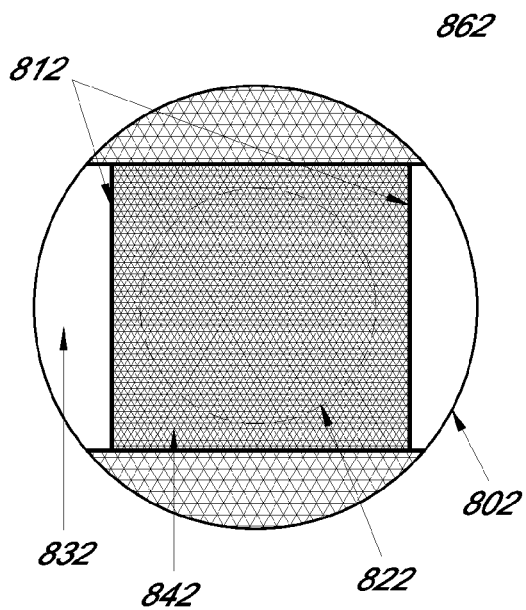
Figure 9:
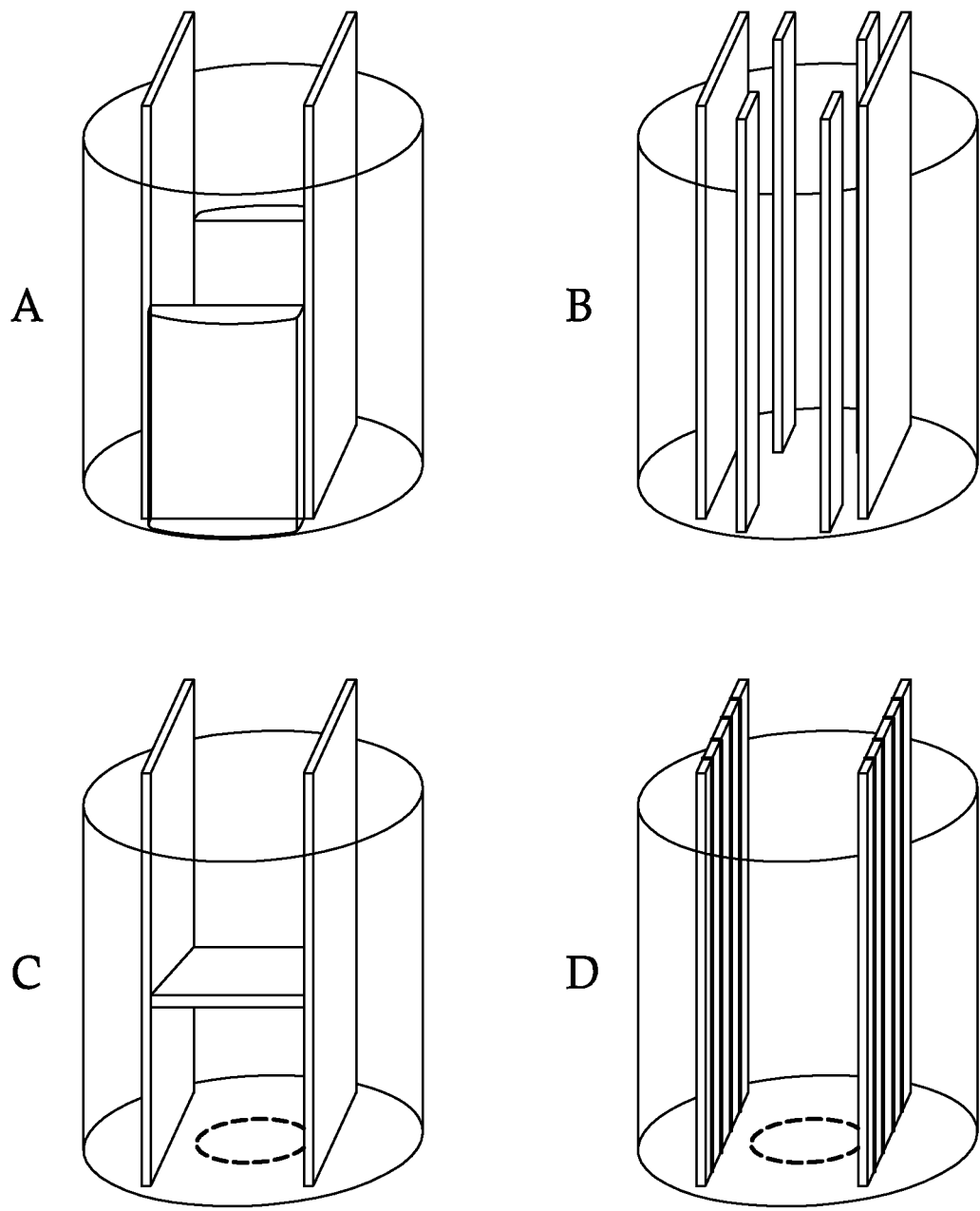
FIG. 9 Shows various electrode and insulator designs for improving electric field uniformity in round wells.

Analysis of the Effect of the Addition of Insulator Elements to Mask Off Rounded Areas of the Wells FIG. 8B shows a simulation of the field profile for two 4 mm wide parallel plate electrodes with a 4 mm gap in a 6.2 mm diameter round well using the standard conditions and analysis procedures as described in Example 1. Insulators are attached to the electrodes to mask off the rounded areas of the well between the electrodes, as shown in FIG. 9A. In FIG. 8B, the outer circle (802) is the edge of the well. The two vertical lines (812) are the electrodes. The dashed circle in the middle (822) is the area of observation. The cross-hatched areas (862) are insulators attached to the electrodes. The gray area (842) is the area in which the electric field remains within ±1% of the mean field in the area of observation. In the white area (832), the field is less than 1% of the mean. In this simulation, at no point is the field more than 1% greater than the mean field. Within the area of observation, the standard deviation of the field strength is 0.2% of the mean, and the difference between the maximum and minimum fields is 1.0% of the mean. Thus, this geometry greatly improves the field uniformity over the case where no insulator is used, but not as much as in the case of square wells.

The results demonstrate that the field uniformity in standard round well plates can be greatly increased by filling the area outside of the area defined by the electrodes with an insulating material. In practice inert plastics such as nylon, tetrafluoroethylene, polycarbonate, or any other non-porous polymer, or glass, could be used as the insulator material, provided that they are relatively stable to aqueous solutions, easily fabricated and preferably non-fluorescent. The insulator would typically be attached to the electrode, and would not obscure any of the area defined by the electrodes.

5. Example 5

Analysis of the Effect of Satellite Electrodes on Field Uniformity

Figure 8C:
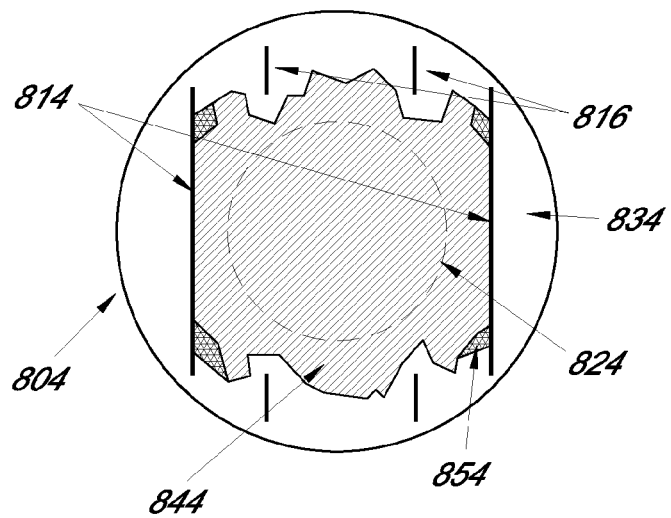

To test whether it is possible to compensate for the loss of current into the curved edge of the well via the use of satellite electrodes, simulations were carried out at a variety of electrode geometries. FIG. 9B shows one possible embodiment of this concept, and FIG. 8C shows the electric field profile when this geometry is analyzed using Quickfield™ as described in Example 1. In this example, two extra pairs of 0.7 mm wide parallel plate electrodes were placed with a 2 mm gap. These electrodes are outside of the area of observation, and are maintained at half the potentials of their parent electrodes.

In FIG. 8C, the outer solid circle (804) is the edge of the well. The two long solid vertical lines (814) are the parent electrodes, and the four shorter solid vertical lines (816) are the satellite electrodes. The dashed circle in the middle (824) is the area of observation. The gray area (844) is the area in which the electric field remains within ±1% of the mean field in the area of observation. In the white area (834), the field is less than 1% of the mean, and in the black area (854), the field is more than 1% greater than the mean field. Within the area of observation, the standard deviation of the field strength is 0.2% of the mean, and the difference between the maximum and minimum fields is 1.2% of the mean. Thus, this geometry greatly improves the field uniformity over the case where no insulator is used, but not as much as in the case of square wells. This example demonstrated the use of four satellite electrodes in a specific configuration. By adding more satellite electrodes outside of the area of observation, and by properly assigning their potentials as a function of the potentials applied to the parent electrodes, the electric field uniformity can, in principle, be improved to arbitrary precision.

For example in a round well configuration, field uniformity in the center area of observation can be improved by subdividing the parallel plate electrodes into several pieces separated by thin insulating dividers, as depicted in FIG. 9D. The potential applied to each electrode (expressed as a fraction of the potential applied to the central most piece) can be individually tuned to maximize the field uniformity in the area of observation.

This concept can be expanded to allow the use of non-parallel dipper electrodes, which have several vertical conducting stripes, each of which is independently controlled.

6. Example 6

Analysis of the Effect of the Meniscus on Electrical Field Uniformity

The meniscus created by dipper electrodes when inserted into a well generates variations of saline depth of around 10% across the area of observation. This in turn generates variations in the electric field of around 10% across the area of observation. These variations exist even if the electrode design is predicted to create perfect field uniformity. Thus, eliminating the meniscus effect will improve the actual field uniformity. One possible method to accomplish this is to add an insulating barrier between the electrodes. FIG. 9C depicts one such embodiment, wherein the insulating barrier is used to create a flat top surface for the liquid in the well. The bottom of this barrier, when the electrodes are inserted into the well, would be designed to sit approximately 2.5 mm above the bottom of the well. Thus, the barrier would be partially immersed in saline, and its bottom surface would define the top of the conductive chamber to be flat and perpendicular to the electrode surfaces. In this way, the electric field would not be perturbed by irregularities in the surfaces of the conductive volume.

7. Example 7

Fabrication of Dipper Electrode Electrical Stimulator

In one embodiment of the electrical stimulator the device is comprised of a self-locating frame that positions the dipper electrodes into the array of wells in a 96 well multiwell plate format (FIG. 1). FIG. 1 depicts the inserted position of the electrode array. In this example, the electrical stimulation device can be assembled from three functional parts. The first part is the positioning frame (40) that locates the device relative to the plate wells. This frame is made of metal and is a snug fit to the multiwell plate. This frame serves as the locating base for the second functional part of the system, the retractor mechanism.

The retractor system consists of shoulder bolts (70) and return springs (not visible). The springs are wrapped around the shoulder bolts, and press against the positioning frame (40) and the bottom of the insulating cover (90). The return springs hold the electrode assembly in the retracted position until the electrodes are lowered into the plate wells. The retractor mechanism locates the third functional part of the system, the electrode array.

The third functional part of the system is the electrode array. The electrode array is made up of eight pairs of identical electrode combs (10). The electrode combs are made of stainless steel and are precision laser cut to avoid distortion. Each comb has eight tabs of sufficient width to nearly span the diameter of the multiwell plate wells. The backbone of the comb forms the electrical connection to the tabs (50). Two of these combs form the electrode pairs that are inserted into a column of eight wells. The combs are held in position relative to each other by an insulating precision drilled plate (30) that locates the electrodes relative to the positioning frame. Insulating spacers (20) maintain electrode separation and index the combs to the drilled plate by means of a pinned interface. A second set of spacers (25) ensures precise positioning of the electrodes (10) relative to the plate (30). Alignment shafts (15) are inserted through alignment holes in the spacers (20) and the electrode combs (10) for additional stability. The combs and spacers are held in place against the drilled plate by an insulating cover (90).

The device may be used manually by placing the device on the multiwell plate and pressing down on the electrode assembly to lower the electrodes into the wells. When the electrodes are fully extended, a pair of locking bars (60) is inserted to keep the electrodes extended into the wells. Alternatively the electrode array can be automatically inserted and retracted in to the wells via standard mechanical or robotic control systems known in the art.

FIG. 3 shows a block diagram of the major electrical and optical components. Electrical stimuli were created via a high-power amplifier (320), driven by a pair of digital function generators (380 and 310). In one embodiment the switch (330) was a National Instruments (Austin Tex.) ER-16 controlled by a National Instruments PC-DIO 24 digital input/output card on board the VIPR™ reader controller computer (300). The switch (330) allowed defined wells within a 96-well plate to be electrically stimulated with any given time protocol. In this case, a single column of eight wells was stimulated simultaneously. The amplifier (320) was built using the APEX PA93 chip (Apex Microtechnology Corp, Tucson, Ariz.) following a circuit provided by the manufacturer. The amplifier had the following specifications: ±100V DC in, 100 GΩ input impedance, 20× voltage gain, ±90V out, ±3 A out, 10Ω output impedance. The function generators were Tektronix (Beaverton, Oreg.) model AFG310. The first function generator (380) was triggered by the VIPR™ reader software when the stimulus pulse train was required to begin, and produced a train of TTL pulses to trigger the second function generator (310). The second function generator was programmed with the stimulus waveform kernel.

8. Example 8

Voltage Dependence of Electrical Stimulation

Wild type Chinese hamster ovary cells (CHO cells) endogenously express a voltage-dependent sodium channel and can be conveniently used to validate and optimize electrical stimulation parameters. Besides this sodium channel, these cells appear to have gap-junctional connections between adjacent cells and a very small (~20 pA) voltage-dependent outward current.

The voltage dependent sodium channel in these cells (hereafter referred to as NaV1) has electrophysiological characteristics similar to rat brain type IIa sodium channels. Analysis of the current/voltage characteristics of this channel via standard electrophysiology reveals that typical wild type CHO cells have an average peak current of 100 pA per cell at −20 mV. This corresponds to a membrane resistivity ($R_{Na}$) of about 800 MΩ. Assuming a single-channel conductance of 10 pS, this suggests that there are only ~125 sodium channels per cell. In our hands, CHO cells typically exhibit a resting transmembrane potential ($R_m$) of about −35 mV, a resting membrane resistance >10 GΩ, and a cell membrane capacitance ($C_m$) of 15 pF.

To test the voltage dependency of electrical stimulation, wild type CHO cells were seeded into 96 well microtiter plates and incubated in growth medium for 24-48 hours. They were then rinsed with bath solution 1 and stained for 30 minutes each with 10 µM CC2-DMPE (coumarin), then 3 µM DiSBAC$_2$(3) (ethyl oxonol as described in Appendix A1). A stimulator assembly with 96 pairs of stainless steel electrodes (4 mm wide, 4 mm gap) was placed atop the assay plate, as described in Example 7. The electrodes were lowered into the saline covering the cells and remained 0.5 mm from the bottom of the well. Ratiometric fluorescence measurements were made during electrical stimulation using a VIPR™ reader as described above, and the data were analyzed according to the procedures in Appendix A2. At any one time, only one column of eight wells was assayed; the remaining wells received no excitation light or electrical stimulation. After each plate was assayed, the electrodes were thoroughly rinsed with distilled water and dried with compressed air, to prevent cross-contamination between plates.

Figure 10:
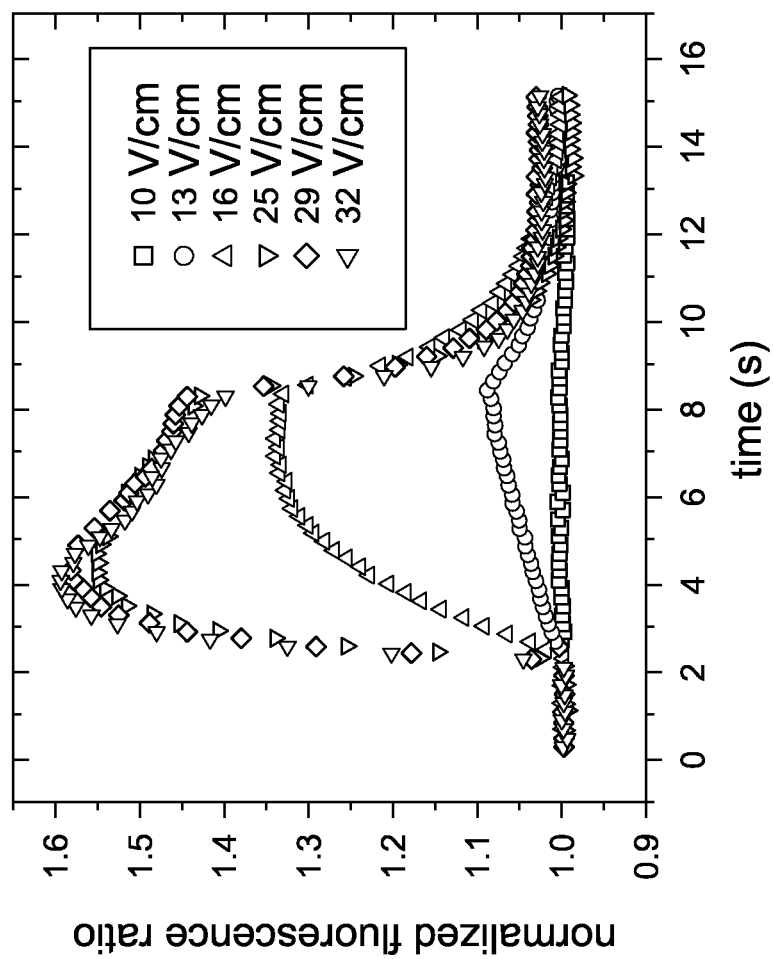
FIG. 10 Shows the effect of electrical stimulation protocols at varying pulse amplitudes over the time course of electrical stimulation in wild-type CHO cells.
Figure 11:
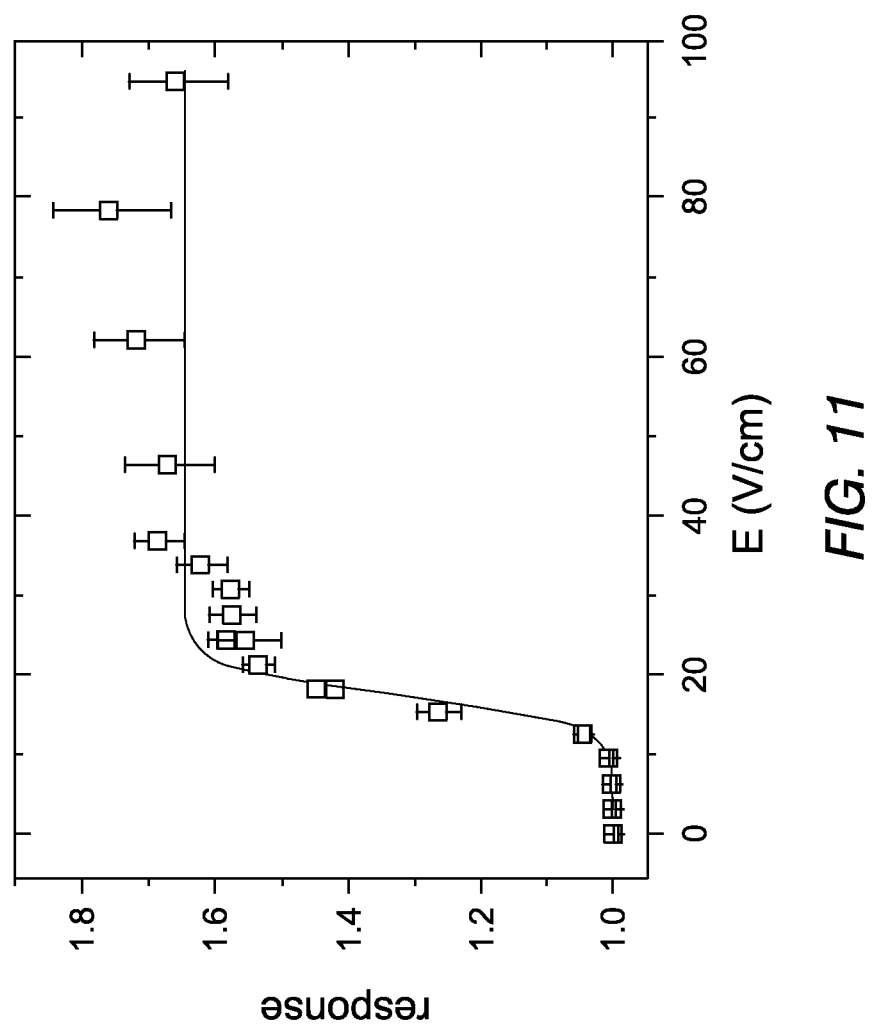
FIG. 11 Shows the relationship between the maximal cellular response and the applied pulse amplitude during electrical stimulation for wild-type CHO cells. Data was from FIG. 10 taken after about 5 seconds.

To determine the transmembrane potential changes occurring in the cells as a result of electrical stimulation, multiwell plates containing the cells were analyzed in a VIPR™ reader. The cells in a 3 mm diameter area of observation located midway between the electrodes were excited with light at 400±7.5 nm. The light was generated by a 300 W xenon arc lamp, and passed through a pair of a pair of dielectric interference band-pass filters to select the correct excitation wavelength. Light was directed to and from the cells via a trifurcated fiber optic cable, with one cable for excitation light and two for fluorescence emission. Simultaneous measurements of blue (460±20 nm) and orange (580±30 nm) signals were recorded from each well at 50 Hz, digitized and stored on a computer. Initial assays were 15 seconds long, and consisted of a 6 second stimulation of repetitive (90 Hz repetition rate) biphasic (5 ms/phase) square-wave stimulation beginning at 2 seconds at the electrical amplitudes shown. For two seconds before and seven seconds after the stimulation burst, no current passed through the electrodes. FIG. 10 shows the ratiometric responses at various field strengths up to 32 V/cm. In this case the apparent rise time of the recorded response is limited by the response time of the DiSBAC$_2$(3) that has a response time constant of around 1 second. Below pulse amplitudes of 10 V/cm, no response is detectable. Above 20 V/cm, the response is robust and increases only slightly as the voltage is further increased up to 32 V/cm. As shown in FIG. 11, at higher voltages, the peak response (measured after about 5 seconds) shows only further small increases in response. The data in FIG. 11 can be fitted to a Boltzman function, which had a midpoint at 18.0 V/cm with a 2.0 V/cm width. The sharpness of the onset and the flatness of the response at high fields are strongly suggestive of a threshold phenomenon. The electric field at which the response is half maximal (18 V/cm) corresponds to approximately ±30 mV deviations in transmembrane potential at the extreme edges of the cells, using formulas previously published (Equation 1, see also Tsong, 1991, Biophys. J. 60:297-306; and assuming an average diameter of the cells of 30 µm). It is therefore quantitatively consistent with the stimulation mechanism described above for voltage-gated sodium channels normally in the inactivated state.

Figure 12:
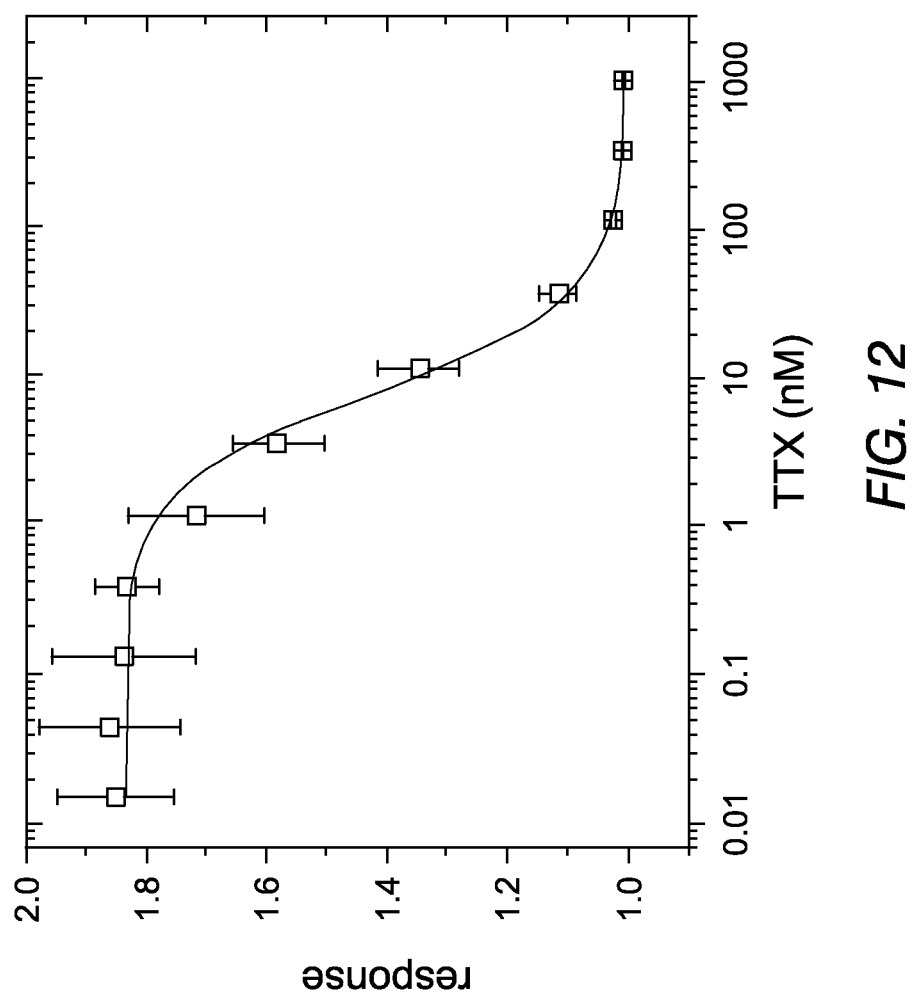
FIG. 12 Shows the dose response curve for the effect of TTX in wild-type CHO cells. Stimulation parameters were 33 V/cm, 50 Hz for 3 seconds with a biphasic square wave kernel (5 ms per phase). The solid line is a Hill function fit to the data with $EC_{50}=9$ nM and a Hill coefficient of 1.47.

High intensity electrical fields can result in electroporation of the cell membranes resulting in large relatively non-specific changes in transmembrane potential (Tsong, 1991, Biophys. J. 60:297-306). To establish whether or not this is also a major factor in the responses of the cells to lower electrical field intensities used here, experiments were conducted with the sodium channel specific toxin tetrodotoxin (TTX). If the effects of electrical stimulation can be blocked by the toxin, this would suggest that the effect of electrical stimulation is primarily mediated by the activation of sodium channels. The results of this experiment are shown in FIG. 12. The data was obtained with electrical field strength of 33 V/cm and demonstrate that TTX was able to completely block the effect of electrical stimulation with typical pharmacological characteristics consistent with the blockage of sodium channels. The EC$_{50}$ from the fit to this data is 9 nM, similar to the reported value for TTX in rat brain type IIa (8 nM, West et al., 1992, Neuron 8: 59-70). The fact that this signal is blocked by TTX with normal pharmacology is strong evidence that the signal generated via electrical stimulation is almost entirely due to NaV1.

9. Example 9

Variation of Cellular Response to Changes in Stimulus Pulse Width and Frequency

To examine the behavior of the cellular response as the stimulus pulse width and frequency were varied, experiments were carried out using wild type CHO cells as described in Example 8 above at a constant field strength of 25 V/cm, while varying the pulse duration and frequency.

Figure 13:
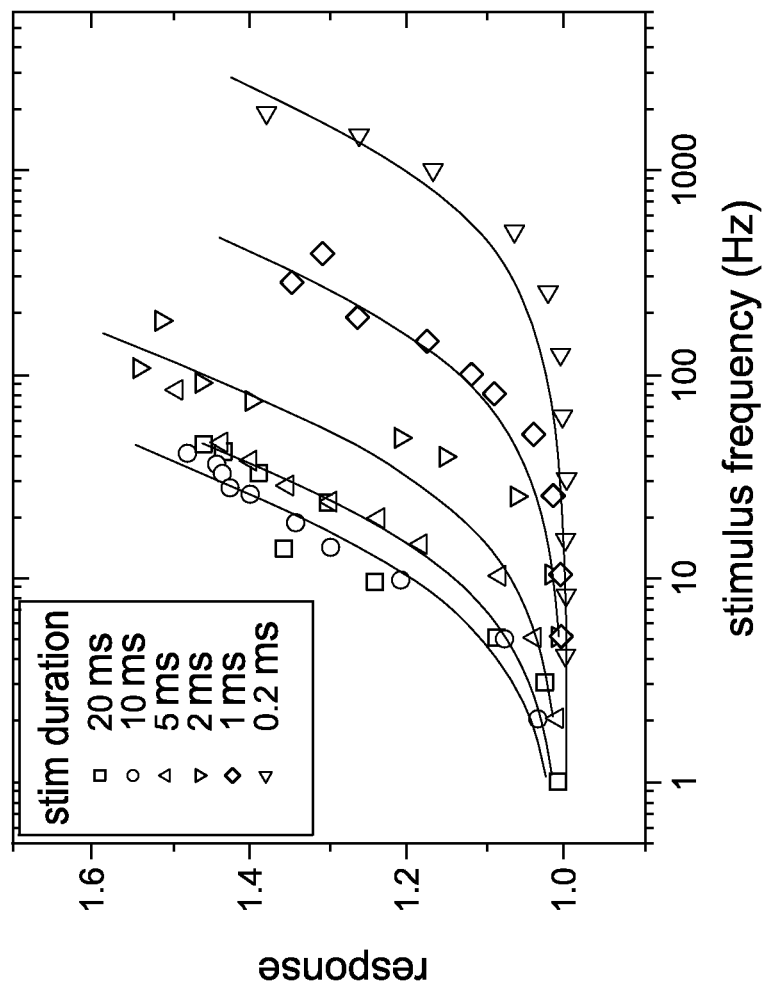
FIG. 13 Shows the relationship between pulse duration and frequency and the cellular response wild-type CHO cells during electrical stimulation. The electric field strength was always 25 V/cm. The stimulus was a three-second burst of biphasic pulses of varying duration and frequency. Solid lines are fits to the form $$R = 1 + \frac{Af}{f+f_0}.$$

The results are displayed in FIG. 13. Each data point represents the average of eight wells stimulated at the same time from experiments derived from five separate plates of wild-type CHO cells. The results show generally that as the frequency of stimulation increases the magnitude of the response increases. One would predict that this effect should eventually saturate as the transmembrane potential is driven to the sodium reversal potential ($V_{Na}$). In this case this does not occur because the sodium channel density is too low.

Increasing the pulse duration results in higher relative degrees of electrical stimulation at lower stimulation frequencies up to about 10 ms, beyond which further increases are less pronounced. Very small pulse durations (less than 1 ms) also limit the response, apparently because the channels are not effectively released from inactivation. To efficiently induce large cellular responses, the best stimulation parameters are typically in the range in which the pulse duration is greater than, or equal to the time constant for recovery for inactivation, and sufficiently short so that the frequency of stimulation is greater than the membrane time constant. Additionally the optimal frequency of stimulation is typically less than the reciprocal of the average channel open time.

These experiments demonstrate that electrical stimulation can be successfully used even in cells that express even relatively low levels of voltage dependent channels, and can be successfully completed under conditions that do not lead to significant electroporation or cell death. These experiments also demonstrate methods by which stimulus pulse duration and repetition frequency can be optimized to produce responses of a desired size.

10. Example 10

Analysis of CHO Cells Expressing an Exogenous Sodium Channel

Chinese hamster ovary cells were stably transfected with a plasmid encoding a voltage dependent sodium channel (hereinafter referred to as NaV2) as described in section VI. Whole-cell patch clamp analysis was used to confirm the electrophysiological and pharmacological properties of this channel prior to analysis via electrical stimulation. The peak transient sodium current at −20 mV was measured to be 600±300 pA (N=5), with an average cell membrane capacitance of 15±5 pF. The resting cell membrane resistance was too large to measure accurately ($R_L$>10 GΩ). The resting transmembrane potential was −31±3 mV.

To determine the threshold electric field for stimulation, cells stably expressing the sodium channel were plated in 96-well plates and stained according to the protocol in Appendix A1. The electrical stimulation protocol involved a 20 Hz, 3 second burst of biphasic (5 ms/phase) stimuli with variable field strength using the electrical stimulator described in Example 7.

Figure 14:
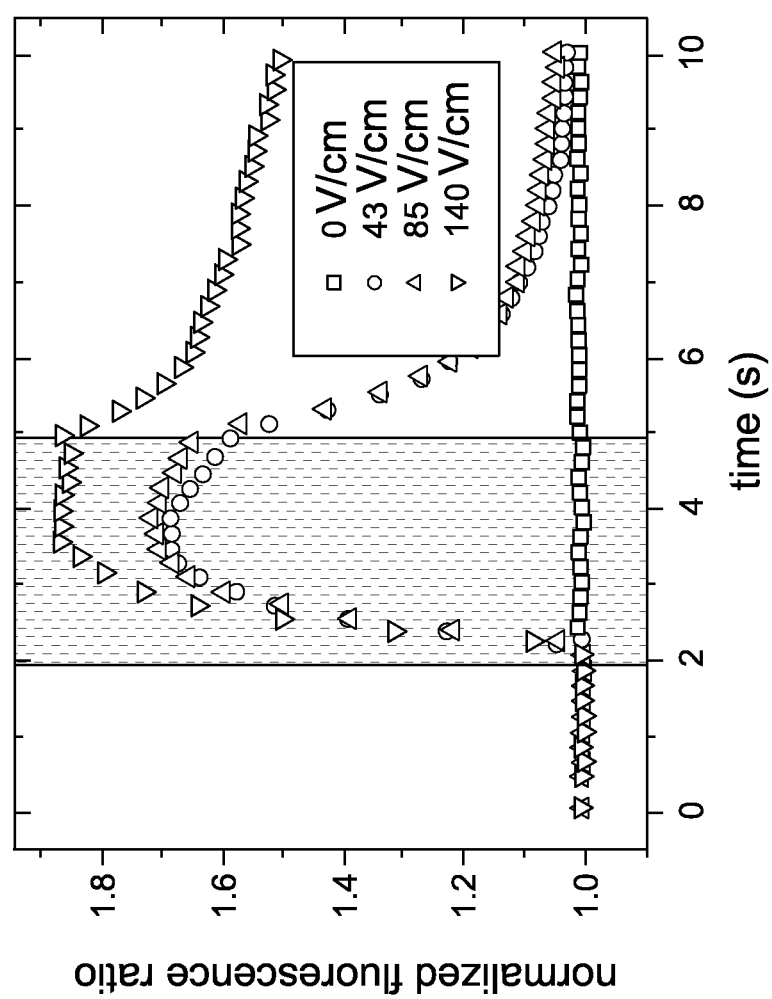
FIG. 14 Shows time traces for CHO cells expressing the NaV2 sodium channel cells electrically stimulated at various field strengths. Cells were stimulated in a 96-well plate, with a 20 Hz, 3 second-long train of biphasic, 5 ms/phase voltage pulses. The stimulation occurred during the shaded portion of the graph. In this experiment, the cells were stained with 20 μM CC2-DMPE and 63 nM $DiSBAC_6(3)$. This dye combination has a 2 ms time constant and accurately tracks the transmembrane potential. The rise and fall times of the response were fitted to exponential decay functions and were found to be $\tau_{rise}=200$ ms and $\tau_{fall}=850$ ms.

FIG. 14 shows representative time traces at various field strengths (each curve is the average of eight wells). At low field strengths, there is no detectable cellular response, suggesting that the average transmembrane potential changes less than about 1 mV. Between 35 and 90 V/cm, the response is stereotyped, with a fixed shape and amplitude. Above 90 V/cm, the peak response stays relatively constant, but the response decay time after the stimulus is removed becomes considerably extended.

Consistent with the experiments shown in Example 8, the response induced by electrical field strengths up to 85 V/cm could be inhibited by TTX whereas the response obtained from cells stimulated above 90 V/cm could not (data not shown). Therefore we conclude that the fast response is due to the sodium-channel-opening mechanism outlined above, while the slow response is mainly caused by electropermeablization of the membrane by the electrical field.

Figure 15:
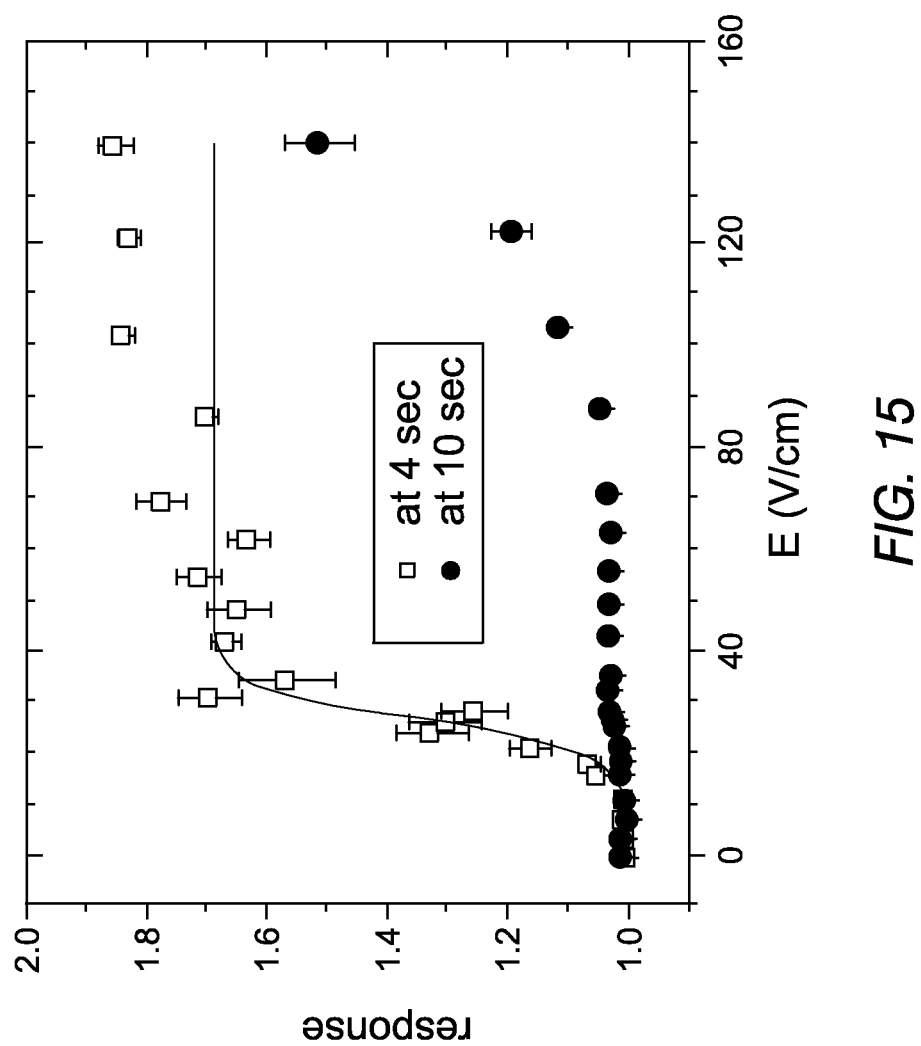
FIG. 15 Shows the relationship between the electric field strength and the cellular response measured after 4 seconds (squares) and 10 seconds (circles) of electrical stimulation. The line is a Boltzman fit to the data.

This effect is more easily seen by comparing the behavior of the fast response (4 seconds after stimulation) and the slow response (ten seconds after stimulation) with increasing field strength. This data is shown in FIG. 15. Fitting the fast response to a Boltzman function, the midpoint of the early response was at $E_{50}$=26 V/cm, with a width of ΔE=3.5 V/cm. The response was independent of field strength between 40 and 80 V/cm, with a slight increase when electropermeablization sets in above 90 V/cm.

The slower response due to permeablization was first detectable at 90 V/cm, and is itself of potential use in some applications. For example, permeablization can be used for resetting the transmembrane potential to zero, or if the permeablization is selective for a specific ion, for resetting the transmembrane potential to the equilibrium value for that ion. This could be useful, for example, in an assay for a channel that sets the transmembrane potential. Examples include potassium and chloride leak channels, potassium inward rectifiers, and low-voltage activated voltage-gated potassium channels.

These results are consistent with published studies in which electropermeablization begins with a threshold transmembrane potential of around ±200 mV, independent of cell type (Teissie and Rols, 1993, Biophys. J. 65:409-413). Based on formulae reported in that article and widely accepted in the literature, CHO cells with an average diameter of 30 μm will experience ±200 mV transmembrane potential changes when exposed to a 90 V/cm extracellular electric field.

11. Example 11

Determination of the Effective Release from Inactivation Time and the Effective Open-Channel Sodium Conductance To make quantitative estimates of the effective release from inactivation time and open channel conductance, but without being bound to any specific mechanism of action, the following theory was developed for experimental verification.

After opening, the sodium channels inactivate with a voltage-dependent time constant of order 1 millisecond. Because the current passed by the open sodium channels is strongly voltage- and time-dependent, it is not possible to easily generate an analytical expression for the voltage change after a single stimulation. However by making some simplifying approximations, we can model average idealized responses to create a testable theory. For the purposes here, we assume that upon opening, the sodium channels behave as a linear conductance above $V_t$=−40 mV with a reversal potential at $E_{Na}$=+60 mV. The conductance $g_{Na}$ is determined as the maximal current obtained at −20 mV in a whole-cell patch clamp experiment. The time dependence of the sodium channel conductance is simplified by assuming that, when the channel activates, it has a fixed conductance $g_{Na}$=1/$R_{Na}$ for a fixed time $\tau_{Na}$=1.0 ms, after which the channel inactivates.

Using a biphasic square wave stimulus kernel (each phase has a time $t_1$ and is repeated at a frequency f=1/T), the total current entering the cell during T is:

$$I = C_m \frac{dV}{dt} = \qquad (2)$$
$$= \frac{q_{Na} - q_L}{T}$$
$$= \frac{\tau_{Na}}{TR_{Na}}(V_{Na} - V)\left(1 - \exp\left[-\frac{t_1}{\tau_r}\right]\right) + \frac{1}{R_L}(V_L - V).$$

Here, $\tau_{Na}$ is the time the sodium channels are open. $R_{Na}$=1/$g_{Na}$ is the membrane resistance when the sodium channels are open. $R_L$ is the normal (leak) membrane resistance. $V_L$ is the leak reversal potential (i.e. the resting membrane potential). $V_{Na}$ is the sodium reversal potential. $\tau_r$ is the time constant for recovery from inactivation; this is actually a function of the hyperpolarizing voltage achieved during the pulse, but here we assume it to be a constant.

In reality, sodium channels from different parts of the cell experience different membrane potential changes, and the parameters $\tau_{Na}$, $\tau_r$, and $R_{Na}$ have strong dependence upon membrane potential. The full model would take into account the cell morphology, a random distribution of cell orientations, and the potential and time dependence of these parameters. It would then be possible to convolute these dependencies to produce effective values for these parameters. These procedures are too involved for the present discussion. We will instead recognize that the values that are extracted from fits to these equations represent complicated averages of the underlying channel properties.

Solving equation (2) for the transmembrane potential change during stimulation ($V - V_L$) yields:

$$(V - V_L) = (V_{Na} - V_L) \frac{f}{f_0 + f}\left[1 - \exp\left(-\frac{t}{\tau_{rise}}\right)\right], \qquad (3)$$
where
$$f_0 = \frac{R_{Na}}{R_L \tau_{Na}\left(1 - \exp\left[-\frac{t_1}{\tau_r}\right]\right)}$$
and
$$\tau_{rise} = \left(\frac{1}{R_L C_m} + \frac{\tau_{Na} f}{R_{Na} C_m}\right)^{-1}$$

If the stimulation is carried out for a long enough time such that a new transmembrane potential is reached, the steady-state equation is:

$$(V - V_L) = (V_{Na} - V_L)\frac{f}{f_0 + f}. \quad (4)$$

Figure 16:
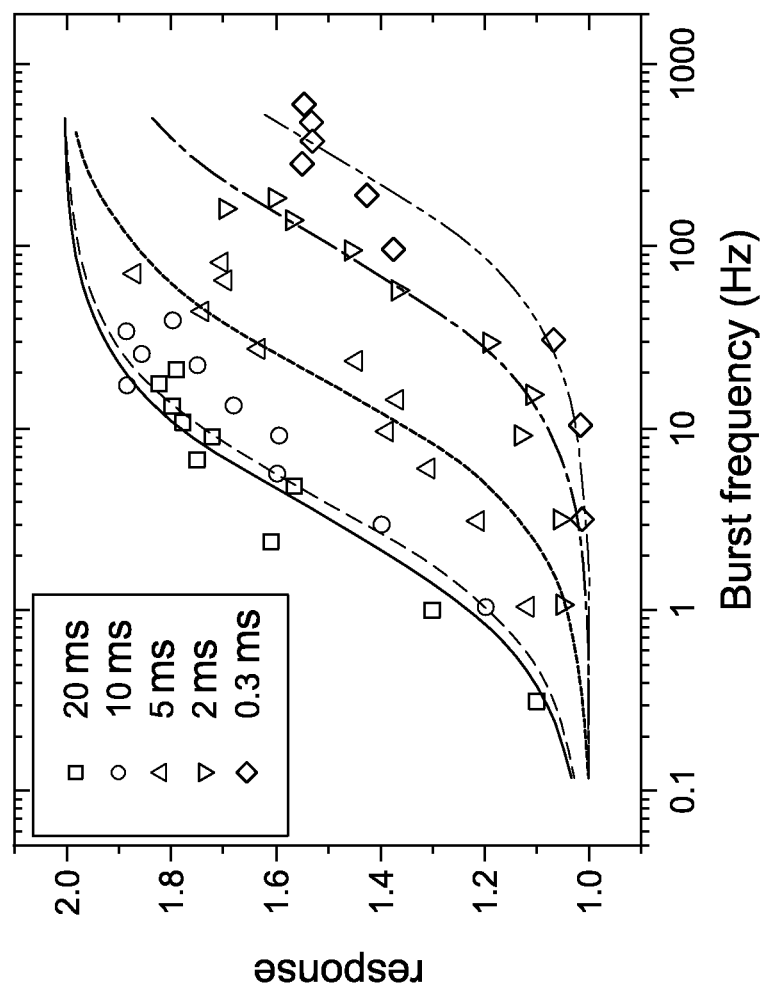
FIG. 16 Shows the effect of pulse duration and stimulation frequency on the cellular response of CHO cells expressing the NaV2 sodium channel.

To determine the effective release from inactivation time and open channel conductance, experiments were conducted as described in example 8, using a biphasic square wave kernel at a constant amplitude of 43 V/cm at varying frequencies and with pulse durations of 20 ms, 10 ms, 5 ms, 2 ms and 0.3 ms. The results, shown in FIG. 16, display the response as a function of stimulation frequency for several pulse durations. In this case as predicted, the response saturates at high frequencies as the transmembrane potential apparently approaches the sodium reversal potential. To determine the effective release from inactivation time and channel open time the response R was fitted to the modified Hill equation below.

$$R = 1 + \frac{Af}{F + f_0} \quad (5)$$

Equation (5) can be derived from equation (4) by recognizing that the ratiometric response R=1 for no transmembrane potential change, and is linear in the transmembrane potential change with an uncalibrated proportionality constant A.

In equation (5), A and $f_0$ are adjustable parameters. The fitting was performed using a non-linear least-squares analysis using Origin 6.0 software (Microcal, Northampton Mass.).

Figure 17:
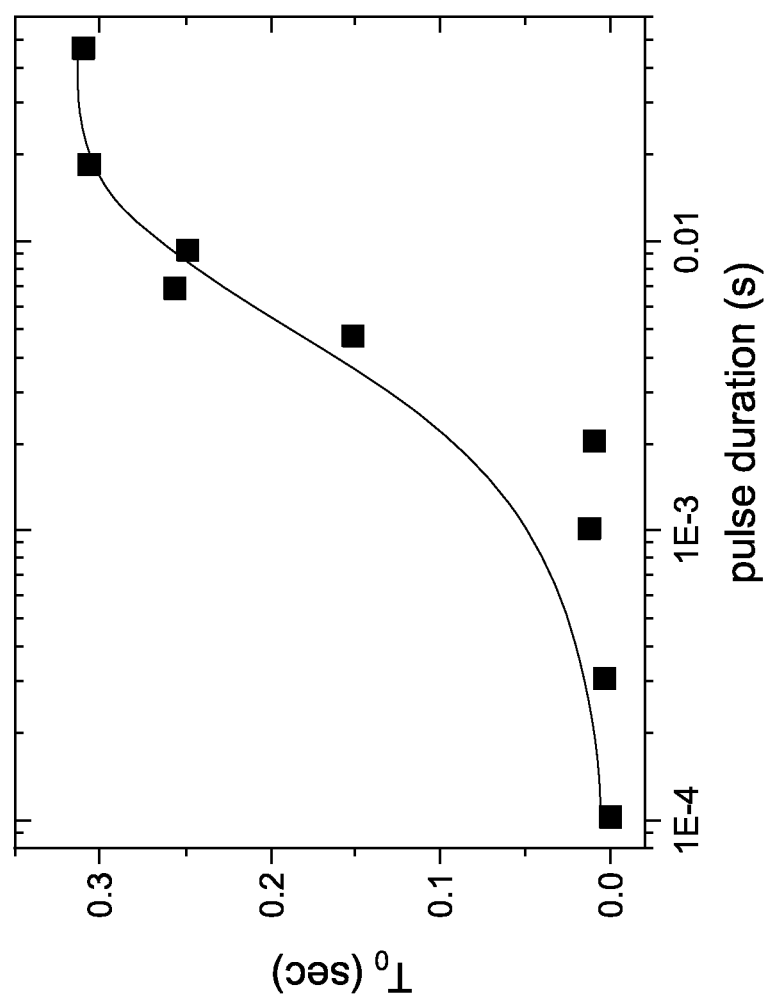
FIG. 17 Shows the knee time parameter $T_0$ from the fits to the data in FIG. 16 plotted versus the stimulus duration.

The parameters $T_0=1/f_0$ from equation (5) above were extracted from these fits and plotted against the pulse duration and are shown in FIG. 17. The line in this figure is a fit to an exponential decay, and from this fit, we extract the release from inactivation time constant ($\tau_r$) $\tau_r$=5.7 ms and $R_L\tau_{Na}/R_{Na}$=0.314.

Assuming that $\tau_{Na}$=1 ms and $R_L$=45 GΩ, then $R_{Na}$=140 MΩ. This in turn means that the peak sodium conductance would be 100 mV/140 MΩ=700 pA. This is in excellent agreement with the value measured in whole-cell patch clamp.

12. Example 12

Analysis of an Exogenous Sodium Channel in a Cell Line with Other Endogenous Ion Channels Wild-type HEK-293 cells typically express a variety of endogenous potassium and chloride currents (Zhu et al., 1998, J. Neurosci. Meth. 81:73-83), so that the resting membrane resistance for these cells is 5-10 GΩ. As a consequence the membrane time constant for these cells is corresponding smaller, thus for optimal stimulation of the cells, one would predict that the electrical stimulation protocol should be repeated at relatively higher frequencies compared to cells without endogenous potassium channels in order to generate comparable signals.

To test that a voltage regulated sodium channel could be efficiently electrically stimulated using the present invention in this cellular background, HEK-293 cells were stably transfected with a voltage dependent sodium channel hereinafter referred to as NaV3. Cells were transfected and selected as described in section VI and labeled with FRET dyes as described in Example 8. Cells were plated and loaded with 15 μM CC2-DMPE and 2 μM DiSBAC$_6$(3) and then subjected to a 25 V/cm, biphasic stimulus train repeated at a frequency of 90 Hz and with a 5 ms/phase pulse duration. The stimulation pulse train occurred for a total duration of 3 seconds and the digitization rate for data collection was 50 Hz.

Figure 18:
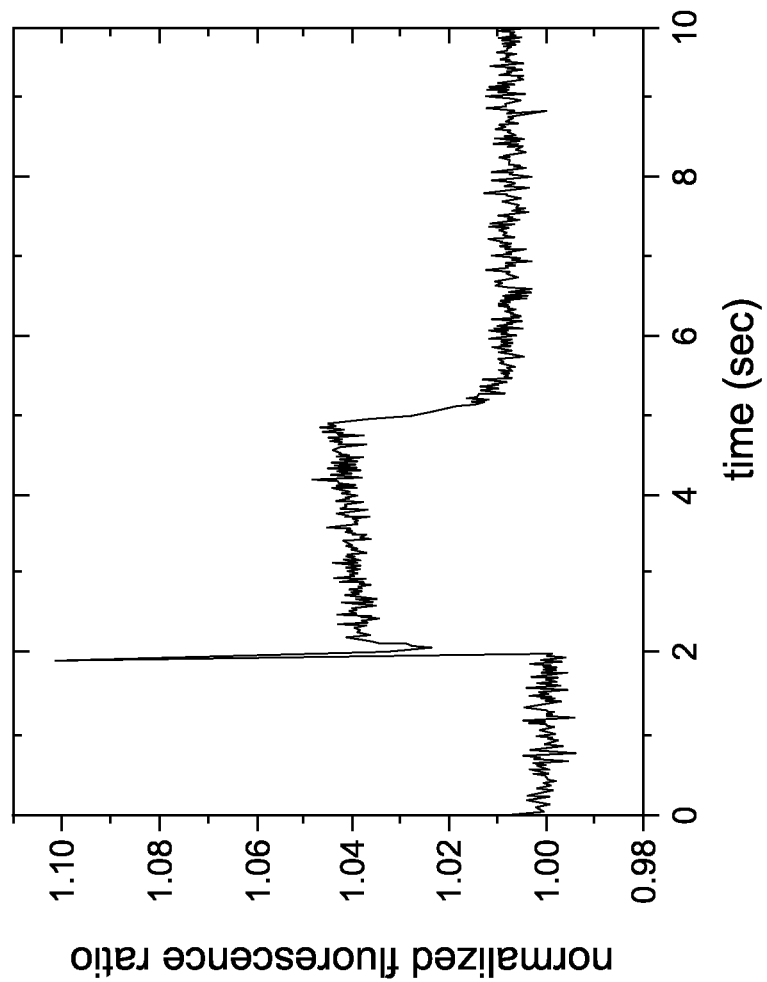
FIG. 18 Shows the temporal response of HEK-293 cells expressing the NaV3 sodium channel during electrical stimulation.

The response as a function of time (FIG. 18) shows a rapid (<20 ms rise time) initial phase which decays with a time constant of about 40 ms to a stable plateau. A small rebound potential change is also present between the spike and the plateau. We interpret this behavior as due to the activation of endogenous voltage-dependent potassium channels ($K_V$) that occur after the first stimulus pulse. Activation of these endogenous potassium channels would be expected to cause a reduction of transmembrane potential as potassium leaves the cell consistent with the experimental data. As electrical stimulation continues the transmembrane potential reaches a new equilibrium which is set by the balance of sodium influx into the cell and potassium efflux out of the cell. At the end of stimulation, the decay time constant of the response is about 143 ms, corresponding to a leak resistance of about 9 GΩ.

Figure 19A:
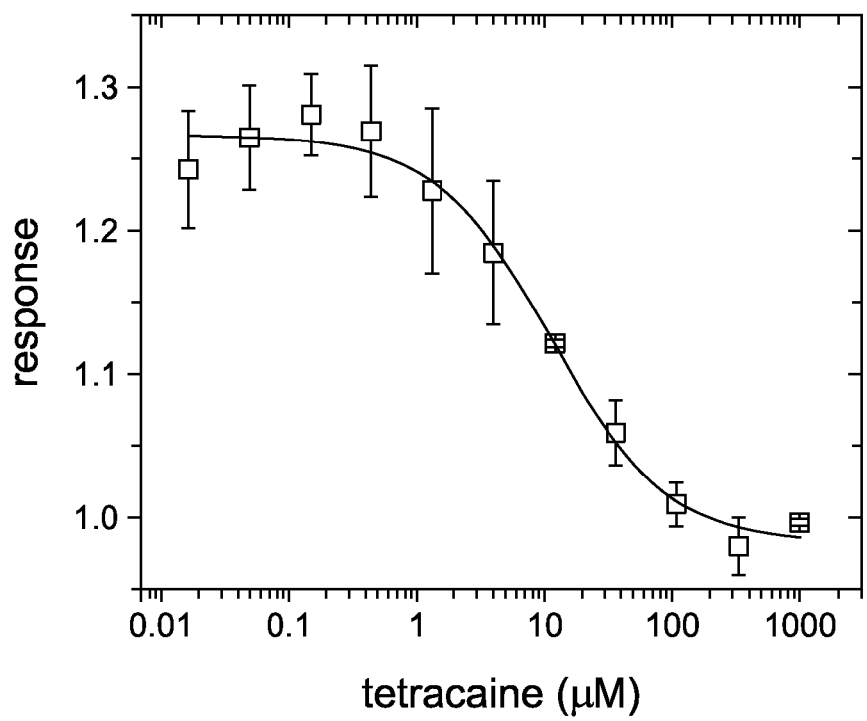
FIG. 19 Shows dose response curves for tetracaine (FIG. 19A) and tetrodotoxin (FIG. 19B) for HEK-293 expressing the NaV3 sodium channel. Electrical stimulation conditions were: E=33 V/cm, 10 ms/phase biphasic stimulation, 15 Hz burst for 1.5 seconds.
Figure 19B:
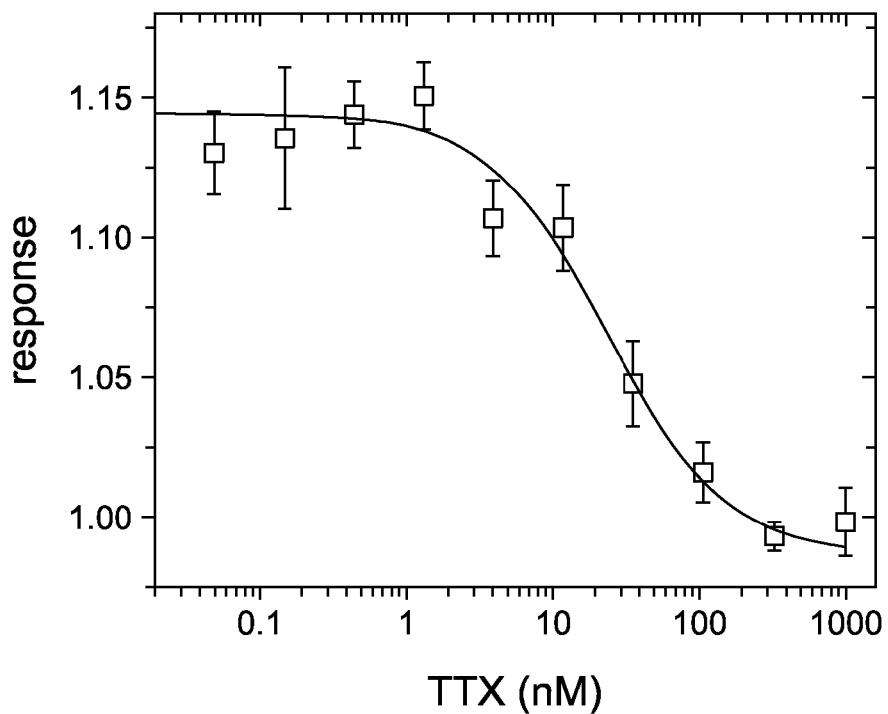

To determine whether this overall smaller response could be reliably used for drug discovery were conducted to determine whether the effects of TTX or tetracaine could be accurately characterized. The results shown in FIG. 19 demonstrate that the pharmacological inhibition profiles of these drugs using the present invention are consistent with the known behavior of the NAV3 sodium channel with these agents. The dose-response curve for TTX could be fitted with a Hill function with an $EC_{50}$=25 nM and Hill coefficient 1.1. The dose-response curve for tetracaine could be fitted to a curve with an $EC_{50}$=11 μM and Hill coefficient 0.97. These results suggest that the response is caused by sodium channel activity and that pharmacological information on known and unknown compounds can be obtained using this method.

13. Example 13

Analysis of HEK-293 Cells Expressing the NaV4 Sodium Channel

Figure 20:
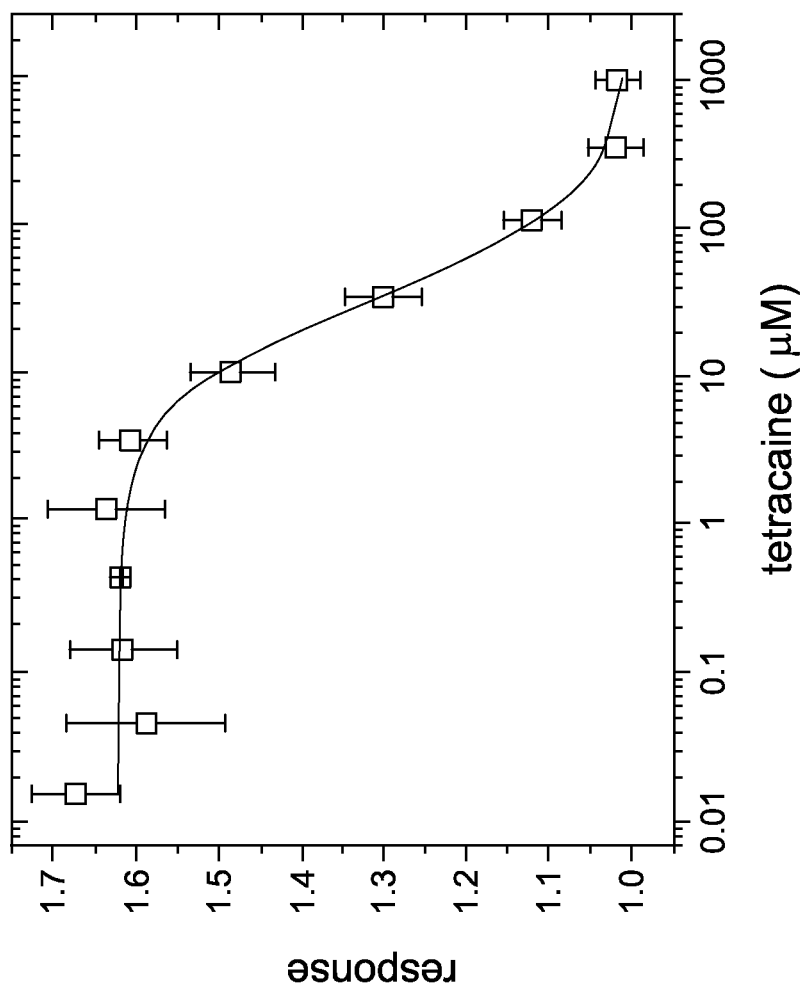
FIG. 20 Shows a dose response curve for tetracaine for HEK-293 expressing the NaV4 ion channel. For this experiment, electrical stimulation parameters were E=33 V/cm, 10 ms/phase biphasic stimulation, 15 Hz burst for 1.5 seconds.

To determine whether the present method is generally applicable to a wide range of different sodium channels, HEK-293 cells were stably transfected with another voltage dependent sodium channel, hereinafter referred to as NaV4. These cells were transfected, selected and loaded with FRET dyes as described in section VI and Example 8. The results of a dose-response curve for tetracaine on this channel are shown in FIG. 20. Here the data points are averages and standard deviations of eight wells and the solid line is a fit to a Hill function with an estimated $EC_{50}$=35 μM and Hill coefficient 1.35. These results are consistent with the known pharmacology of this ion channel and demonstrate again that the cellular response is caused primarily by sodium channel activity.

14. Example 14

Analysis of HEK-293 Cells Expressing a Mixture of Voltage-Activated Chloride and Potassium Channels A demonstration of the direct stimulation of voltage-dependent chloride and potassium channels was performed using wild-type HEK-293 cells, which endogenously express a mixture of several voltage-activated chloride and potassium channels (Zhu, Zhang et al. 1998). Wild-type cells were grown in 96-well microtiter plates and assayed at confluence after staining with the FRET dyes according to the protocol in Appendix A1. Initial stimulus parameters included a 3 second long electrical stimulation at 20 Hz with a biphasic square wave stimulus kernel with a pulse duration of about 5 ms/phase. Stimuli were performed at varying electric field intensities to determine the threshold field strength for a measurable cellular response, and in the presence or absence of potassium channel blockers.

Figure 21:
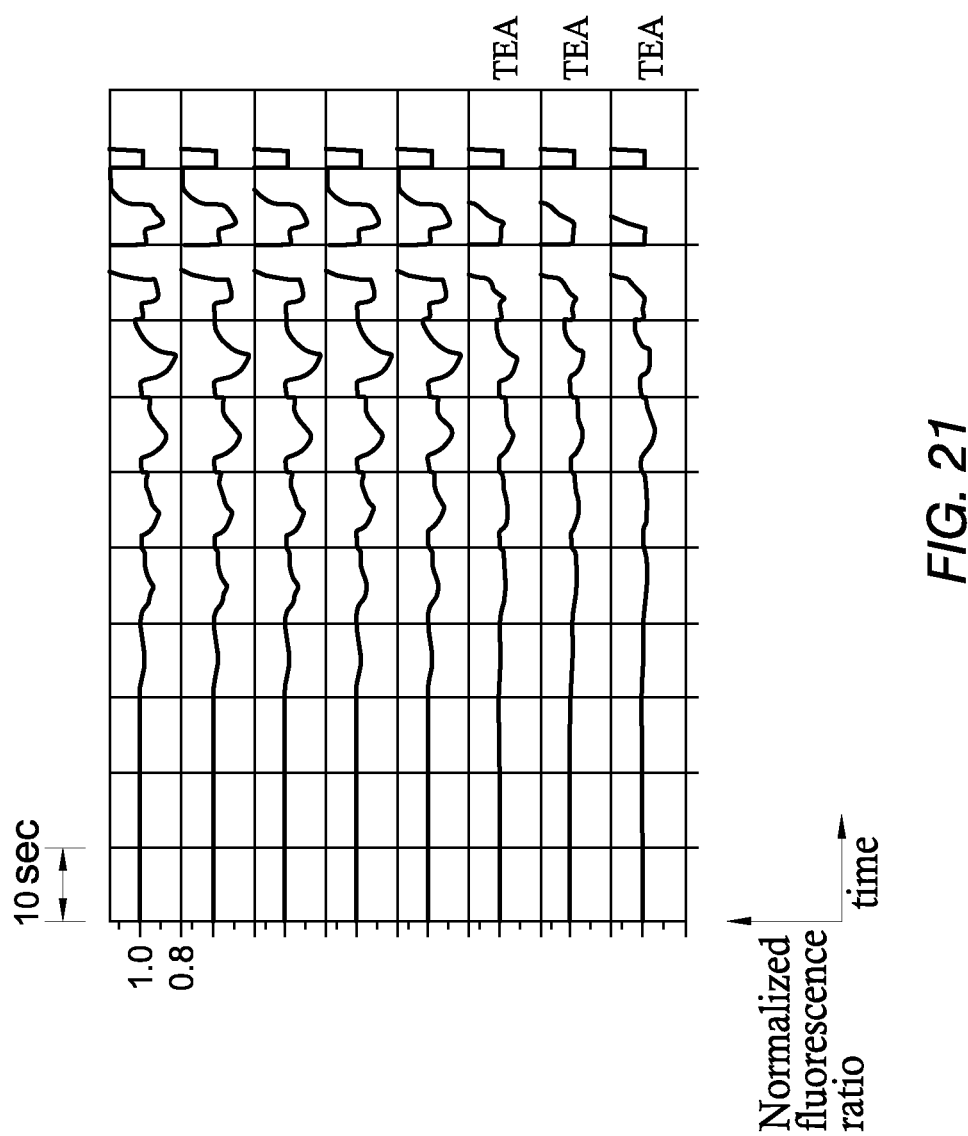
FIG. 21. Shows a full-plate view of electrical stimulation of wild-type HEK-293 cells. Each individual panel represents the time trace of the normalized fluorescence ratio of a single well in the 96-well plate. Each well in a vertical column was stimulated simultaneously with the same field strength. Field strength increases from left to right. Rows 6-8 contained 10 mM TEA to block the voltage-dependent potassium channels.

FIG. 21 shows the cellular voltage response obtained during this experiment. In this figure, each panel contains the ten-second time trace of the response for a single well. The panels are laid out to match their relative positions on the plate. The vertical axis in each panel is the background subtracted, normalized fluorescence ratio of the FRET voltage sensitive dye combination CC2-DMPE/DiSBAC2(3), changes in this quantity are roughly proportional to changes in the membrane potential. Each column had identical stimulation conditions, with increasing electric field strength from left to right across the plate. The twelfth column of the 96 well plate (not shown) contained no cells and were used for background subtraction. Rows 6-8 contained 10 mM TEA to block the voltage dependent potassium channels. At the lowest field strengths tested, there was no detectable response. At intermediate electrical fields, a negative voltage response can be seen which rapidly decays when the stimulus is removed. At the highest fields a large positive response is elicited. This behavior sets in above 50 V/cm, similar to the electropermeablization threshold seen in CHO cells expressing NaV1, (Example 8).

Figure 22:
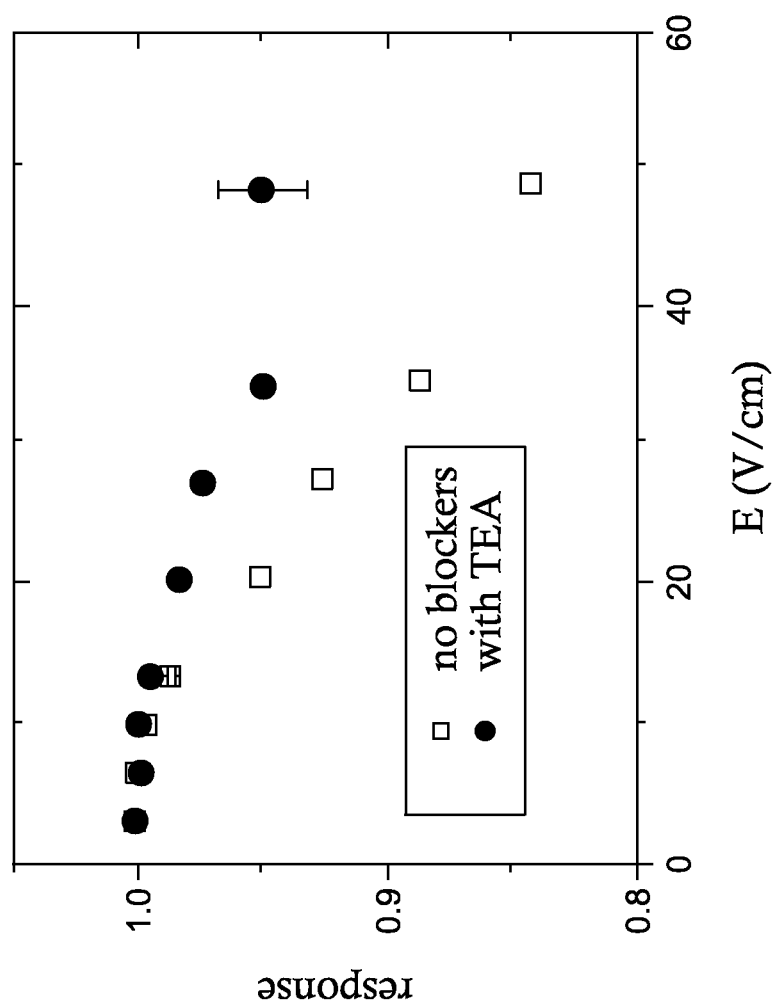
FIG. 22. Shows the cellular response as a function of the stimulus field for wild type HEK. Error bars are standard deviations. Open symbols: no added blockers. Filled symbols: 10 mM TEA added to block potassium channels.

FIG. 22 shows the response averaged between 4.5 and 5.0 seconds of stimulation as a function of the electric field intensity. The large positive responses above 60 V/cm were excluded to show the channel-dependent negative responses. The coefficient of variation of the response is generally extremely small, yielding exceptionally large screening windows (see Appendix A3). For the unblocked data for 20-40 V/cm, the difference between stimulated and unstimulated wells is over 20 standard deviations.

Tetraethylammonium (TEA), a well-known potassium channel blocker (Hille, 1992, Ionic Channels of Excitable Membranes), was added to rows 6, 7, and 8 at a fully-blocking concentration of 10 mM. This treatment partially blocks the response. This result is consistent with the existence of both potassium (blocked by TEA) and chloride (unaffected by TEA) channels in these cells that respond to electrical stimulation. The effect of the potassium channels can be isolated by blocking the chloride channels with 4,4'-diisothiocyanostilbene-2,2'-disulfonic acid (DIDS) or 4-acetamido-4-isothiocyanostilbene-2,2'-disulfonic acid (SITS; see Hille, 1992, Ionic Channels of Excitable Membranes). Then, the same cell line could be used to screen two channel classes.

15. Example 15

Identification of State Dependent Blockers

Any proposed screening system should preferably be able to reproduce the pharmacology of known compounds as determined by accepted methods. To verify that this was the case for the present invention, a series of test compounds of defined activity were analyzed using a CHO cell line that expresses the NaV2 channel. To accomplish this, cells were cultured in 96 well plates and stained with voltage sensitive dyes as described in Appendix A1. Test compounds were added to the cells with the oxonol loading buffer. Unless otherwise noted, the compounds were tested as in replicates of 8, with 1/3 dilutions across eleven columns of the assay plate.

Figure 23A:
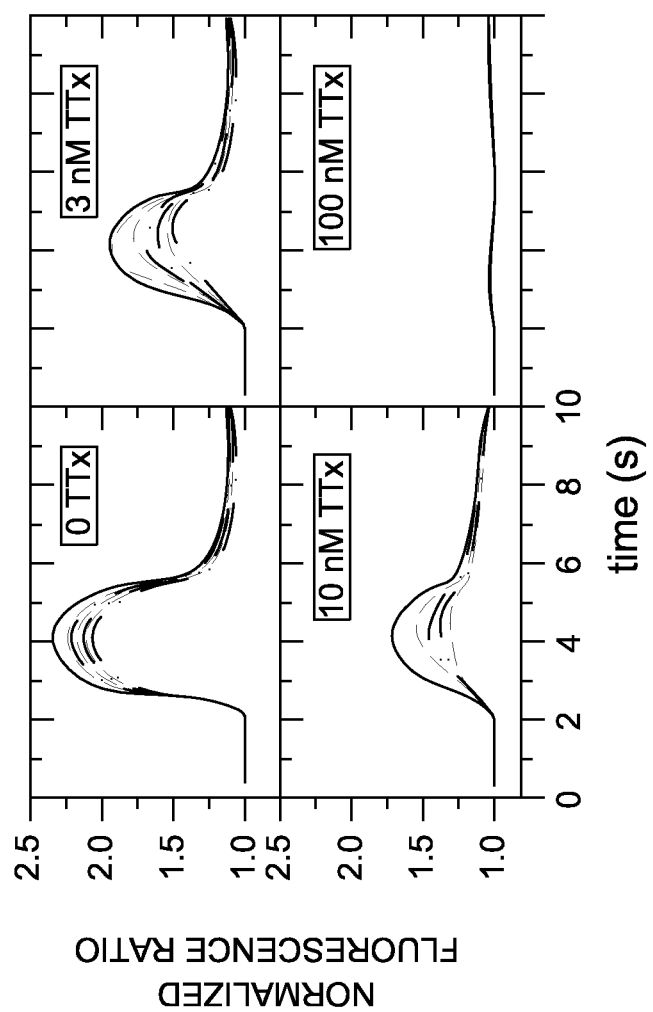
FIG. 23 Shows the time response traces for selected concentrations of the sodium channel blockers tetrodoxin (TTX) (FIG. 23A) and tetracaine (FIG. 23B) in CHO cells expressing the NaV2 sodium channel.
Figure 23B:
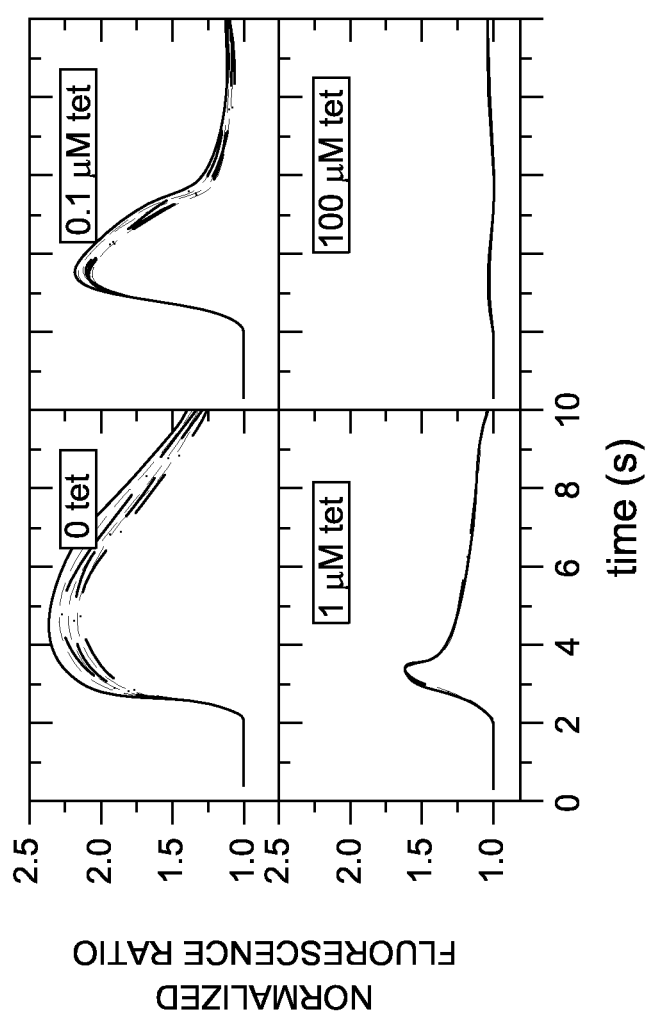

FIG. 23 shows the time traces for selected concentrations of the sodium channel blockers tetrodotoxin (TTX) and tetracaine.

Tetrodotoxin is a potent, reversible, non-state specific sodium channel antagonist. By comparison tetracaine is a use dependent sodium channel blocker that exhibits different affinities for different sodium channel states.

The results show that the present invention provides for highly reproducible results with relatively little variability either between samples or between plates. In FIG. 23 the effect of TTX can be seen as a progressive loss of response, without significant changes in the shape of the response. By comparison with tetracaine the responses not only decreases, but changes shape as the concentration varies. The C.V. for these experiments were 10% (TTX) and 9% (tetracaine), compared to typical CVs using the same voltage dyes, but traditional liquid addition were 16% (TTX) and 18% (tetracaine).

Figure 24:
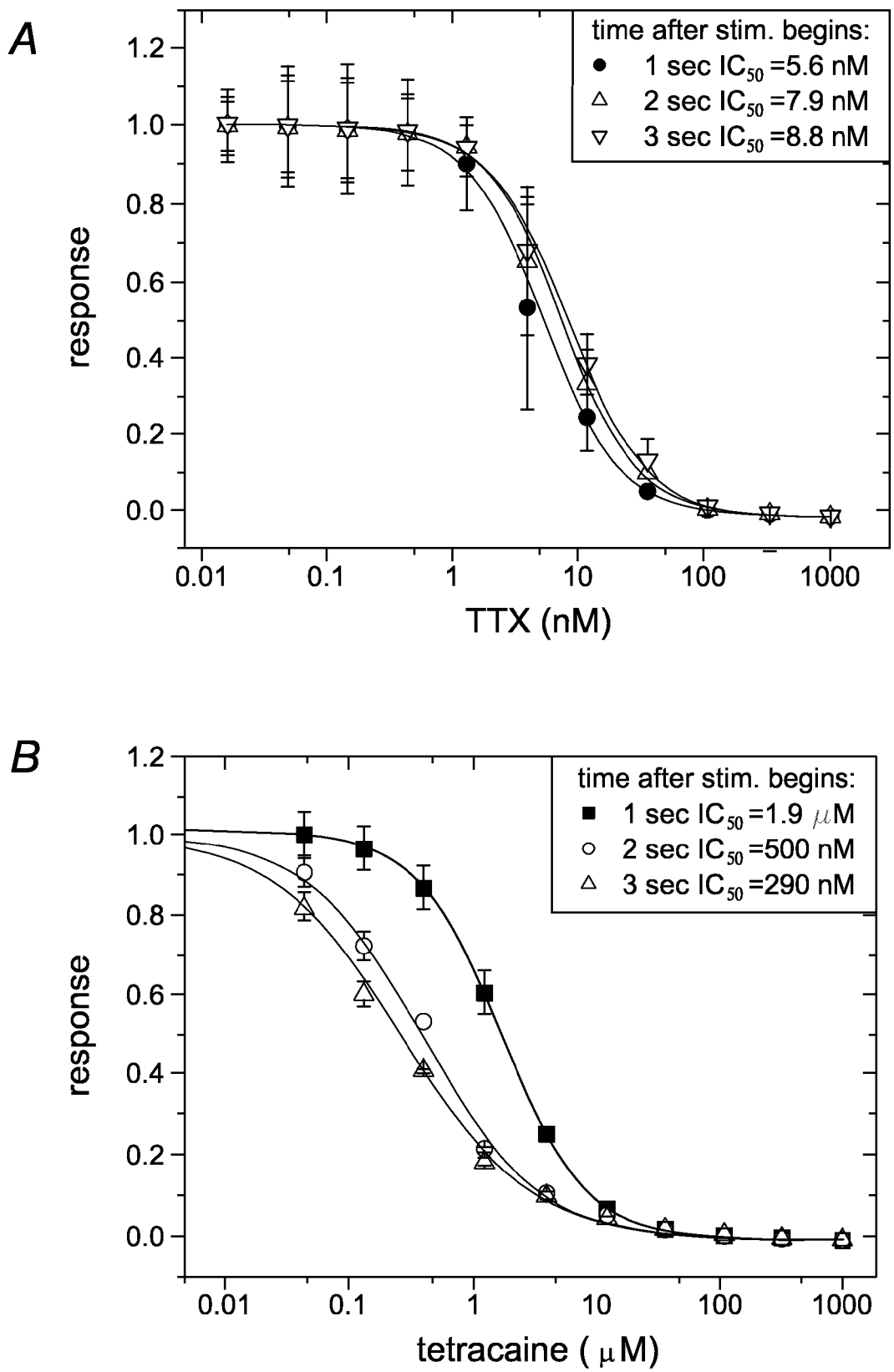
FIG. 24 Shows the dose response curves for TTX and tetracaine inhibition of the NaV2 sodium channel.

Importantly the results also show that the present invention can identify the state dependent blockage of the sodium channel by tetracaine. The use-dependent block of tetracaine is more apparent in the dose-response curves shown in FIG. 24. For TTX, the channel block is independent of the time window used for calculating the response. For tetracaine, however, the blockade is an order of magnitude stronger at 3 seconds than at 1 second. Under the same stimulation conditions, other use-dependent blockers (lidocaine and bupivicaine) showed a smaller amount of shift in the dose-response curves. The $EC_{50}$ values obtained by the electrical stimulation protocol for lidocaine were similar to the high-frequency values reported in the literature (see Table 4); this suggests that lidocaine and bupivacaine have fast enough use-dependence to be fully saturated at the 20 Hz stimulus used here. This in turn suggests that we can explore the use-dependent properties of local anesthetics by varying the stimulation frequency.

Table 4 lists the blocking concentrations for several sodium channel antagonists. The literature values reported have all been measured using whole-cell patch clamping, and are thus based on direct measurements of the sodium channel current.

TABLE 4

| i. Pharmacology of NaV2 in the electrical stimulation assay | | | |
|---|---|---|---|
| b. Compound | Electric field stimulation | Literature value | Reference |
| Tetracaine | 0.19 | | |
| Bupivacaine | 1.0 | | |
| Lidocaine | 30 | 11 | a |
| | | 97 | d |
| Phenytoin | 24 | 19 | a |
| | | 36 | d |
| WIN-17317 | 0.009 | 0.009 | b |
| | 0.006 | 0.008 | c |
| saxitoxin | | 0.001 | c |
| verapamil | | 3 | d |
| capsaicin | 1.6 | | |
| amiloride | >1000 | | |

References
a Ragsdale et al., 1996, Proceedings of the National Academy of Sciences, U.S.A. 93: 9270-9275
b Wanner et al., 1999, Biochemistry 38: 11137-11146.
c West et al., 1992, Neuron 8: 59-70.
d Ragsdale et al., 1991, Molecular Pharmacology 40: 756-65.

In Table 4, the table entries are $EC_{50}$ values (in micromolar) for fits to the dose-response curves from each assay. Each experiment was done twice, with four wells per drug concentration per experiment. In each experiment, eleven concentrations were used, spanning five orders of magnitude in concentration. Reported values are the averages of the calculated $EC_{50}$ from each experiment. In the cases of use-dependent blockers, the lowest recorded values are quoted.

WIN-17317 and TTX are potent tonic blockers of a variety of sodium channels. These compounds can be detected using the electrical stimulation format, which yields blocking potencies near the literature values.

The first four drugs (lidocaine, bupivicaine, tetracaine, and phenytoin) are use-dependent blockers. That is, they have different affinities for the various states of the channel. They are of great therapeutic relevance, since at the proper concentration, they can block damaging repetitive bursting of neurons and muscle cells while leaving normal, low-frequency activity unaffected. In all cases, the measured blocking concentration measured with electric stimulation is close to the reported literature value. The electrical stimulation assay format is the only reliable high-throughput method for detecting all modulators of sodium channels, including agonists, antagonists, and use-dependent blockers.

15A. Example 15A

Further Identification of State Dependent Blockers

We further demonstrate the characterization of use-dependent effect of several known channel blockers against the endogenous $Na_V$ channels of Chinese Hamster Ovary cells (CHO) at a stimulation frequency of 1 Hz. Our data demonstrate that the combination of electrical field stimulation and fast voltage-sensitive dyes provides an effective approach to induce and measure use-dependent block. Moreover, the potencies and use-dependent properties of test compounds determined by this method are in accord with those reported for the same channel type using patch-clamp technique. This new technique permits rapid detection and characterization of novel use-dependent compounds.

Figure 32:
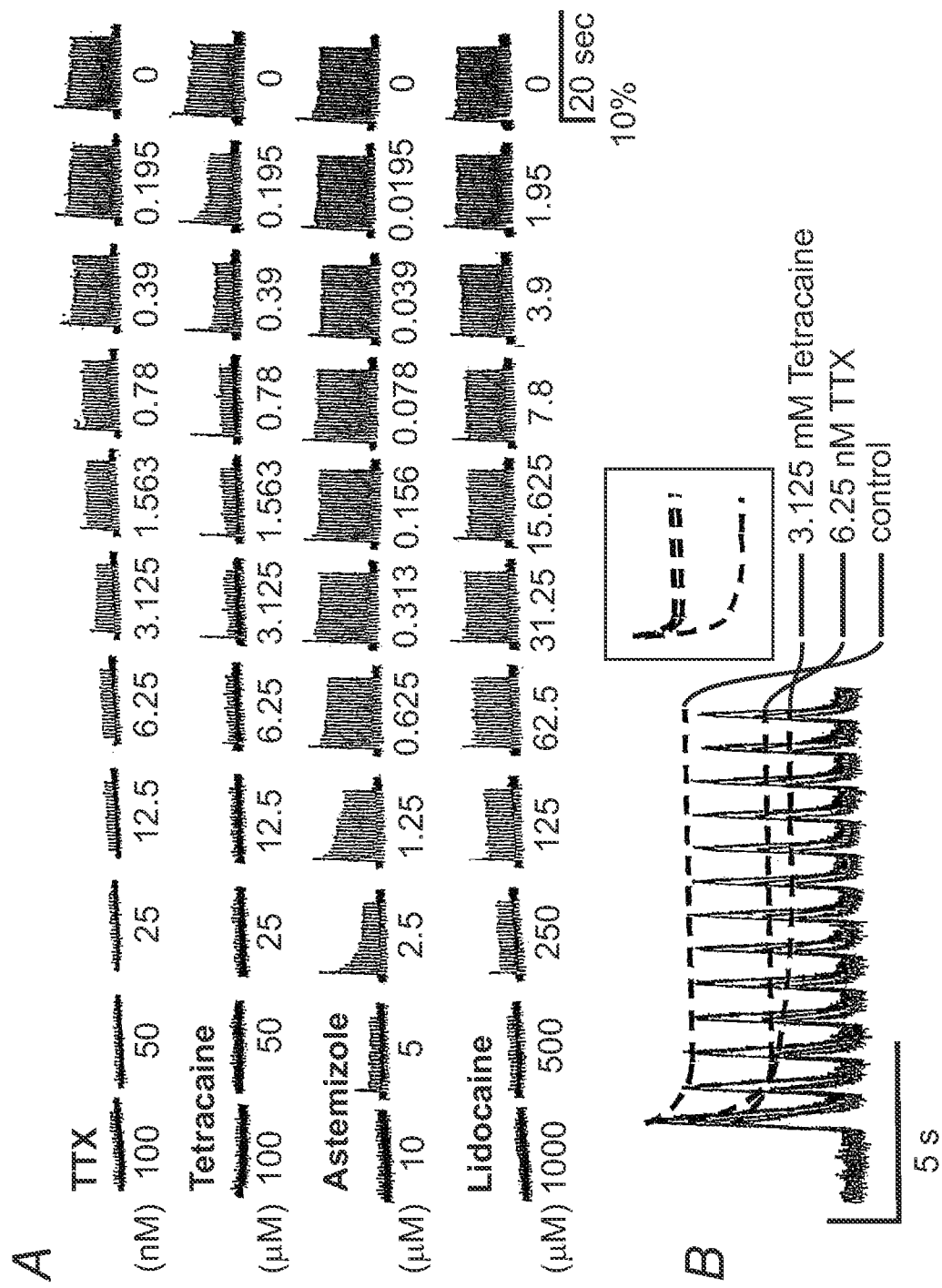
FIG. 32 Shows the use-dependent effects of different compounds at varying concentrations using repetitive electrical stimulation at 1 Hz for 20 seconds.

FIG. 32A shows data from four compounds used to illustrate the use-dependent effect on fluorescence ratio response. The representative traces of ratio response were elicited by repetitive electrical stimulation, delivered at 1 Hz for 20 seconds, in the presence of TTX, tetracaine, astemizole, and lidocaine, respectively. In these experiments, each 96-well cell plate was treated with two compounds, each of which had four replicates of titration from columns 1 to 10 to cover a broad range of concentrations, as indicated. Cells in column 11 were used for control. The peak ratio response in the absence of blockers typically exhibited a fast time-dependent decrease by 20-30% to a new steady-state level at the end of repetitive stimulation. The small impulse-like response seen at highest concentrations of compounds were presumably due to transient membrane capacitive current induced by electrical field. Use-dependent block of endogenous $Na_V$ channels by test compounds was characterized by decreased ratio of last peak response over first peak response at certain concentration range, as seen in the presence of tetracaine or astemizole. By contrast, only minor or no use-dependent block by lidocaine or TTX was observed, indicating that both blockers are relatively weak use-dependent against endogenous $Na_V$ channels at this frequency.

FIG. 32B superimposes traces of ratio response in the absence and presence of 3.125 µM tetracaine and 6.25 nM TTX to demonstrate the difference in development of block between two blocker types. As shown in the inset, tetracaine induced more additional block than TTX, even though the latter exhibited greater potency on inhibiting the first response. These results clearly demonstrate that our screening system can readily identify use-dependent properties of compounds.

Figure 33:
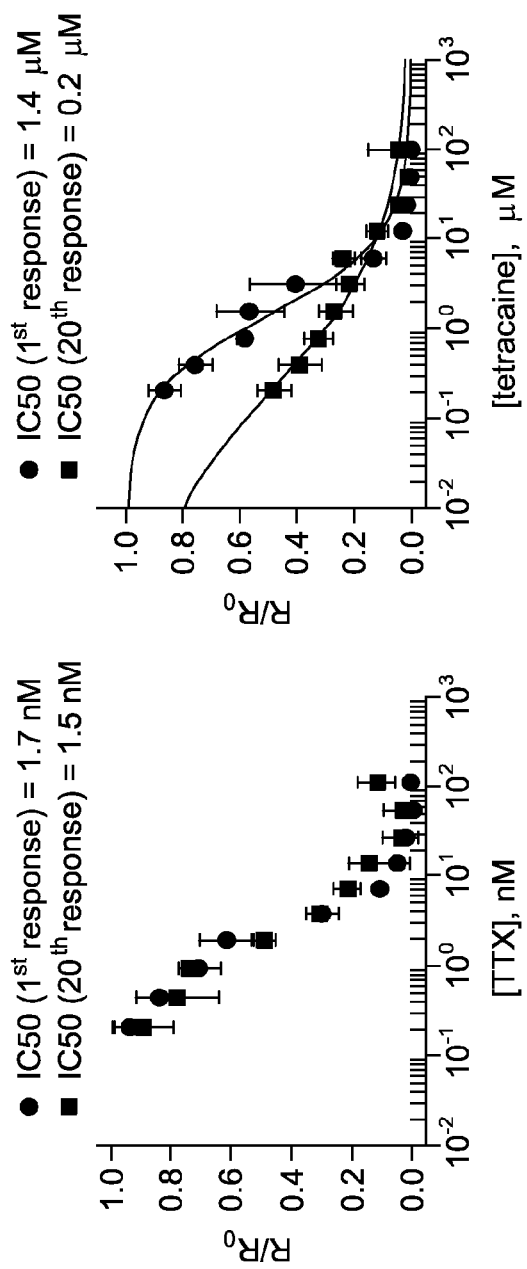
FIG. 33 Shows the use dependent effects of four different compounds using repetitive electrical stimulation at 1 Hz for 20 seconds and then comparing the $1^{st}$ and $20^{th}$ peak responses.
Figure 33:
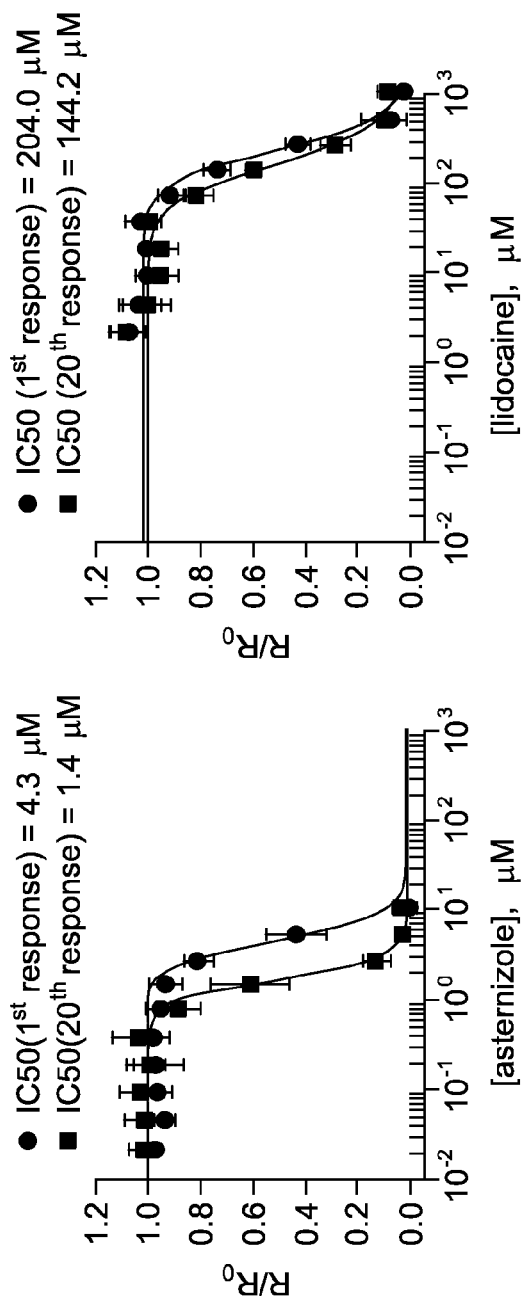

FIG. 33 summarizes the concentration dependence of fractional block of the first and the last peak ratio responses from data shown in FIG. 32A. The shift between two IC50s, measured respectively for the $1^{st}$ and $20^{th}$ peak responses, gives an estimate of use-dependence of a given compound. Here we use the ratio of IC50 ($1^{st}$ response) over IC50 ($20^{th}$ response), denoted as use-dependent index (UDI), to compare the use-dependence of tested compounds. The $1^{st}$ and $20^{th}$ peak responses were measured in the absence and presence of various concentrations of blockers. Data were plotted as the ratio of peak responses in the presence of a given blocker to that in the absence of the blacker. Data points represent the mean±S.D. of 4 replicates. The ratio of IC50 (pulse #1) over IC50 (pulse #20) is proportional to the use-dependence of a given blocker at 1 Hz. Titration was fit to a Michaelis-Menton equation: $R/R_0=[blocker]^n/([blocker]^n+IC50^n)$, $R_0$ denotes the normalized response obtained in the absence of blockers, n is the slope of the fit curve, IC50 is the half-inhibition concentration of the blocker.

Table 5 shows use dependence results for eight tested compounds and summarizes the best-fit values of concentration-response relationships for those compounds. The rank of UDI is tetracaine>yohimbine>amitriptyline>mexiletine>dibucaine>astemizole>lidocaine>TTX, suggesting that tetracaine and TTX were the most and least use-dependent compounds at the 1 Hz stimulus frequency in our experiments. The IC50s measured for the first peak ratio response are fairly comparable to those obtained with patch-clamp techniques for the same channel type at more negative holding potential. The latter condition is similar to our experimental condition where cells were stimulated from their resting membrane potential (about −60 mV, data not shown).

TABLE 5[a]

Use-dependence of $Na_V1.2a$ blockers at 1 Hz

| Compound | [b]UDI (1 Hz) | IC50 (µM) @ $1^{st}$ peak | Hill coeff. @$1^{st}$ peak | IC50 (µM) @ $20^{th}$ peak | Hill coeff. @$20^{th}$ peak | [c]AlogP (calculated) | Published IC50 (µM) |
|---|---|---|---|---|---|---|---|
| tetracaine | 8.40 | 2.77 ± 1.23 | 1.81 | 0.33 ± 0.20 | 0.66 | 2.96 | |
| yohimbine | 5.67 | 26.66 ± 7.26 | 2.05 | 4.70 ± 1.94 | 0.99 | 2.17 | |
| amitriptyline | 3.24 | 5.19 ± 1.57 | 2.65 | 1.60 ± 0.38 | 1.07 | 5.15 | 5.5 |
| mexiletine | 2.59 | 58.12 ± 11.01 | 3.07 | 22.46 ± 5.31 | 0.98 | 2.33 | [d]21~533 |
| dibucaine | 2.36 | 1.19 ± 0.22 | 2.35 | 0.51 ± 0.11 | 1.19 | 3.53 | |
| astemizole | 2.25 | 4.12 ± 2.03 | 2.67 | 1.83 ± 0.68 | 1.79 | 4.79 | |

16. Example 16

Applicability for High Throughput Screening

For the purposes of high throughput screening, the responses should be reliable enough to confidently tell the difference between active and inactive compounds. This can be quantified by examining the distribution of the responses obtained under identical stimulation conditions, comparing native channels with fully blocked channels. Due to experimental uncertainty and noise in the system, there will be some scatter in the responses. We would like to be able to statistically quantify this scatter, and use it to predict the probabilities of misidentifying responses as either false positives or false negatives.

Figure 25:
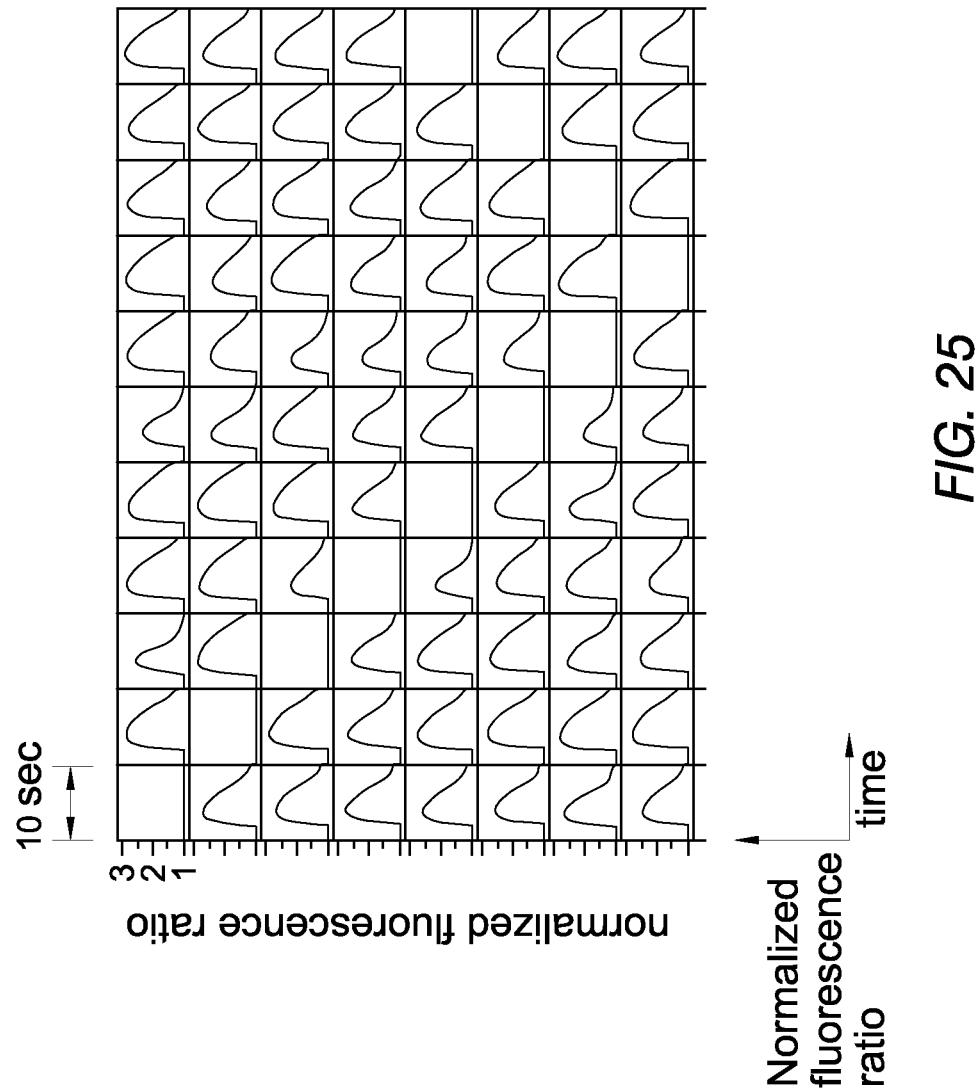
FIG. 25. Shows a 'Random' TTX spiking experiment. Each small box in this 11×8 array contains the ten-second time trace of a well at the corresponding position of a 96-well plate. The twelfth column was a control well without cells used for background subtraction and is not shown. Wells (1,1), (2,2), (3,3), etc. contained a blocking concentration of TTX.

To do this a plate of cells expressing the NaV2 voltage-dependent sodium channel was loaded with the FRET dyes. One well per column was 'randomly' spiked with 1 μM TTX, approximately 200 times the half-blocking concentration. The cells were assayed with a 20 Hz, 3 sec burst of 25 V/cm, 5 ms/phase, biphasic stimuli. The results are shown in FIG. 25. The wells spiked with TTX can easily be distinguished by eye as the wells with little or no detectable response.

Figure 26:
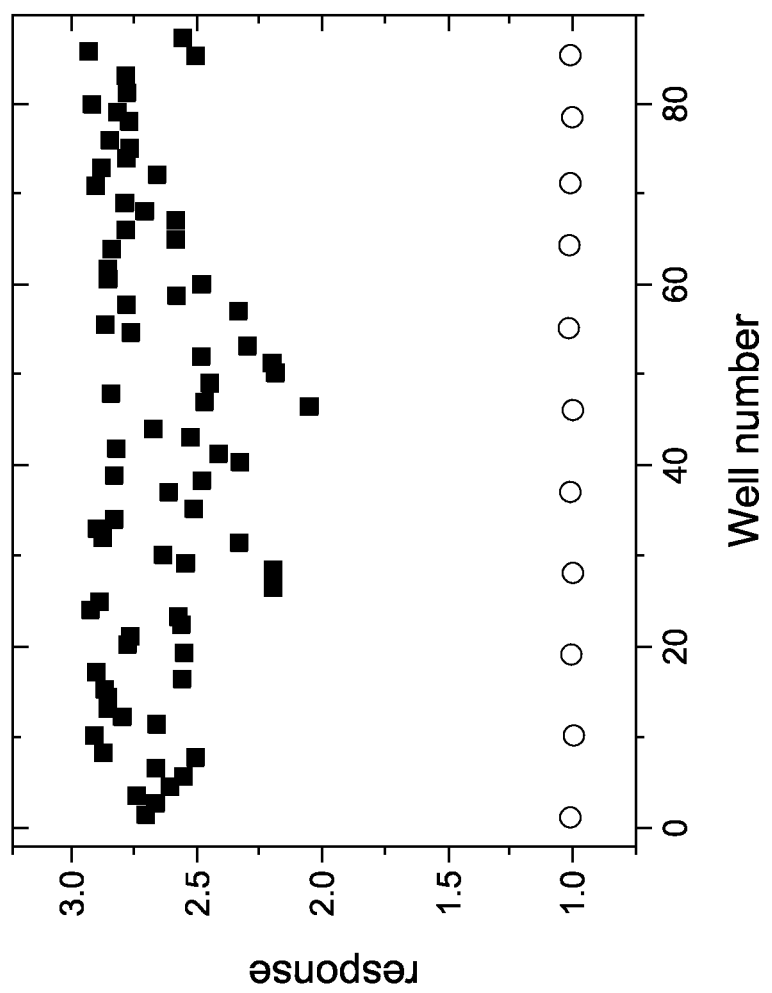
FIG. 26 Shows an analysis of the 'random' TTX spiking data shown in FIG. 25. The data points are the ratiometric response in the time window from 1.8-2.4 seconds after the beginning of the stimulus burst (i.e. at the peak of the response). The filled circles points were spiked with 1 μM TTX; the open circles had no blocker added.

The ratiometric response two seconds after the stimulus began is shown in FIG. 26. The two populations (blocked and unblocked) can easily be distinguished. The average blocked response was 1.011±0.004 while the average unblocked response was 2.67±0.21. The coefficient of variation for the unblocked response is 13%. The screening window (i.e. the difference between the populations normalized to the standard deviations, see Appendix A3) is 7.8($\sigma_1+\sigma_2$), where $\sigma_1=0.21$ is the standard deviation of the unblocked response and $\sigma_2=0.004$ is the standard deviation of the blocked response. If we take the cutoff point to distinguish blockers from nonblockers midway between the populations (at 1.042), then the rate of statistical false negatives and false positives (assuming a normal distribution) is 1-prob (7.75)=$10^{-14}$. This suggests that during a screen of a large compound library ($10^8$ compounds), the probability of encountering a single false positive or false negative during the entire screen is only one in a million. For comparison, if the difference between the populations were only 3 and the cutoff was optimally placed, the false positive/negative rate would be 0.3%, a factor of $10^{11}$ higher. For an actual screen, in which we would want to include as hits compounds which do not give complete block, a tradeoff exists between detecting weak pharmacological activity and the rate of false positives. If, for example, we desire a false positive rate of 0.1%, then in this screen we can put the screening cutoff at 3.3 standard deviations below the mean of the unblocked response, or at 1.97. In this case, the rate of false negatives is effectively zero, and compounds which block only 50% of the response will be identified as hits.

Mathematically, there are two reasons that the blocked and unblocked populations overlap so little. First, the coefficient of variation of the unblocked response is relatively small. That is, each response is nearly identical to every other response. Second, and perhaps more importantly, there is absolutely no detectable response from the blocked wells. The scatter from blocked wells is consequently extremely small, so that we can place the boundary for distinguishing the populations very low.

In assays performed using liquid addition protocols for stimulation, addition artifacts generally give some small response with an associated scatter. The scatter of the blocked response reduces the screening window, increases the probability of false positives and false negatives, and limits the screener's ability to identify partial blockers.

17. Example 17

Screening in Complex Cell Lines

Figure 27:
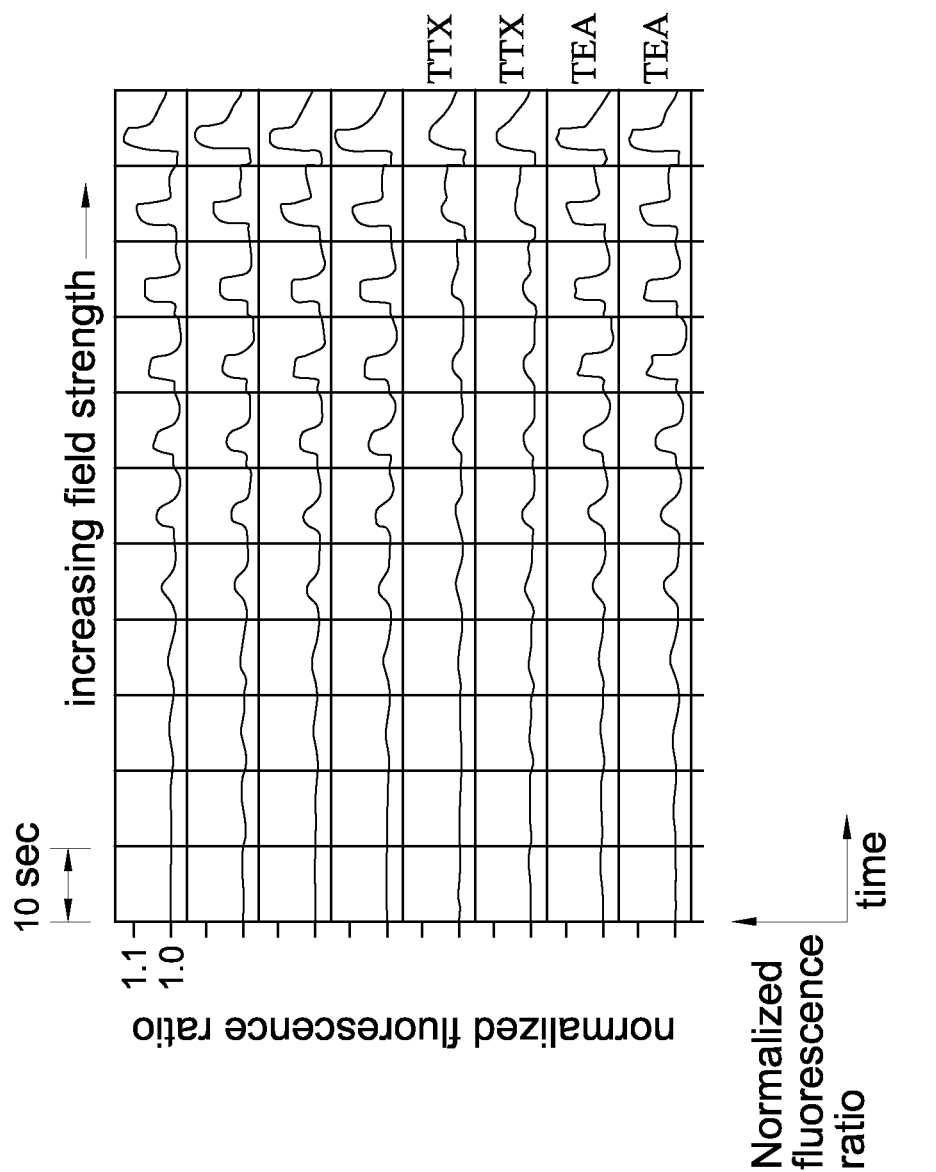
FIG. 27. Shows a full-plate view of electrically-stimulated HL5 cardiac muscle cells. Each individual panel represents the time trace of the normalized fluorescence ratio of a single well in the 96-well plate. Each well in a vertical column was stimulated simultaneously with the same field strength. Field strength increases from left to right. Rows 5 and 6 contained 10 µM TTX to partially block the voltage-dependent sodium channels. Rows 7 and 8 contained 10 mM TEA to partially block the voltage-dependent potassium channels.

The feasibility of electrical stimulation of cells expressing multiple channels was demonstrated using cultures of the HL5 cell line. These cells were generated by immortalizing cardiac muscle cells (Claycomb et al., 1998, PNAS 95: 2979-84). They contain several voltage-activated sodium, calcium, and potassium channels, as well as a strong inward rectifier potassium current and potassium and chloride leak currents. Cells were grown in 96-well microtiter plates and assayed at confluence. They were stained according to the protocol in Appendix A1. Ratiometric fluorescence measurements were made during electrical stimulation using VIPR™ as described above, and the data were analyzed according to the procedures in Appendix A2. Stimulus parameters were arbitrarily chosen to be: 3 second long burst at 10 Hz with a biphasic square wave stimulus kernel with a pulse duration of 5 ms/phase. Stimuli were performed at varying electric fields to determine the threshold field. Two rows of wells contained 10 μM TTX to partially block the cardiac sodium channel, and two rows contained 10 mM TEA to block the voltage-dependent potassium channels. FIG. 27 shows the normalized responses of each well. Generally as the electric field strength increases, the cellular response increases. The last three columns show signs of electropermeablization as the voltage continues to increase. In columns 6, 7, and 8, the ratio actually rebounds below the starting ratio, suggesting an after-hyperpolarization (a phenomenon caused by slow closing of voltage-dependent potassium channels).

The rate of the cellular response is extremely fast, and may be apparently limited by the ability of the ethyl oxonol to rapidly redistribute within the membrane. The rapid response is consistent with a high resting conductance of the cell due to the leak currents and the expression of potassium inward rectifier channels. TTX partially blocks the positive response, indicating that it is at least partially due to the voltage-dependent sodium current.

Figure 28:
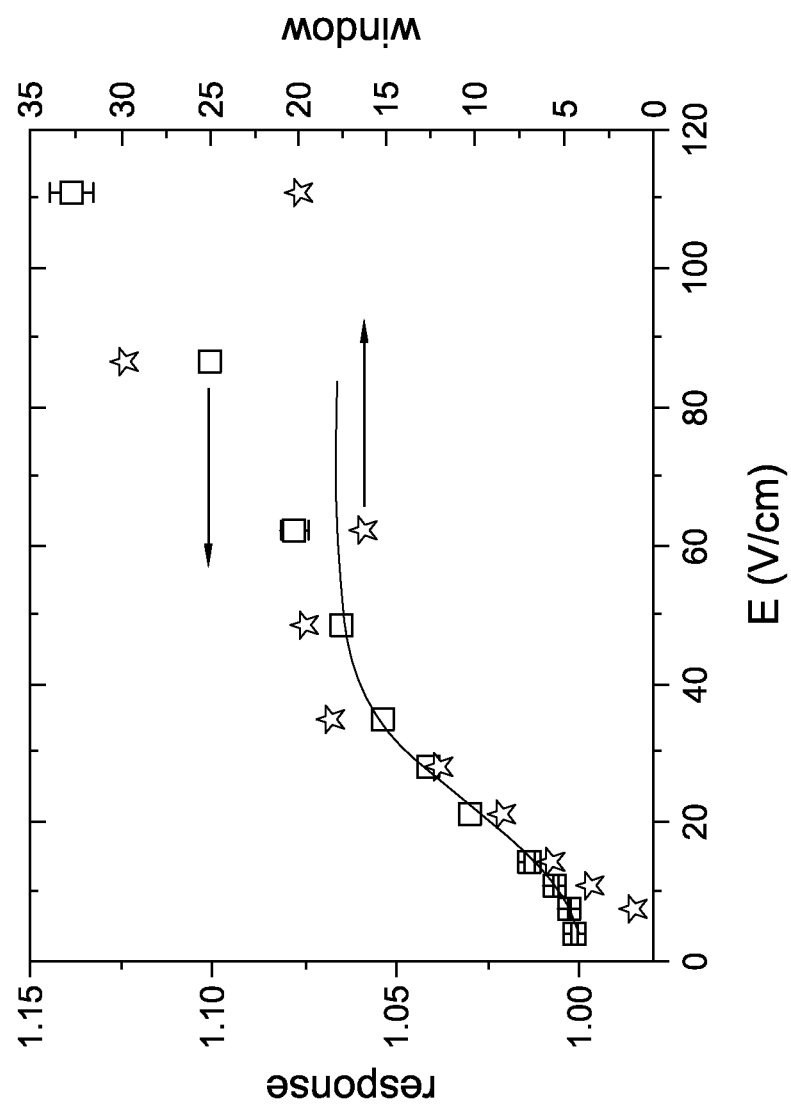
FIG. 28. Shows the response of HL5 cells as a function of the applied electric field strength. Black points are the average of the response of four wells with no added compounds. The solid line is a Boltzman fit to the data with $E_{50}$=22 V/cm. The points are the screening window: the difference between the response and the unstimulated response normalized to the standard deviation of the response (see Appendix A3).

FIG. 28 shows the response of the untreated cells (rows 1-4) as a function of the applied electric field. The response increases sigmoidally with the electric field. Above 50 V/cm, there is a sustained signal which is unaffected by TTX. As discussed previously, this behavior is consistent with the electropermeablization of the cellular membrane at high electric field strengths. Also shown in FIG. 28 is the screening window (see Appendix A3) as a function of the stimulus field.

These results demonstrate that HL5 cells can be effectively assayed using the electrical stimulation technique. Compounds which are known to modify different ion channels cause detectable changes in the response. Because these ion channels are identical to those expressed by the heart, such an assay would be useful as a secondary screen, to eliminate or mark for modification those compounds which may interfere with normal heart function. It could also be useful as a primary screen, to discover compounds which may have desirable effects on any one (or a combination) of the heart ion channels.

18. Example 18

Electrical Stimulation of Cell Cultures Using Surface Electrodes

Surface mounted electrodes were prepared on glass coverslips coated with chromium (as an adhesion layer) and gold (as a conductive layer). The metallized coverslips were custom-built by Thin Film Devices, Inc. (Anaheim Calif.). The coverslips were one inch square, 0.17 mm thick Corning 7059 glass. Metallization was performed by vacuum sputtering deposition. The chromium layer was approximately 1000 Å thick, and served as an adhesion layer. The gold layer was approximately 5000 Å thick, and served as a conductive layer. The resistivity of the deposited metal was less than 0.1 Ω/square. A 4-mm gap was etched through the metal by hand-masking the metal surface with a chemically-resistant polymer (S1400-27, Shipley Co., Marlborough Mass.), then etching through the metal layers with five minutes in Gold Etchant TFA, followed by five minutes in Chromium Etchant TFD (Transene Co., Danvers Mass.). The coverslips were attached to the bottoms of 96 well plates with silicone elastomer (Sylgard 184 (Corning), cured 90 minutes at 70° C.). After sterilizing with 365 nm UV irradiation for 30 minutes and coating with the cell adhesion molecule poly-D-lysine (molecular weight 300,000, 1 mg/mL in Dulbecco's phosphate buffered saline for 30 minutes, then rinsed 3 times with distilled water), living cells could be successfully grown and cultured on the electrode surfaces.

To validate the surface electrode stimulator CHO cells at an initial density of approximately 1000 cells/mm$^2$ were plated into the wells of the 96 well plate and left to attach for approximately 16 hours. These cells were transfected to express a potassium channel, which set the transmembrane potential to around −80 mV, and the NaV3 sodium channel. After reaching confluence, the cells were loaded with the voltage-sensitive FRET dye combination of CC2-DMPE and DiSBAC$_2$(3) as described in Appendix A1. The metal surface electrodes were connected to the output of a pulse generator, which in this case was an exponential-decay electroporator (Gene Pulser II, Bio-Rad Corp., Hercules Calif.). Ratiometric fluorescence imaging was performed on a Zeiss Axiovert TV microscope, equipped with a 75 W xenon arc lamp light source. Excitation light was filtered using a 405±10 nm dielectric interference filter and a 445 DXCR dichroic mirror. Emission light was split with a second 525XR dichroic mirror, and measured with a pair of Hamamatsu HC124 photomultiplier tubes (PMTs). One PMT had a 475±40 nm dielectric interference filter in front of it to monitor the blue fluorescent signal. The second PMT had a 580±35 nm dielectric interference filter in front of it to monitor the orange fluorescent signal. The optical filters and dichroic mirrors were purchased from Chroma Technology Corp., Battleboro Vt. Ratiometric fluorescence imaging was performed on fields containing approximately 100 cells. Correction for background fluorescence was performed by measuring the blue and orange signals in a field with no cells, then subtracting these from the signals obtained from the cells. Then the ratiometric signal, proportional to the transmembrane potential changes, was calculated as described in Appendix A2.

The stimulation protocol used single, monophasic electric field pulses of variable amplitude. The pulses were exponential-decay waveforms with a 4.3 ms decay time constant. The amplitude at the beginning of the pulse was varied from zero to 56 V/cm.

Figure 29:
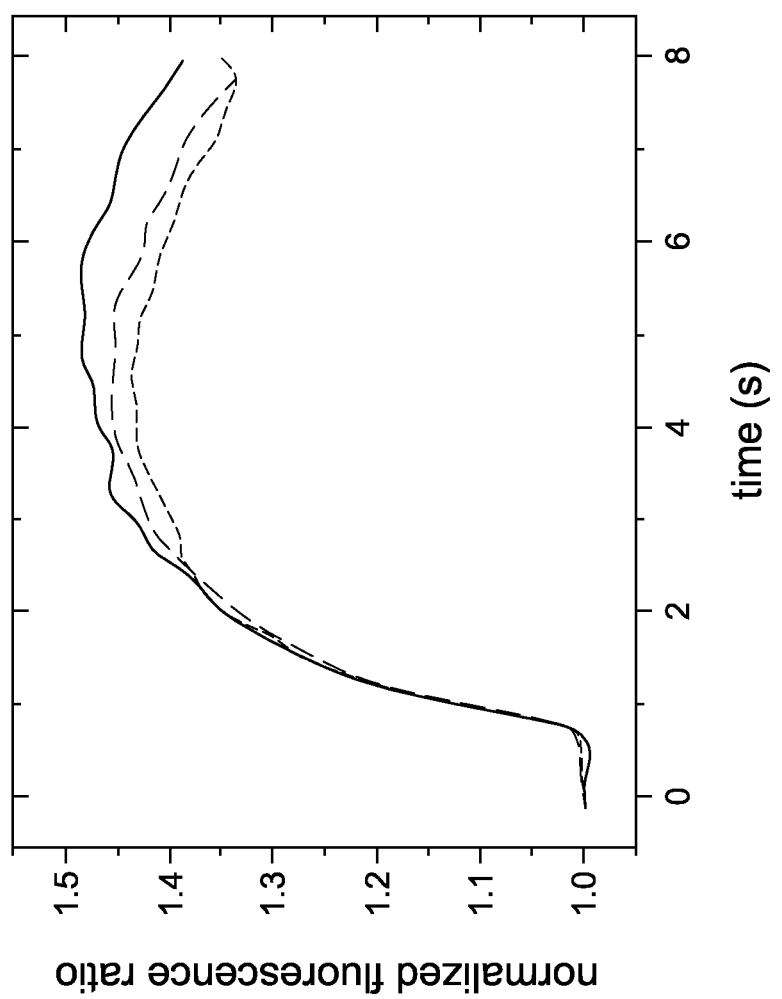
FIG. 29 The typical voltage response for CHO cells expressing a potassium channel and the NaV3 sodium channel after a three separate stimulation cycles using surface electrodes.

A typical voltage response for CHO cells expressing a potassium channel and the NaV3 sodium channel after a three separate 45 V/em stimulation responses are shown in FIG. 29 for the same field of cells, demonstrating repeatability of the response. The speed of the response in this case is limited primarily by the response time of the mobile hydrophobic dye, which for the ethyl oxonol used is about 0.5 second.

Figure 30:
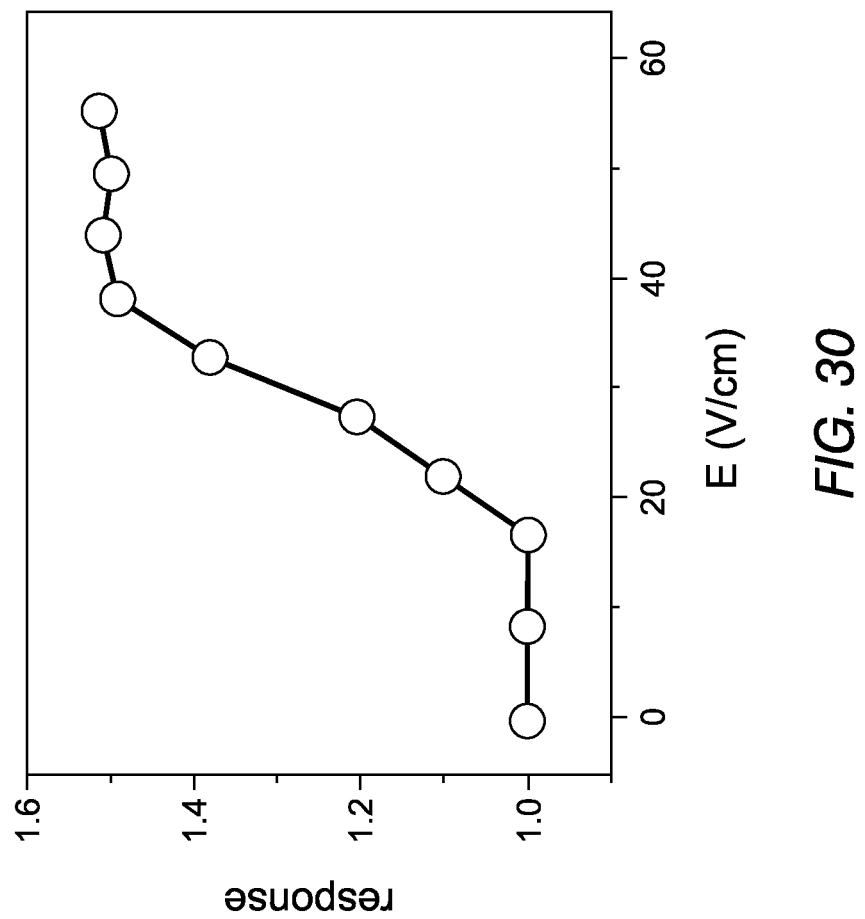
FIG. 30 Shows the average ratiometric response of a population of cells grown in a 96 well multiwell plate stimulated with monophasic stimuli of varying field strengths via surface electrodes. The points in this curve are the average peak response of 4 stimulations on the same culture.

The average ratiometric response of a population of cells grown in a 96 well multiwell plate stimulated with monophasic stimuli of varying field strengths is shown in FIG. 30. The points in this curve are the average peak response of 4 stimulations on the same culture. As is to be expected from an action-potential-type response curve, there is no detectable response below about 18 V/cm. The threshold region is relatively narrow. Between about 20 and 40 V/cm the response increases with increasing field strength. Above 40 V/cm the response plateaus.

19. Example 19

Analysis of Wild-Type RBL Cells Expressing IRK1

Rat basophilic leukemia (RBL) cells endogenously express the potassium inward rectifier channel IRK1 (Wischmeyer et al, Pflugers Arch. 429:809-819, 1995). This channel selectively conducts potassium ions, with a highly nonlinear conductance characteristic. The conductance is nearly linear below the potassium reversal potential $V_K$, and rapidly drops to near zero beginning at about 10 mV positive of $V_K$. Cells expressing large amounts of inward rectifier channels tend to have resting transmembrane potentials within a few millivolts of $V_K$.

On the side of the cell where the transmembrane potential is driven positive by an external electric field applied to cells expressing IRK1 and few other ion channels, the IRK1 channels will rapidly close and cease conducting. On the side of the cell where the transmembrane potential is driven negative, the IRK1 channels will open and pass potassium current. If this side of the cell is driven sufficiently negative, so that the local transmembrane potential is more negative than $V_K$, a net inward potassium current will exist. This current will cause a positive global transmembrane potential change. Because the IRK1 channel does not inactivate, this current should be sustained for as long as the external field is applied.

Figure 31:
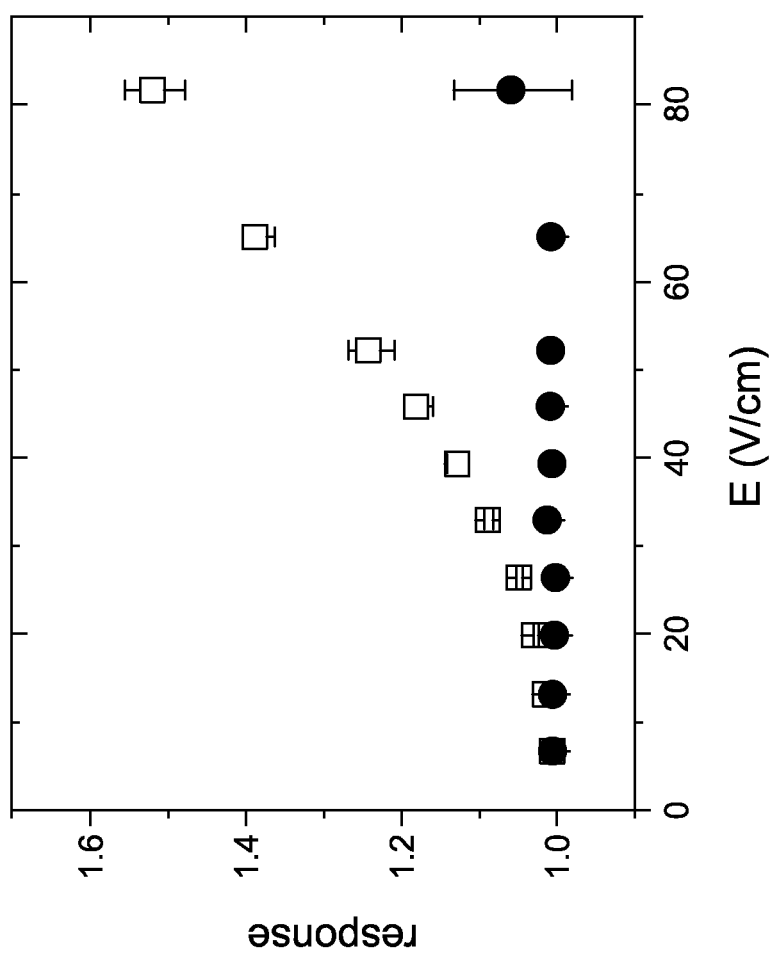
FIG. 31 Shows the cellular response as a function of the stimulus field for wild type RBL. Error bars are standard deviations. Open symbols: no added blockers. Filled symbols: 400 µM TEA added to block IRK1 channels.

Adherent RBL cells were seeded into 96-well plates and loaded with FRET dyes as described in Appendix A1. Three rows of wells contained 400 μM barium chloride to block the IRK1 channel. The plates were analyzed using a VIPR™ reader while being electrically stimulated with a biphasic stimulus train repeated at a frequency of 50 Hz and with a 5 ms/phase pulse duration. The stimulation pulse train occurred for a total duration of 5 seconds and the digitization rate for data collection was 50 Hz. The applied electric field was fixed for each column of eight wells, and was varied from 7.2 to 72 V/cm. The data were analyzed according to the procedures in Appendix A2. The normalized ratio after three seconds of stimulation was calculated, averaged for the two population of wells (with and without barium block), and plotted as a function of the applied field in FIG. 31. The error bars are standard deviations of the responses. Open squares are the responses without barium block; solid circles are the responses with barium block. The data from the wells with barium block indicate that there is no detectable voltage change during stimulation until the field reaches 80 V/cm, at which point some electropermeablization may be occurring. The unblocked wells show nearly linear response above a threshold at around 20 V/cm. This example clearly shows that the present invention can be used to modulate the transmembrane potential in either positive or negative directions, depending upon the stimulus parameters and the properties of the ion channels expressed by the cell.

20. Example 20

Paired-Pulse Stimulation Protocol for Screening and Biophysical Characterization of Candidate Ion Channel Modulators

In many electrophysiological studies, paired-pulse experiments have been used to characterize the recovery of voltage-gated ion channels from voltage inactivation and from blockade by channel blockers. Typically, voltage-gated channels are activated by a series of two consecutive activating voltage steps separated by various interpulse intervals (or recovery time) ranging from a few milliseconds to tens of seconds. The dissociation rate of blocker from inactivated channels then can be estimated from the ratio of two activated peak currents for the second and first pulse step and recovery time t. This relationship usually can be best fit with a single or two-exponential equation:

$$I_{Na} \text{ at 2nd pulse}/I_{Na} \text{ at 1st pulse} = A1\exp(-t/\tau_{fast}) + A2\exp(-t/\tau_{slow}) + A3,$$

where A1, A2, and A3 denotes constants; $\tau_{fast}$ and $\tau_{slow}$ are the time constants for the fast and slow recovery.

Figure 34A:
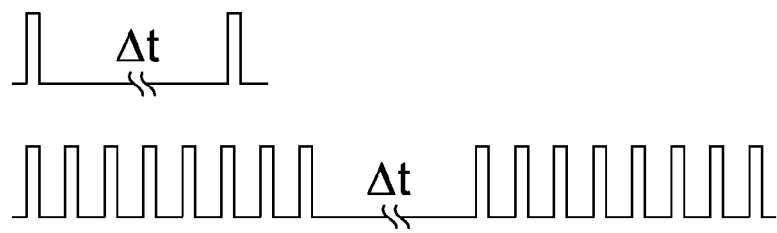
FIG. 34A Shows an example of a stimulation protocol to study recovery of channels from tonic block and use-dependent block.
Figure 34B:
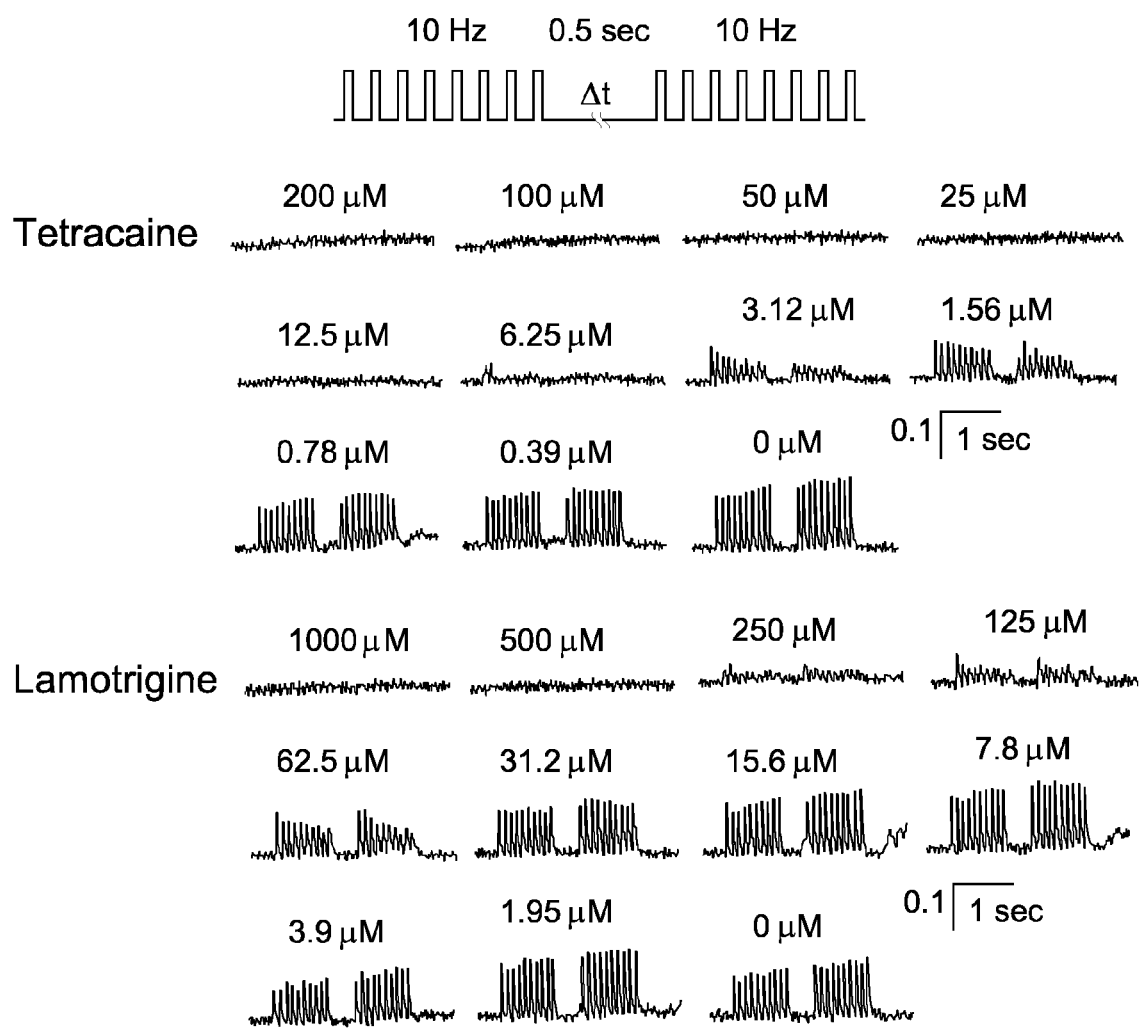
FIG. 34B shows concentration dependent recovery from tetracaine and lamotrigine block at 0.5 s train interval.
Figure 35:
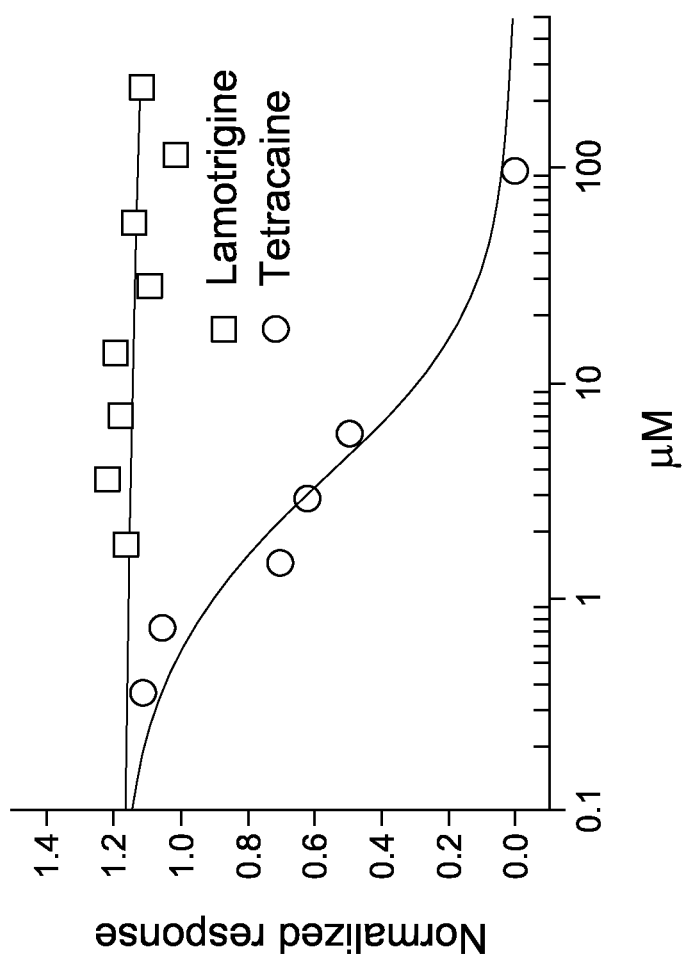
FIG. 35 Shows the concentration dependence of the recovery of channels from lamotrigine block and tetracaine block.

Many clinically used ion channel modulators have been found to attenuate the recovery phases, which represents an important mechanism of their actions. Our novel method utilizing fast-response dye and electrical field stimulation has provided a new approach to characterize such drug (or test compound)-channel protein interaction, yet at a higher-throughput format over conventional patch-clamping techniques. The following parameters can be estimated from our method:

a. dissociation constant of test compound
b. compound's frequency-dependence of recovery from
   tonic block
   use-dependent block
c. compound's concentration-dependence of recovery FIGS. 34 and 35 show application of a pair pulse protocol using NaVs and known use-dependent NaV antagonists. FIG. 34A shows an example of a stimulation protocol to study recovery of channels from tonic block and use-dependent block. Δt denotes the time interval between two pulse trains. FIG. 34B shows concentration dependent recovery from tetracaine and lamotrigine block at 0.5 s train interval. Cells expressing Nav1.8 were stimulated with two 10-Hz monophasic pulse trains, separated by a 0.5 s resting period. Each pulse train consisted of 3 ms, 80 Vp-p single pulses. Recovery of channel from block was determined by the ratio of two first peak fluorescence responses induced by each of pulse trains (2nd peak/1st peak), of which 1 indicates full recovery. These data demonstrated that the recovery of channels from lamotrigine block was not significantly dependent on the concentrations of lamotrigine tested at 0.5 seconds Δt. By contrast, the recovery of channels from tetracaine block exhibited strong dependence on the concentrations of tetracaine, shown in FIG. 35.

21. Example 21

Paired-Pulse Stimulation Protocol using Varying Time Intervals

Figure 36A:
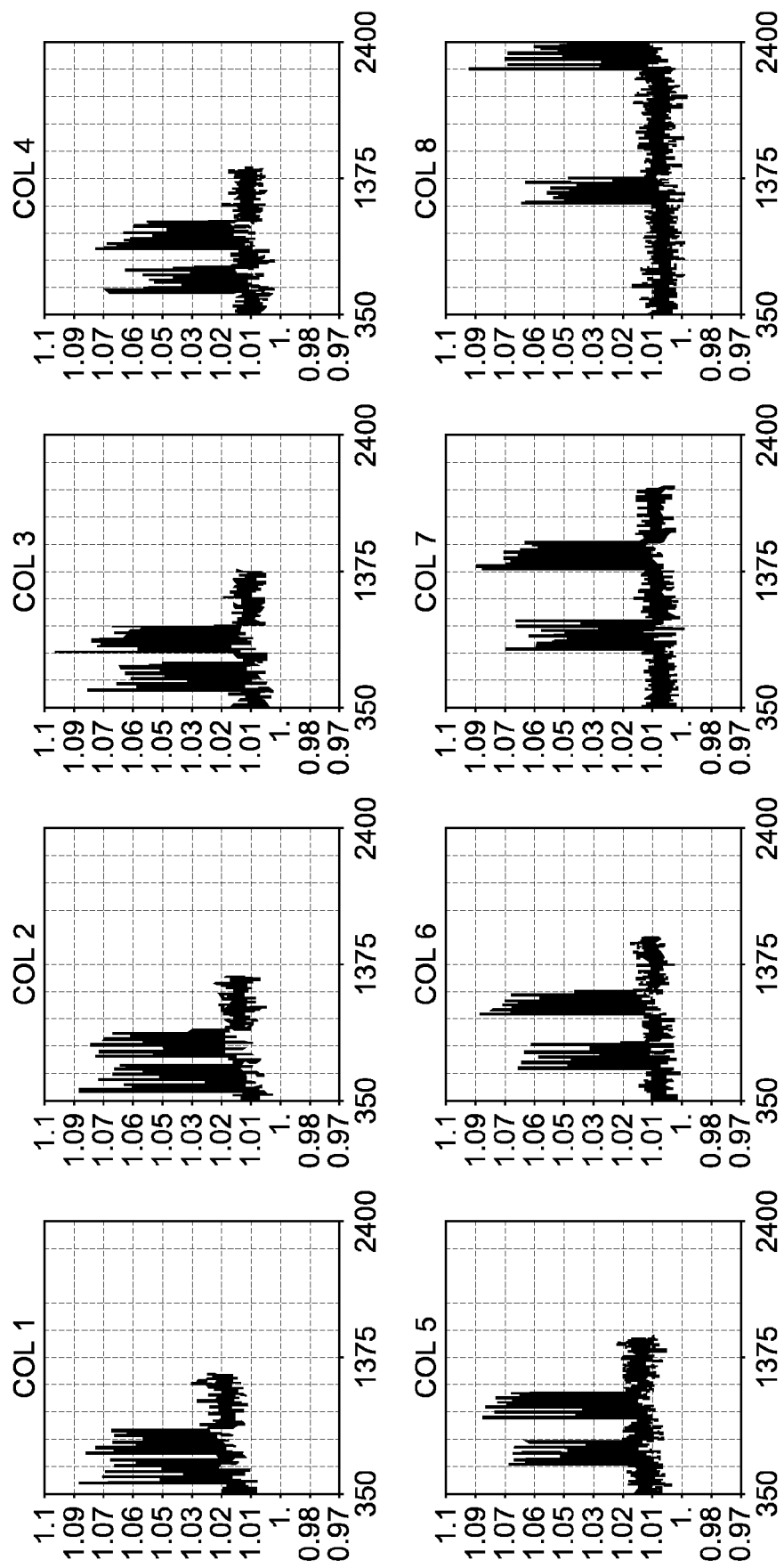
Figure 36B:
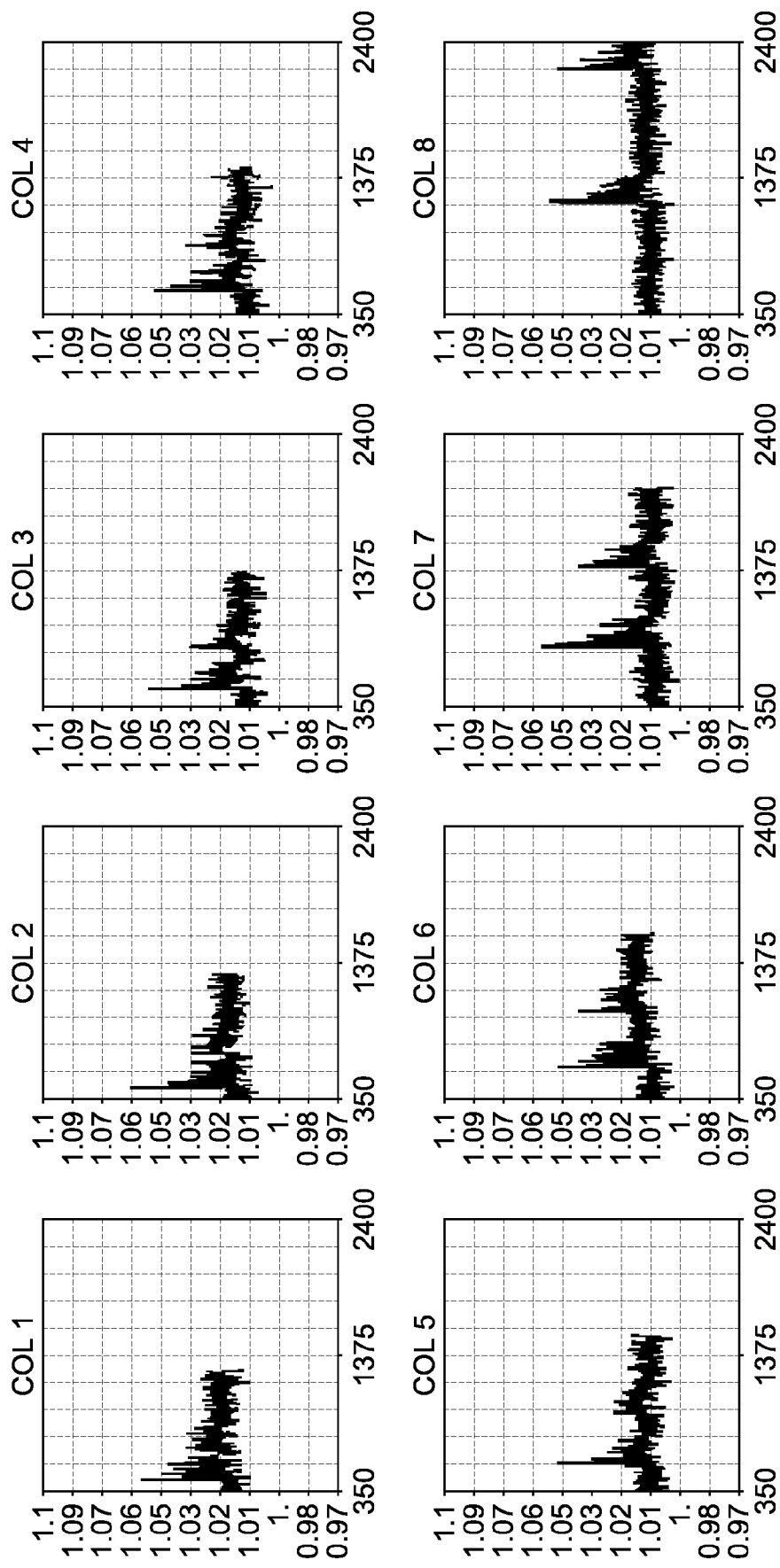
FIG. 36B shows the results for tetracaine block at 4 µM for different time intervals.

The recovery of channels from block using different time intervals Δt was also considered for lamotrigine and tetracaine. FIG. 36A shows the results for lamotrigine block at 50 µM for different time intervals while FIG. 36B shows the results for tetracaine block at 4 µM for different time intervals.

Figure 37:
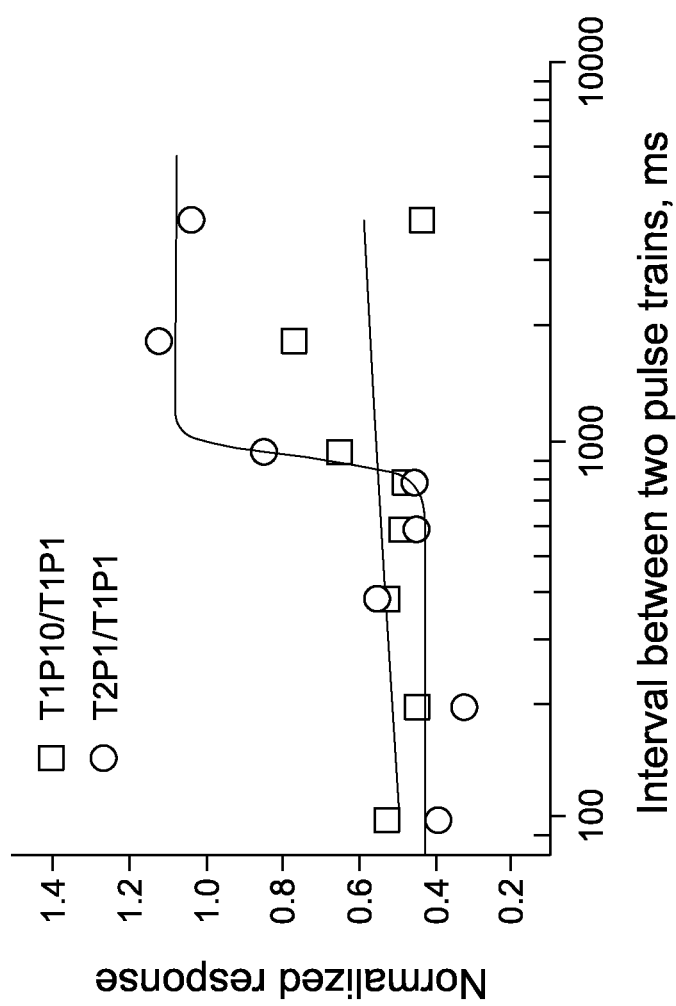
FIG. 37 Shows the recovery time contrast between tetracaine and lamotrigine.

The concentrations of lamotrigine and tetracaine were set at approximately the IC50 values, determined from previous experiment, to be 50 µM and 4 µM, respectively. The time interval between two 10-Hz pulse trains was varied in each column of plates from 0.1 s to 4 s, as indicated. In the presence of 50 µM lamotrigine, the ratio of two first peak fluorescence ratio responses were not significantly changed by increasing Δt, indicative of fast recovery of channel from lamotrigine block. By contrast, the recovery of channel from tetracaine block was much slower, which requires as long as 4 s of resting period. This suggests that the off-rate of tetracaine binding is significantly slower than that of lamotrigine. As shown in FIG. 37, tetracaine at 4 µM requires approximately 1000 ms or 1 s to recover from use-dependent block. This is in contrast to lamotrigine which recovers very quickly.

22. Example 22

Stimulation of Synchronous Voltage Oscillations and Drug Screening Method for Use-Dependent Compounds that Dampen, Reduce, and Modulate the Frequency of Action Potential Firing or Repetitive Voltage Transients

Figure 38:
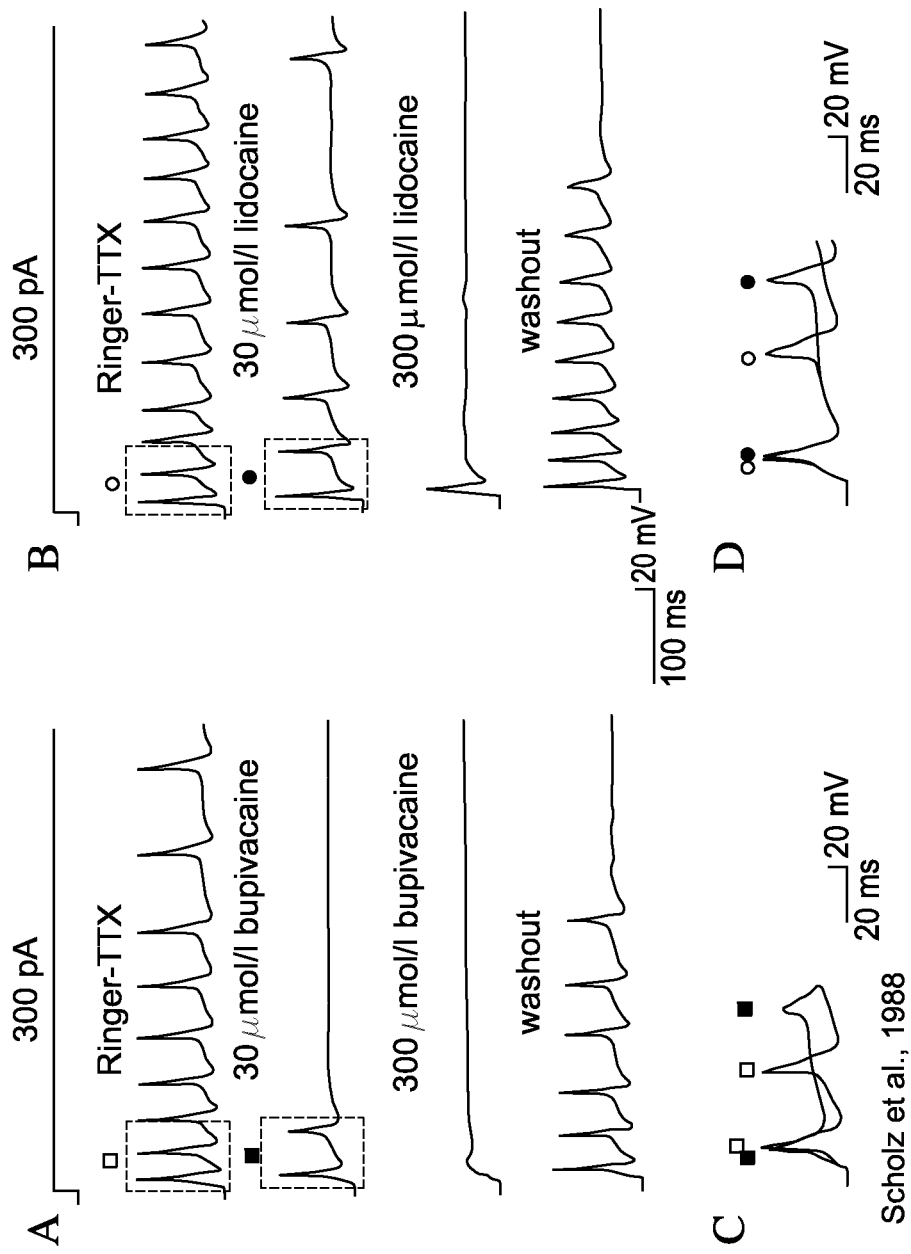
FIG. 38 Shows reduction of firing frequency by bupivacaine and lidocaine in Aδ- or C-type neuron slice preparation.

FIG. 38 shows reduction of firing frequency by bupivacaine and lidocaine in Aδ- or C-type neuron slice preparation. Use-dependent block of TTX-resistant Nav channels by bupivacaine and lidocaine resulted in slower firing rate in neuron slice preparation (Scholz et al., 1998). This effect can be reproduced by optical hexyl oxonol assay in non-excitable cells with the use of high-frequency monophasic pulses.

Figure 39:
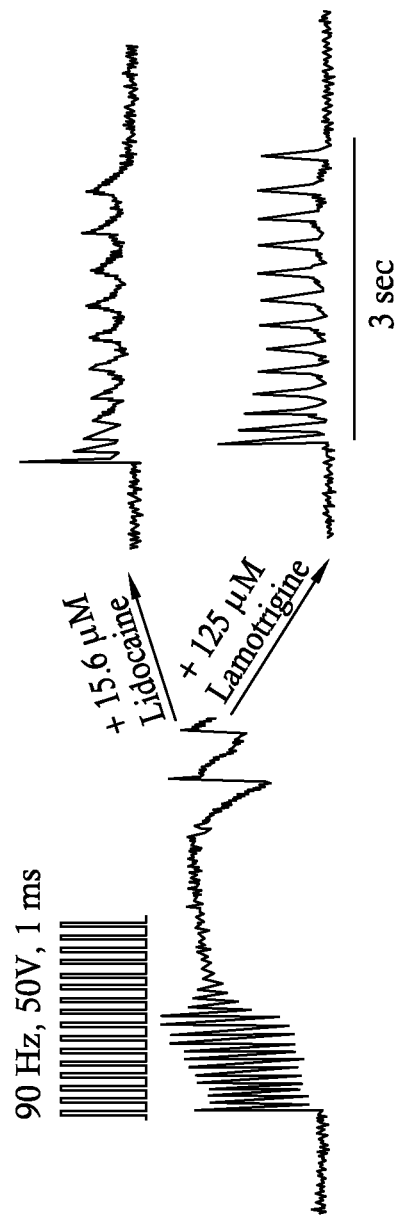
FIG. 39 Shows that induced spontaneous firing of Nav1.8 expressing cells is slowed by lamotrigine and lidocaine.

FIG. 39 shows induced spontaneous firing of Nav1.8 expressing cells is slowed by lamotrigine and lidocaine. The representative fluorescence ratio responses from Nav1.8 cells, induced by 90 Hz 50V 1 ms monophasic pulses, in the absence and presence of 15.6 µM lidocaine or 125 µM lamotrigine. Without the presence of Nav blockers, high-frequency monophasic stimulation induced spontaneous oscillation of fluorescence response at frequency of 6-10 Hz. Addition of lidocaine or lamotrigine gradually increased the interspike interval (or decreased firing frequency), accompanied by the reduction of peak response. This behavior is analogous to the use-dependent effect of these blockers on primary neurons.

23. Example 23

Detection of Use-Dependent Blocker of CaV with Method

Assays can also be developed using fast membrane potential sensors, such as $DISBAC_6(3)$ and CC2-DMPE voltage-sensitive FRET probes, to detect use-dependent compounds for voltage-gated Ca targets. The following illustrative example is for an N-type calcium channel using hardware compatible with 96 well plates.

Prepare a solution of 2× CC2DMPE and $DISBAC_6(3)$ by Vortexing together 10 mM CC2DMPE (in DMSO) and 10 mM $DISBAC_6(3)$ (in DMSO) with an equivalent volume of 10% pluronic (in DMSO). Vortex in required amount of bath. Each cell plate will require 5 ml of this solution. Wash plate with a plate washer leaving a residual volume of 50 L/well. Add 50 µL of 2×CC2DMPE to wells. Resulting concentrations of dyes will be 4 µM CC2-DMPE and 1.25 µM DIS- BAC₆(3). Stain for 30 minutes in the dark at RT. The test compounds are prepared at 2× concentration in extracellular ringer solution and added to wells containing stained cells. Stimulation parameters such as stimulation frequency, pulse duration, stimulation voltage can be easily manipulated to elicit desired responses.

Figure 40:
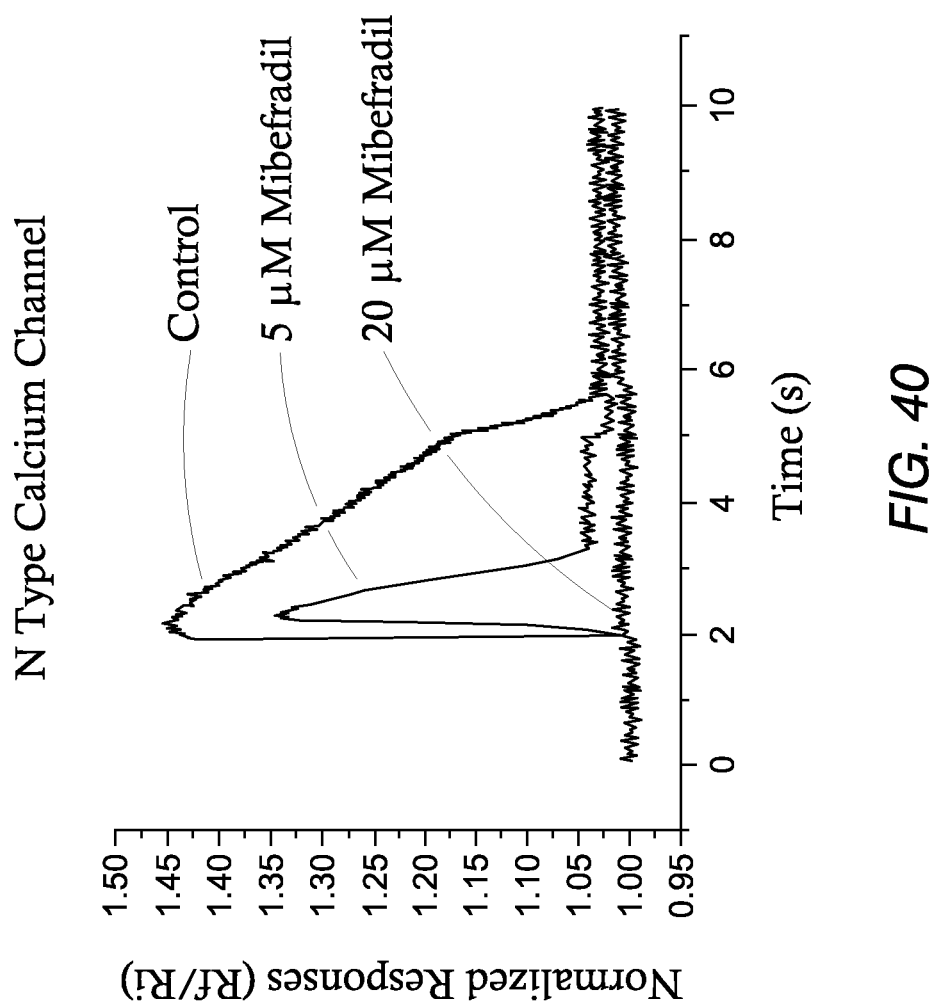
FIG. 40 Shows detection of the use-dependence of Mibefradil using a hexyl assay.

FIG. 40 illustrates an example of how a use-dependent compound such as mibefradil can be detected using this hexyl assay. The change in the response lineshape at 5 µM compound is indicative of use-dependent block.

24. Example 24

Figure 41:
FIG. 41 Shows the effect of increased potassium levels on sodium channel blockage by lamotrigine and tetracaine.

Technique for Identifying Voltage-Dependent Compounds (a Subset of Use-Dependent Activity) using Stimulation Instrumentation and Optical Methods in the Presence of Different External Potassium Concentrations We have developed a dorsal root ganglion (DRG) neuron assay on the electrical stimulation with optical detection platform that allows us to detect and quantify voltage dependent blockers of the sodium channels in these neurons. The DRG neurons were dissociated from neonatal rat pups and stained with FRET voltage sensing dyes. The neurons were then placed in the middle of the well on a 96 well plate and preincubated with varying concentrations of the test compound. Electrical stimulation was applied and the resulting response recorded by the plate reader. Dose response plots were then constructed for each compound tested. Increased levels of potassium were then added to depolarize the neurons and move more of the sodium channels into the inactivated state. Dose-response plots before and after addition of elevated potassium showed a leftward shift in the relationship and a corresponding decrease in the $IC_{50}$. This estimates the degree of voltage or state dependence for these compounds. FIG. 41 shows data from tetracaine and lamotrigine, two well known voltage dependent sodium channel blockers before and after addition of 16 mM potassium. As shown, the high potassium levels depolarize the cells. The compounds' block is voltage dependent, a type of use-dependent activity. These compounds block with higher affinity at depolarized membrane potentials as indicated in the leftward shifted dose response curves. This example illustrates also the use of this method with primary neurons.

25. Example 25

L Type Calcium Channel Antagonist Assay Using Electrical Stimulation and FRET Voltage Sensing Dyes The L-type calcium channel plays an important role in cardiac contraction and vascular smooth muscle tone. Antagonists of this target have demonstrated utility in hypertension and arrhythmia. Drug development compounds for other indications should avoid block of the L-type calcium channel to minimize cardiovascular side effects. We have developed a 96 well plate assay for antagonists of the L-type calcium channel that incorporates electrical stimulation in the presence of $DISBAC_2(3)$ and CC2-DMPE voltage-sensitive FRET probes.

Figure 42:
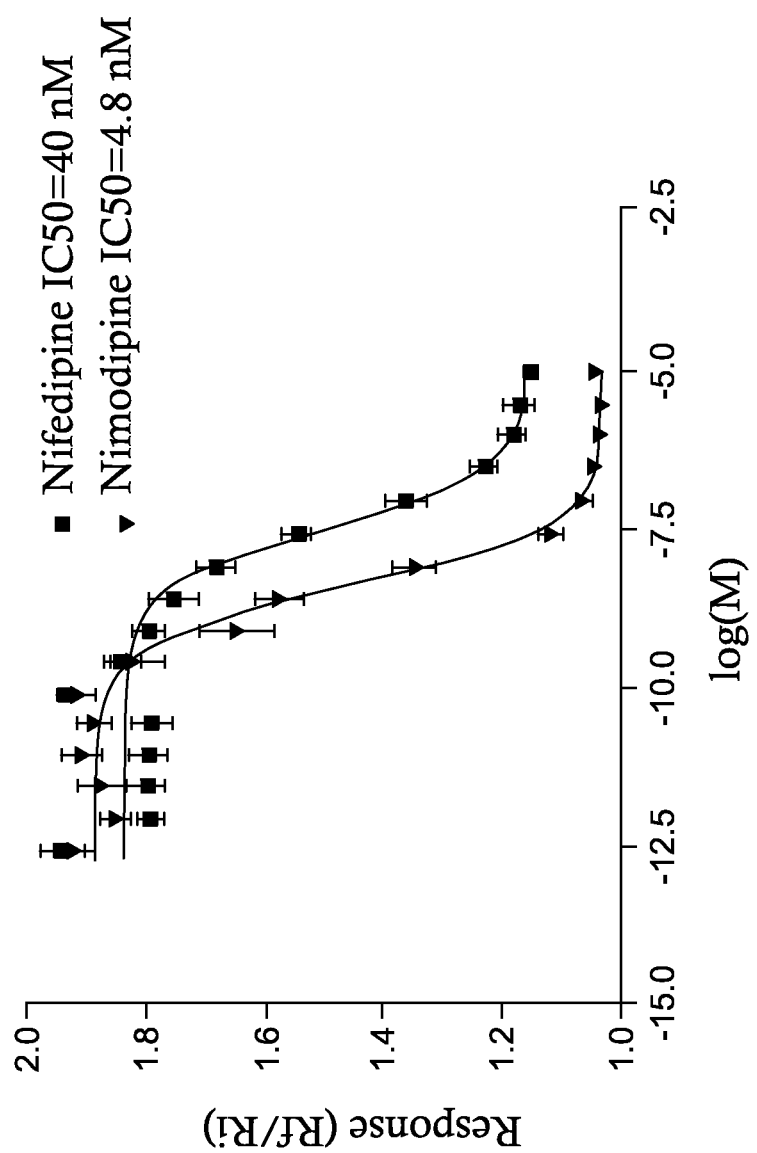
FIG. 42 Shows block of the L-type calcium channel by nifedipine and by nimodipine.

The following protocol was used. After washing the plate with a plate washer, the cells were stained with 10 µM CC2-DMPE in the required bath solution in the dark at room temperature for 30 minutes. The plate was then washed and stained with 3 µM $DISBAC_2(3)$, including 500 µM VABSC1 in the solution. Compounds were added in the second staining solution. The cells were assayed on the hardware platform using an optimized electrical stimulation protocol. FIG. 42 shows block of the L-type calcium channel with the potent dihydropyridinesnifedipine and nimodipine. The $IC_{50}$ value is similar to that reported in the literature.

The present invention expands the applicability of electrical stimulation to include non-excitable cells, by providing instrumentation and methods that enable effective stepwise control of membrane potential without resulting in significant electroporation. The present invention achieves this result via the use of highly uniform, repetitive pulses of electrical stimulation applied to the medium surrounding the cells. The applied electric fields typically do not directly alter the average transmembrane potential of the cell, but instead create symmetric positive and negative transmembrane potential changes on the sides of the cell facing the cathode and the anode, respectively.

The approach exploits the ion selectivity and the non-linear gating and conductance characteristics of voltage-dependent ion channels. The approach also exploits the fact that typical intact cells have long time constants for decay of transmembrane potential changes. Even in those cases where the charge injected into the cell by a single stimulus pulse is too small to be detected reliably, appropriately applied multiple stimulus pulses can build large net transmembrane potential excursions. By varying the number, duration, and the shape and amplitude of the pulses, it is possible to artificially set, or change the transmembrane potential of living cells in a fashion that is similar to patch clamping. Other channels, leak currents or transporters that are not classically considered voltage-dependent, can also be assayed by inducing transmembrane potential changes using a second, voltage-dependent channel and detecting the current flow or transmembrane potential changes as a result of activation of the target channel or transporter.

The present method is robust, compatible with optical detection methodologies and readily amendable to a wide range of potential applications including high throughput screening for use in drug discovery. In many assay formats direct electrical stimulation avoids the requirement for liquid addition, making the assay simpler. Complex manipulations of the transmembrane potential can readily be accomplished using variations in the stimulation protocol. Thus, virtually any voltage-sensitive channel can be induced to open regardless of the state of inactivation or voltage dependency. For high throughput drug discovery this relaxes the requirements for specialized cell types, and allows assays to be rapidly performed with readily available cell lines.

All publications and patent documents cited in this application are incorporated by reference in their entirety for all purposes to the same extent as if each individual publication or patent document were so individually denoted.

Appendices

A1. Staining Protocol of Voltage FRET Dyes
  1. Reagents (a) Assay buffer #1

140 mM NaCl
4.5 mM KCl
2 mM $CaCl_2$
1 mM $MgCl_2$

-continued 10 mM HEPES
10 mM glucose pH 7.40, 330 mOs/kg
(b) Pluronic stock (1000X)

100 mg/mL pluronic 127 in dry DMSO
(c) Oxonol stock (3333X)

10 mM DiSBAC$_2$(3) in dry DMSO
(d) Coumarin stock (1000X)

10 mM CC2-DMPE in dry DMSO
(e) ESS-CY4 stock (400X)

200 mM ESS-CY4 in water

2. Loading and Assay Protocol
1. Preparation of CC2-DMPE loading buffer. Normally for a 96-well plate, 10 mL of staining solution will be prepared per plate.
   i) Mix equal volumes (10 μL) of coumarin stock and pluronic stock in a tube.
   ii) Add 10 mL Assay Buffer #1 to tube while gently vortexing.
      Loading concentration: 10 μM CC2-DMPE and 0.1 μg/ml pluronic.
2. Prepare oxonol loading buffer:
   i) Mix equal volumes (3.3 μL) of oxonol stock and pluronic stock in a tube.
   ii) Add 10 mL Assay Buffer #1 to tube while gently vortexing.
   iii) Add 25 μL ESS-CY4 while vortexing.
      Loading concentration: 3 μM DiSBAC$_2$(3), 0.2 μg/ml pluronic, and 0.5 mM ESS-CY4.
   iv) If required, combine test compounds with the loading buffer at this time.
3. Rinse cells twice with Assay Buffer #1, removing all fluid from wells each time.
4. Add 100 μL CC2-DMPE loading buffer to each well. Incubate 30 minutes at room temperature, avoiding bright light.
5. Rinse cells twice with Assay Buffer #1, removing all fluid from wells each time.
6. Add 100 μL oxonol loading buffer to each well.
7. Incubate for 30 minutes at room temperature avoiding bright light. Use immediately.

A2. Analysis of VIPR™ Reader Data

Data were analyzed and reported as normalized ratios of intensities measured in the 460 nm and 580 nm channels. The process of calculating these ratios was performed as follows. On all plates, column 12 contained Assay Buffer #1 with the same DiSBAC2(3) and ESS-CY4 concentrations as used in the cell plates, however no cells were included in column 12. Intensity values at each wavelength were averaged in initial (before the stimulus) and final (during the stimulus) windows. These average values were subtracted from intensity values averaged over the same time periods in all assay wells. The ratios obtained from samples in the initial (Ri) and final windows (Rf) are defined as:

$$Ri = \frac{(\text{intensity 460 nm, initial} - \text{background 460 nm, initial})}{(\text{intensity 580 nm, initial} - \text{background 580 nm, initial})} \quad (A2.2)$$

$$Rf = \frac{(\text{intensity 460 nm, final} - \text{background 460 nm, final})}{(\text{intensity 580 nm, final} - \text{background 580 nm, final})} \quad (A2.1)$$

Final data are normalized to the starting ratio of each well and reported as Rf/Ri.

A3. Screening Window

The screening window W for a response is defined as follows. Data from multiple wells at identical stimulus conditions are required. The control wells can either be pharmacologically blocked or untransfected cell stimulated with the full electric field. Alternatively, one might use transfected cells with no stimulus applied.

Responses from experimental and control wells are measured. The average and standard deviations of the responses in the experimental (R±ΔR) and control (C±ΔC) wells are calculated. The screening window is defined as the difference between experimental and control signals normalized to the sum of the standard deviations.

$$W = \frac{R - C}{\Delta R + \Delta C} \quad (A3.1)$$

A general rule of thumb for an acceptable screening window is W>3. This allows one to choose a cutoff line midway between control and experimental responses which ensures a false negative/positive rate less than 1%. Assuming a normal distribution, the false positive/negative rate as a function of the screening window W is:

$$P_{false} = 1 - prob(W) \quad (A3.2)$$
$$= 1 - \frac{1}{\sqrt{2\pi}} \int_{-W}^{+W} \exp\left(-\frac{t^2}{2}\right) dt$$

TABLE A3.1

The false positive/negative rate P(W) as a function of the screening window W as defined in Equation A3.1.

| W | P(W) |
|---|---|
| 1 | 0.3173 |
| 2 | 0.0455 |
| 3 | 0.0027 |
| 4 | 6.334E−5 |
| 5 | 5.733E−7 |
| 6 | 1.973E−9 |
| 7 | 2.559E−12 |
| 8 | 1.221E−15 |
| 9 | <1E−18 |
| 10 | <1E−18 |

This calculation assumes that the cutoff for identification of a hit is placed an equal number of standard deviations away from the positive and negative control responses.

What is claimed is:
1. A method of high throughput characterization of the biological activity of one or more candidate compounds, the method comprising:
   placing a population of cells, solvent, and voltage sensitive dyes, into an area of observation in each of plurality of wells of a multiwell plate;

exposing said population of cells to at least one candidate compound;

exposing said population of cells in each of the plurality of wells to electric fields using extracellular electrodes positioned in the solvent of the plurality of wells to produce a change in transmembrane potential of said population of cells while exposed to said compound;

wherein said electric fields comprise a first pulse series of multiple pulses and a second pulse series of multiple pulses with a pause between the first pulse series and the second pulse series;

monitoring the transmembrane potential of said population of cells; and comparing the transmembrane potential of said population of cells in response to said electric fields at a first portion of said first pulse series with the transmembrane potential of said population of cells in response to said electric fields at a first portion of said second pulse series to test the effect of said one or more candidate compounds on said cells in a parallel assay high throughput manner.

2. The method of claim 1 wherein monitoring comprises optically monitoring.

3. The method of claim 2 wherein optically monitoring comprises detecting fluorescence emission of a FRET based voltage sensor from an area of observation containing said population of cells.

4. The method of claim 1 wherein a transmembrane potential ratio of the first portion of the second pulse series to the first portion of the first pulse series is indicative of ion channel recovery from block by said compound.

5. The method of claim 4 wherein a transmembrane potential ratio of approximately 1 is indicative of full recovery from the ion channel block of said compound.

6. The method of claim 4 wherein a transmembrane potential ratio of less than 1 is indicative of incomplete recovery from the ion channel block of said compound.

7. The method of claim 4 wherein the pause between the first pulse series and the second pulse series is maintained constant among each of the plurality of wells and the concentration of said compound is varied among the plurality of wells.

8. The method of claim 7 further comprising comparing said transmembrane potential ratios of the first portion of the first pulse series to the first portion of the second pulse series for the different compound concentrations in each of the plurality of wells.

9. The method of claim 8 wherein a difference in said transmembrane potential ratios between different concentrations of said compound in the sample wells is indicative of said compound's concentration-dependence of ion channel recovery.

10. The method of claim 1 wherein the concentration of said compound is maintained constant between each of the plurality of sample wells and the pause duration between the first pulse series and the second pulse series is varied between each of the plurality of wells.

11. The method of claim 10 further comprising comparing said transmembrane potential ratios of the first portion of the first pulse series to the first portion of the second pulse series for the different pause durations between the first and second pulse series in each of the plurality of wells.

12. The method of claim 11 wherein a difference in said transmembrane potential ratios between sample wells of different pause durations is indicative of use dependent block of an ion channel by said compound.

* * * * *

UNITED STATES PATENT AND TRADEMARK OFFICE
CERTIFICATE OF CORRECTION

PATENT NO. : 8,426,201 B2  
APPLICATION NO. : 12/568604  
DATED : April 23, 2013  
INVENTOR(S) : Michael P. Maher and Jesus E. Gonzalez, III Page 1 of 1

It is certified that error appears in the above-identified patent and that said Letters Patent is hereby corrected as shown below:

In the Specification:

At Column 6, Line 50, change "of equal to," to --or equal to,--.

At Column 8, Lines 13-15, change " $y(x) = y_c + \dfrac{A}{x_0^n + x^n}.$ " to -- $y(x) = y_0 + \dfrac{A}{x_0^n + x^n}.$ --.

At Column 34, Line 35, change "β-l" to --β-1--.  
At Column 35, Line 58, change "(h)" to --(b)--.  
At Column 41, Line 17, change "(h)" to --(b)--.  
At Column 56, Line 45, change "viva" to --vivo--.  
At Column 58, Line 11, change "or" to --of--.  
At Column 61, Line 14, change "nun," to --mm,--.  
At Column 66, Line 7, change "Ha" to --IIa--.  
At Column 74, Line 33, change "blacker." to --blocker.--.  
At Column 77, Line 62, change "V/em" to --V/cm--.  
At Column 80, Line 65, change "50 L/well." to --50 µL/well.--.

Signed and Sealed this  
Twenty-second Day of October, 2013

Teresa Stanek Rea  
*Deputy Director of the United States Patent and Trademark Office*